(12) United States Patent
Dasmahapatra et al.

(10) Patent No.: US 7,790,474 B1
(45) Date of Patent: Sep. 7, 2010

(54) P53 MODULATORS

(75) Inventors: Bimalendu Dasmahapatra, Nutley, NJ (US); Bernard R. Neustadt, West Orange, NJ (US); Mark Demma, Edison, NJ (US); Alan K. Mallams, Hackettstown, NJ (US); Henry A. Vaccaro, South Plainfield, NJ (US); Jonathan A. Pachter, Setauket, NY (US)

(73) Assignee: Schering Corporation, Kenilworth, NJ (US)

( * ) Notice: Subject to any disclaimer, the term of this patent is extended or adjusted under 35 U.S.C. 154(b) by 351 days.

(21) Appl. No.: 11/487,014

(22) Filed: Jul. 14, 2006

Related U.S. Application Data

(60) Provisional application No. 60/699,652, filed on Jul. 15, 2005, provisional application No. 60/700,058, filed on Jul. 15, 2005, provisional application No. 60/700,056, filed on Jul. 15, 2005.

(51) Int. Cl.
*G01N 33/536* (2006.01)
(52) U.S. Cl. .................... 436/536; 436/518; 435/7.1; 544/283
(58) Field of Classification Search .................... None
See application file for complete search history.

(56) References Cited

U.S. PATENT DOCUMENTS

| 6,921,765 B2 | 7/2005 | Bykov et al. |
| 7,348,330 B2 | 3/2008 | Bykov et al. |
| 2002/0048271 A1 | 4/2002 | Rastinejad et al. |
| 2005/0090510 A1 | 4/2005 | Bykov et al. |

FOREIGN PATENT DOCUMENTS

| WO | WO-03014144 A2 * | 3/2003 |

OTHER PUBLICATIONS

Abarzua, Patricio, et al., "Microinjection of Monoclonal Antibody PAb421 into Human SW480 Colorectal Carcinoma Cells Restores the Transcription Activation Function to Mutant p53", Cancer Research, 55:3490-3494 (1995).
Abarzua, Patricio, et al., "Restoration of the transcription activation function to mutant p53 in human cancer cells", Oncogene, 13:2477-2482 (1996).
Bykov, Vladimir J.N., et al., "Restoration of the tumor suppressor function to mutant p53 by a low-molecular-weight compound", Nature Medicine, 8(3):282-288 (2002).
Demma, Mark J., et al., "CP-31398 Restores DNA-binding Activity to Mutant p53 in Vitro but does not affect p53 Homologs p63 and p73", The Journal of Biological Chemistry, 279(44):45887-45896 (2004).
Foster, Barbara A., et al., "Pharmacological Rescue of Mutant p53 Conformation and Function", Science, 286:2507-2510 (1999).
Friedler, Assaf, et al., "A peptide that binds and stabilizes p53 core domain: Chaperone strategy for rescue of oncogenic mutants", Proc. Nat. Acad. Sci., 99(2):937-942 (2002).
Friedler, Assaf, et al., "Kinetic Instability of p53 Core Domain Mutants", The Journal of Biological Chemistry, 278(26):24108-24112 (2003).
Issaeva, Natalia, et al., "Rescue of mutants of the tumor suppressor p53 in cancer cells by a designed peptide", Proc. Nat. Acad. Sci., 100(23):13303-13307 (2003).
Luu, Yvonne, et al., "The p53 Stabilizing Compound CP-31398 Induces Apoptosis by Activating the Intrinsic Bax/Mitochondrial/Caspase-9 Pathway", Experimental Cell Research, 276:214-222 (2002).
Peng, Yanhua, et al., "Rescue of mutant p53 transcription function by ellipticine", Oncogene, 22:4478-4487 (2003).
Selivanova, Galina, et al., "Reactivation of Mutant p53 through Interaction of a C-Terminal Peptide with the Core Domain", Molecular and Cellular Biology, 19(5):3395-3402 (1999).
Takimoto, Rishu, et al., "The Mutant p53-Conformation Modifying Drug, CP-31398, Can Induce Apoptosis of Human Cancer Cells and Can Stabilize Wild-Type p53 Protein", Cancer Biology & Therapy, 1:47-55 (2002).
Wang, Wenge, et al., "Stabilization of p53 by CP-31398 Inhibits Ubiquitination without Altering Phosphorylation at Serine 15 or 20 or MDM2 Binding", Molecular and Cellular Biology, 23(6):2171-2181 (2003).
Wieczorek, Ania M., et al., "Structure-based rescue of common tumor-derived p53 mutants", Nature Medicine, 2(10):1143-1146 (1996).
Wischhusen, J., et al., "CP-31398, a novel p53-stabilizing agent, induces p53-dependent and p53-independent glioma cell death", Oncogene, 22:8233-8245 (2003).
Yang, Wei-Ping, et al., "Surface plasmon resonance based kinetic studies of zinc finger-DNA interactions", Journal of Immunological Methods, 183:175-182 (1995).

* cited by examiner

*Primary Examiner*—Misook Yu

(57) ABSTRACT

The present invention provides compositions as well as methods for identifying compositions useful for treating or preventing cancer.

10 Claims, No Drawings

P53 MODULATORS

This application claims the benefit of U.S. provisional application Nos. 60/699,652; 60/700,058; and 60/700,056; all filed on Jul. 15, 2005, each of which is herein incorporated by reference in its entirety.

FIELD OF THE INVENTION

The present invention relates, inter alia, to methods for identifying substances that stabilize p53 as well as to gene therapy comprising use of stabilized alleles of p53.

BACKGROUND OF THE INVENTION

The p53 tumor suppressor protein belongs to a superfamily of transcription factors. p53 is involved in a wide range of cellular activities that help ensure the stability of the genome and is involved in DNA damage repair, cell cycle arrest, and apoptosis via transcriptional regulation of genes involved in these activities or by direct interaction with other proteins. Mutations that inactivate p53 are present in over 50% of all cancers and are indicative of aggressive cancers that are difficult to treat by chemotherapy or ionizing radiation. The majority of inactivating mutations reside in the central core DNA binding domain (DBD)1 of p53. These mutations can be divided into two main classes, DNA contact mutants, like R273H, where the mutation alters a residue involved in contact with DNA, and structural mutants, like R249S, which result in structural changes in the p53 core domain.

One potential therapeutic approach to cancer would be restoration of growth suppression activity to mutant p53. Several approaches have been tried, ranging from microinjection of monoclonal antibody 421, C-terminal peptide of p53 and small molecules (Abarzua et al., Oncogene 13: 2477-2482 (1996); Abarzua et al., Cancer Res. 55:3490-3494 (1995); Halazonetis et al., EMBO J. 12:1021-1028 (1993); Wieczorek et al., Nat. Med. 2: 1143-1146 (1996); Selinova et al., Mol. Cell Biol. 19, 3395-3402 (1999); Peng et al., Oncogene 22: 4478-4487 (2003)). Recently, small molecules and peptides, such as CP-31398, PRIMA1, and CDB3 peptide, have been shown to be effective in restoring p53 function (Foster et al., (1999) Science 286: 2507-2510; Bykov et al., Nat. Med. 8, 282-288 (2002); Friedler et al., Proc. Nat. Acad. Sci. U.S.A. 99, 937-942 (2002); Freidler et al., J. Biol. Chem. 278, 24108-24112 (2003); Issaeva et al., Proc. Nat. Acad. Sci. U.S.A. 100, 13303-13307 (2003); Luu et al., Exp. Cell Res. 276: 214-222 (2002); Wang et al., Mol. Cell Biol. 23, 2171-2181 (2003); Wischhusen et al., Oncogene 22, 8233-8245 (2003); Takimoto et al., Cancer Biol. Ther. 1, 47-55 (2002)).

There exists a need in the art for assay methods by which agonists of p53 function may be quickly and conveniently identified.

SUMMARY OF THE INVENTION

The present invention addresses this need and others, in part, by providing assays and compositions useful for identifying substances that stabilize p53.

The present method provides a method for testing a substance for the presence of an anti-cancer agent or a p53 stabilizer comprising: (a) placing, in an aqueous suspension, a plurality of support particles, impregnated with a fluorescer, to which a p53 polypeptide or a fusion thereof is attached; (b) adding, to the suspension, known, radiolabeled p53-binding substance and a sample to be tested for the presence of the agent or stabilizer, wherein the radiolabel emits radiation energy capable of activating the fluorescer upon the binding of the binding substance to the p53 polypeptide or a fusion thereof to produce light energy, whereas radiolabeled p53-binding substance that does not bind to the polypeptide is, generally, too far removed from the support particles to enable the radioactive energy to activate the fluorescer; and (c) measuring the light energy emitted by the fluorescer in the suspension; wherein an anti-cancer agent or a p53 stabilizer in the sample is identified by measuring substantially reduced light energy emission, compared to what would be measured in the absence of such an antagonist. In an embodiment of the invention, the fluorescer is selected from the group consisting of yttrium silicate, yttrium oxide, diphenyloxazole and polyvinyltoluene. In an embodiment of the invention, the p53-binding substance is labeled with a radiolabel selected from the group consisting of $^3$H and $^{125}$I. In an embodiment of the invention, the known p53-binding substance is a member selected from the group consisting of:

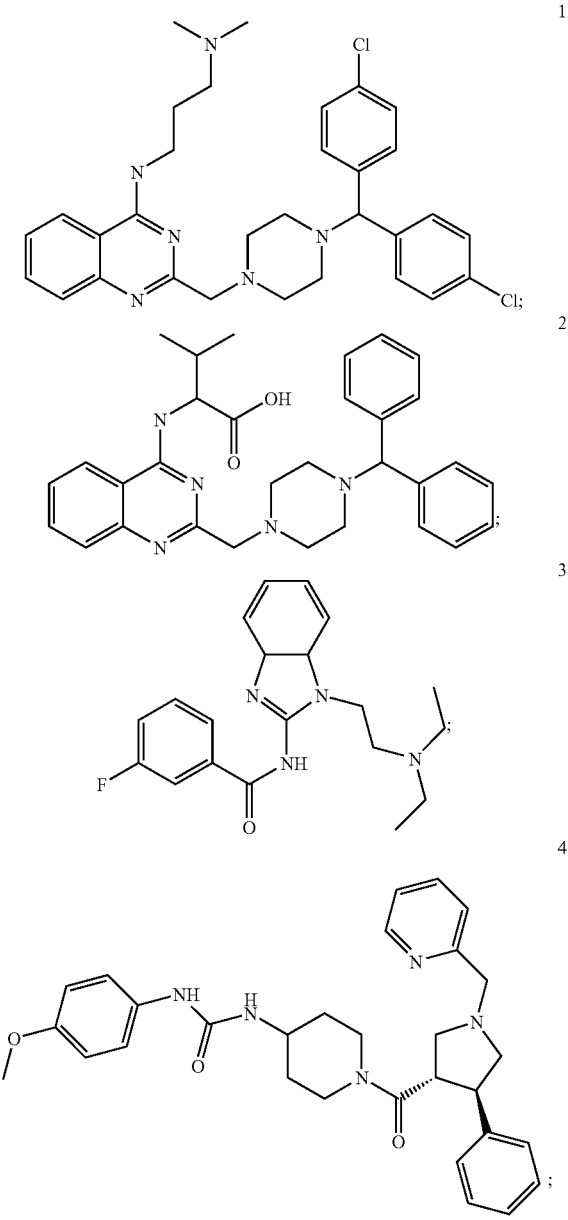

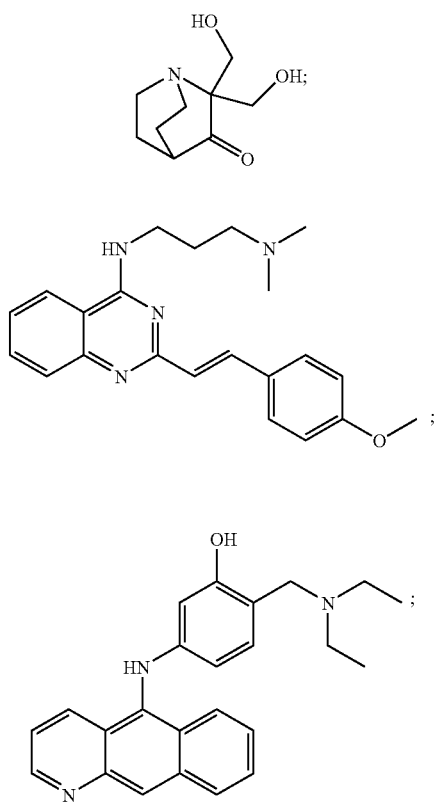
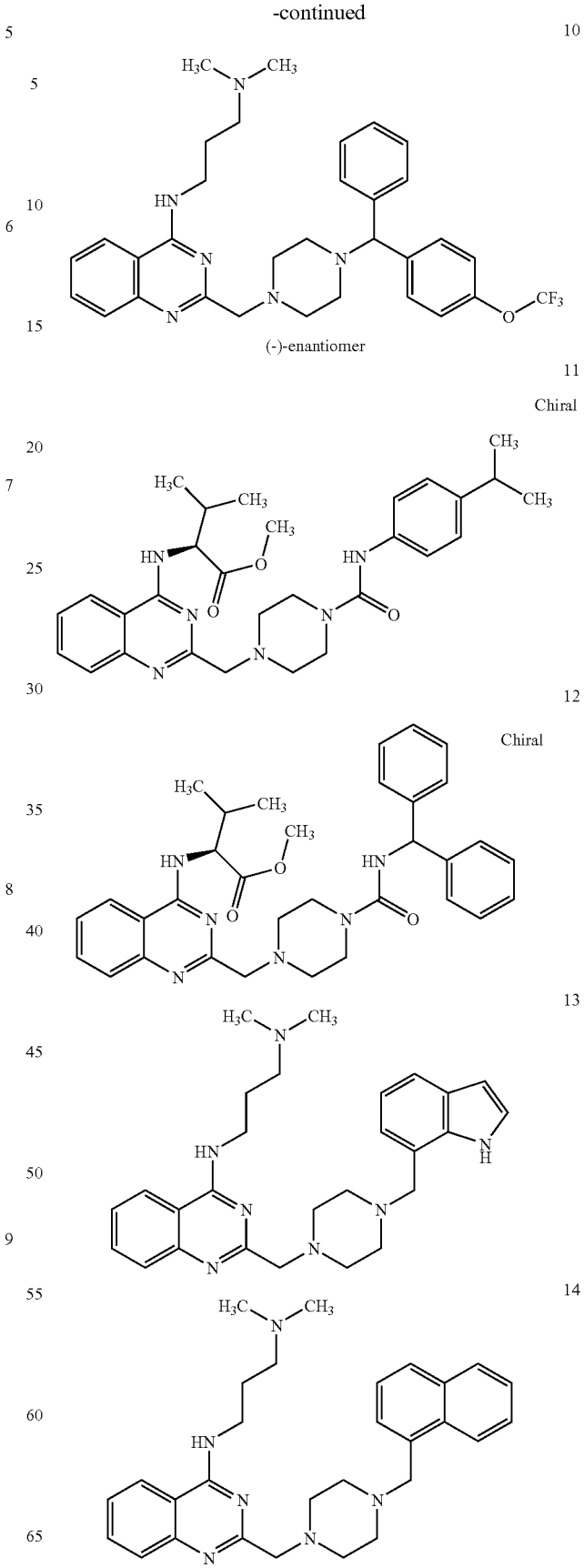
a polypeptide comprising the amino acid sequence REDEDEIEW-NH₂ (SEQ ID NO:3);

15
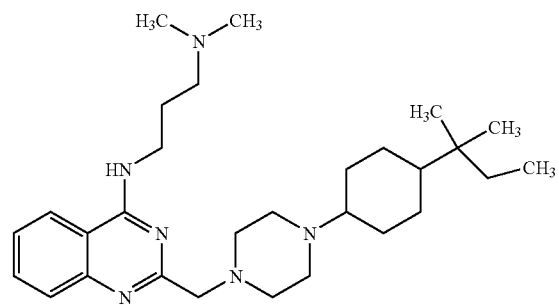
16
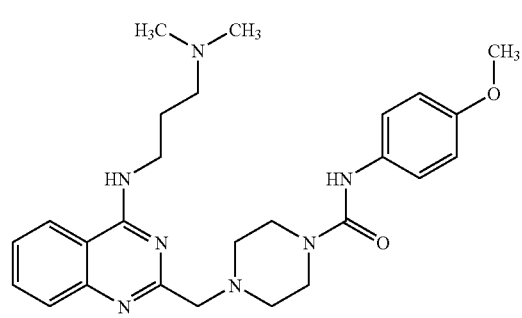
17
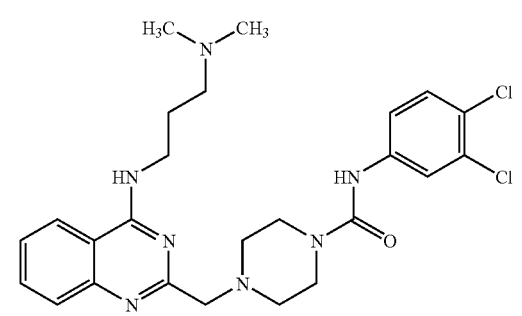
18
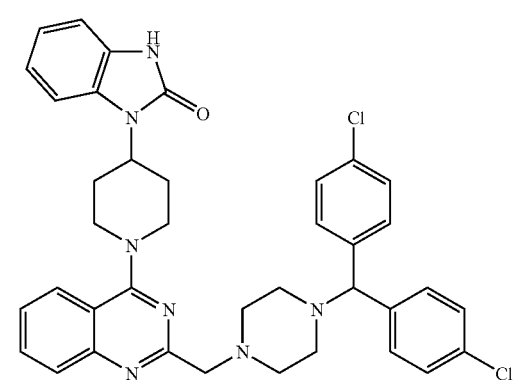
19
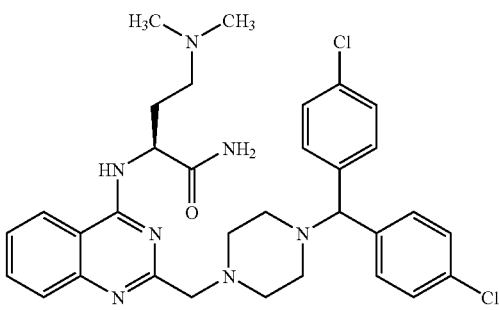
20
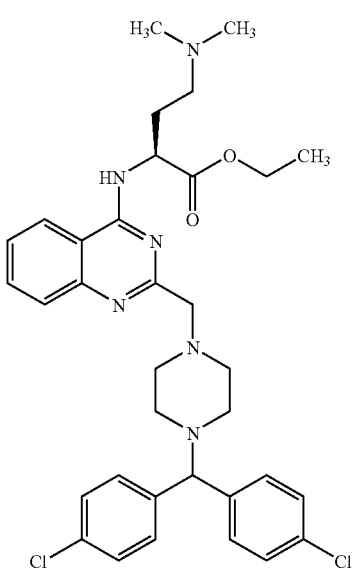
21
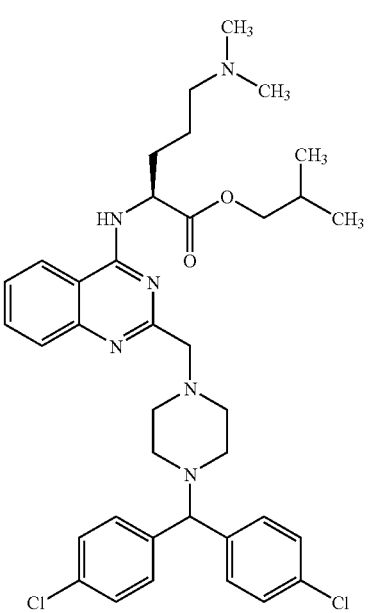

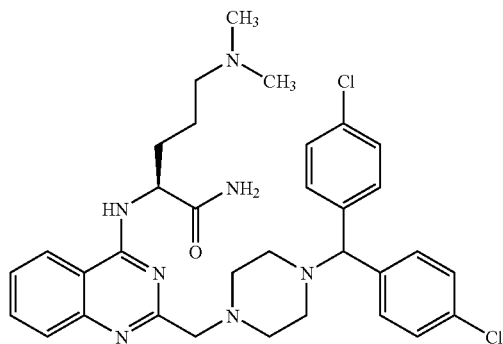
22
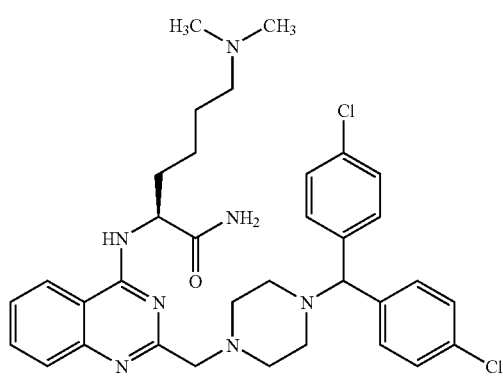
23
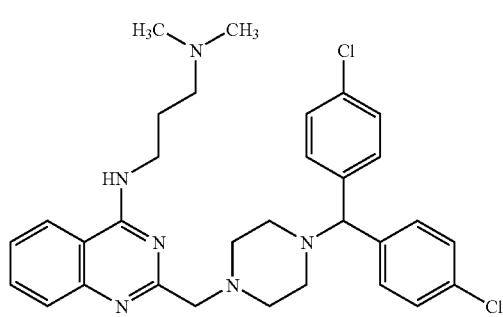
24
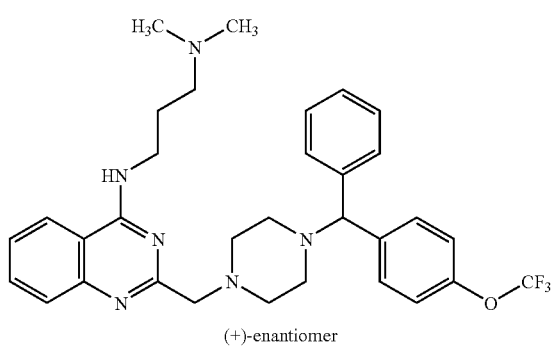
25
(+)-enantiomer
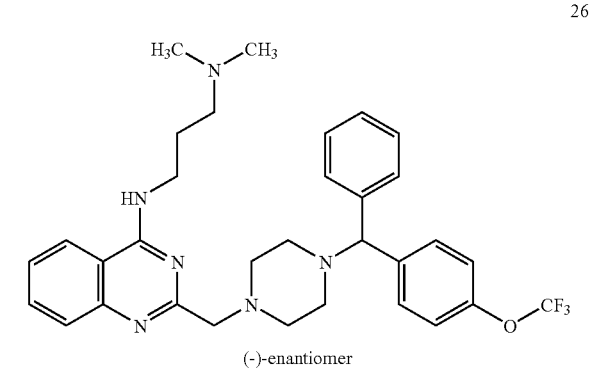
26
(−)-enantiomer
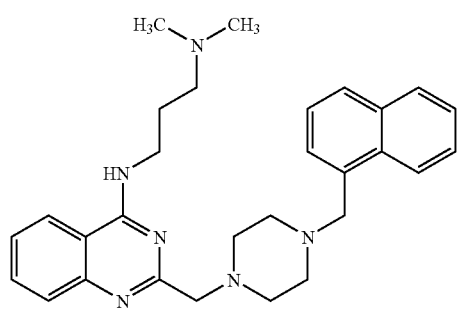
27
28
29

-continued

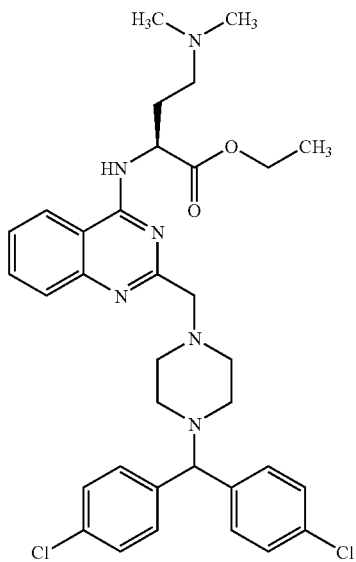
30

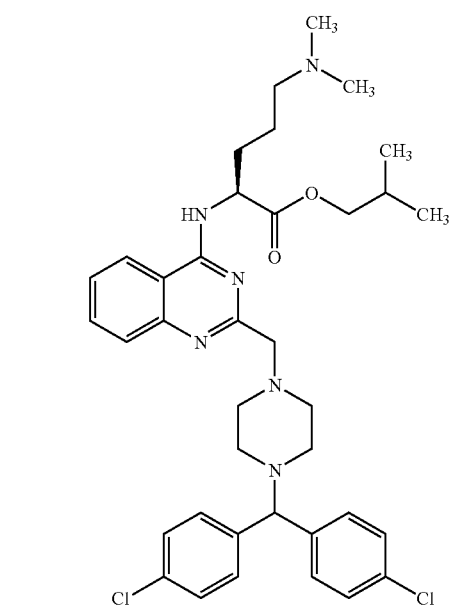
31

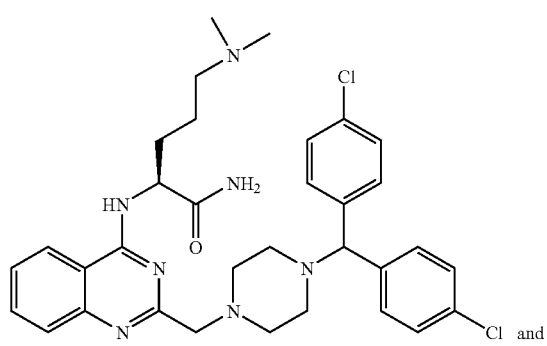
32 and

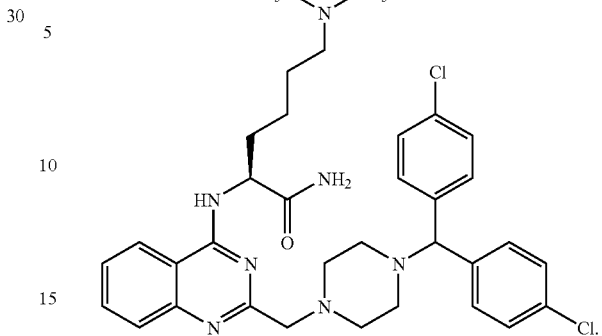
33

In an embodiment of the invention, the substance is any of the p53 binding substances set forth herein (e.g., any of compounds 1-119).

In an embodiment of the invention, the p53 polypeptide comprises the amino acid sequence of SEQ ID NO: 2 or amino acids 92-312 of SEQ ID NO: 2, optionally comprising one or more mutations selected from the group consisting of: R273H, R249S, R175H, R175P, R175C, S389A, R181C, R181H, R181L, R213H, S241F, G245V, G245S, R248Q, R248W, R249S, R273C, R273H and R273P.

The present invention provides a method for testing a substance for the presence of an anti-cancer agent or a p53 stabilizer comprising: (a) contacting p53 mutant polypeptide with a substance to be tested for the agent or stabilizer and with a polynucleotide comprising a p53 consensus sequence under conditions such that a wild-type p53 would bind to the polynucleotide; and (b) determining if the p53 mutant polypeptide binds to the polynucleotide; wherein the substance is determined to contain the agent or stabilizer if the p53 mutant polypeptide binds to the polynucleotide. In an embodiment of the invention, the p53 mutant polypeptide comprises the amino acid sequence of SEQ ID NO: 2 or amino acids 92-312 of SEQ ID NO: 2 comprising one or more mutations selected from the group consisting of: R273H, R249S, R175H, R175P, R175C, S389A, R181C, R181H, R181L, R213H, G245V, G245S, R248Q, R248W, R249S, R273C, R273H and R273P. In an embodiment of the invention, the polynucleotide comprises the nucleotide sequence AGCTGGACATGCCCGGGCATGTCC (SEQ ID NO: 4). In an embodiment of the invention, binding of the p53 mutant polypeptide to the polynucleotide is determined by determining if the polynucleotide migrates, under an electric gradient, through a gel matrix slower than a polynucleotide that has not been contacted with the p53 mutant polypeptide. In an embodiment of the invention, the gel matrix comprises agarose or polyacrylamide.

The present invention provides a method for testing a substance for the presence of an anti-cancer agent or a p53 stabilizer comprising: (a) contacting p53 polypeptide, in the presence of a known amount of known p53-binding substance, with a sample to be tested for the presence of said agent or stabilizer; and (b) measuring the amount of the known p53-binding substance specifically bound to the p53 polypeptide; whereby the sample is identified as containing the agent or stabilizer by measuring substantially reduced binding of the known p53-binding substance to the p53 polypeptide, compared to what would be measured in the absence of the sample. In an embodiment of the invention, the p53 polypeptide comprises the amino acid sequence of SEQ ID NO: 2 or amino acids 92-312 of SEQ ID NO: 2, optionally comprising one or more mutations selected from the group consisting of: R273H, R249S, R175H, R175P, R175C, S389A, R181C, R181H, R181L, R213H, G245V, G245S, R248Q, R248W, R249S, R273C, R273H and R273P. In an embodiment of the invention, the known p53-binding substance is detectably labeled. In an embodiment of the invention, the detectable label is selected from the group consisting of $^3H$, $^{131}I$, $^{35}S$, $^{32}P$ and $^{14}C$. In an embodiment of the invention, the p53-binding substance is a represented by a structural formula selected from the group consisting of:

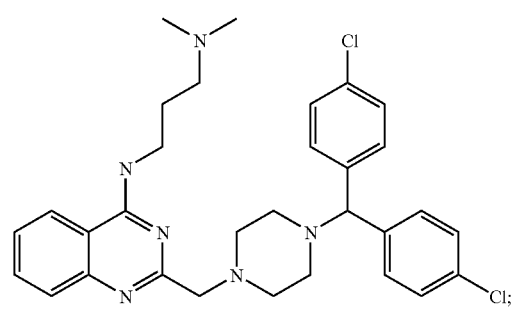

1

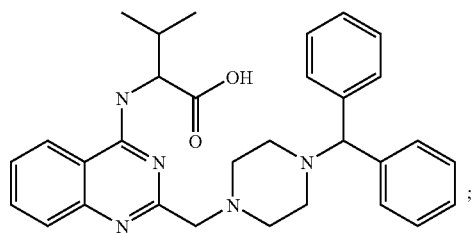

2

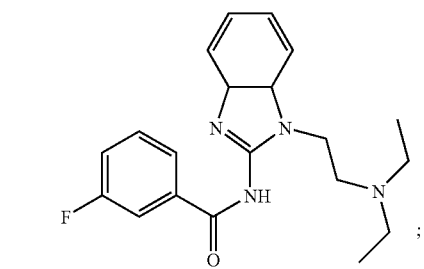

3

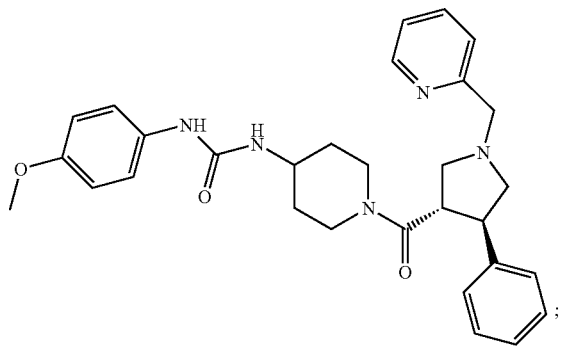

4

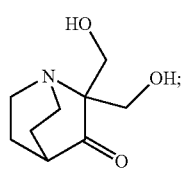

5

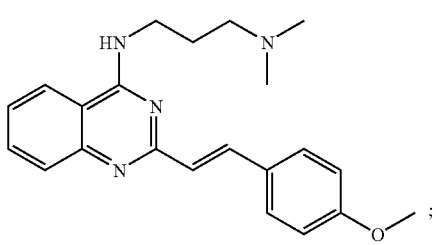

6

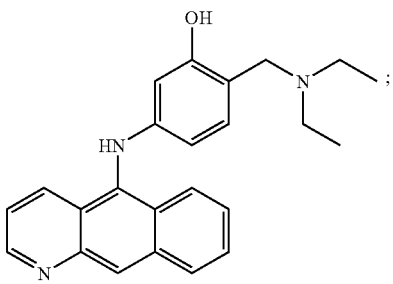

7 a polypeptide comprising the amino acid sequence REDEDEIEW-NH$_2$ (SEQ ID NO:3);

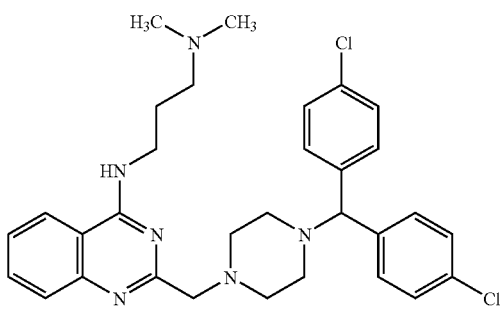

8

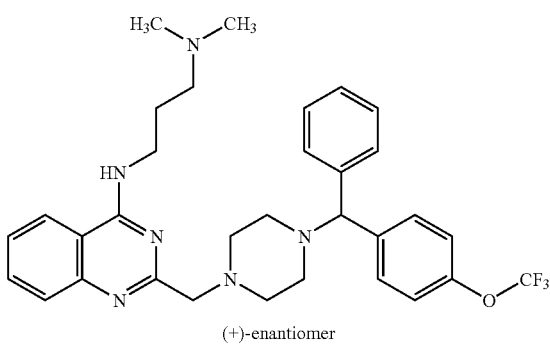

9
(+)-enantiomer

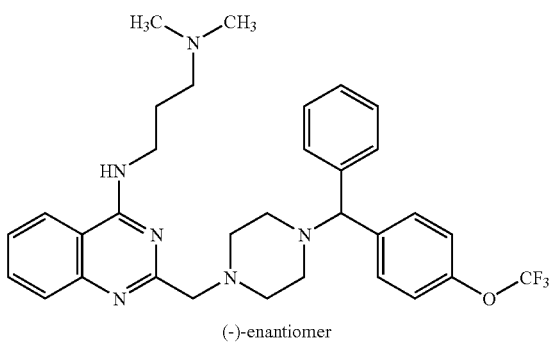

10
(-)-enantiomer

-continued
11
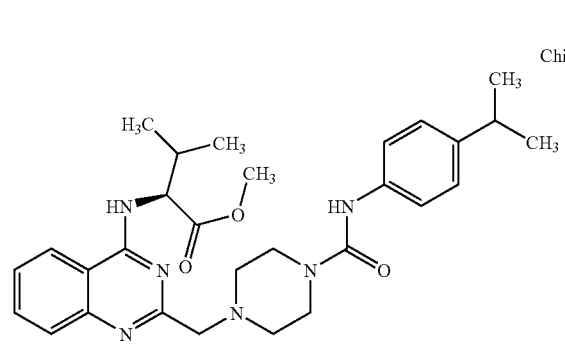
12
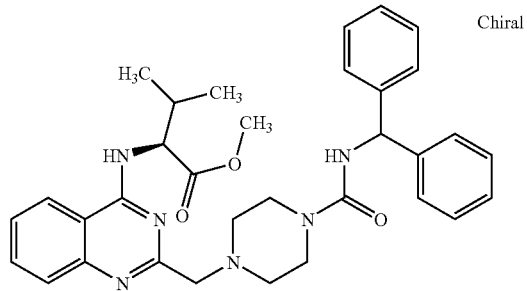
13
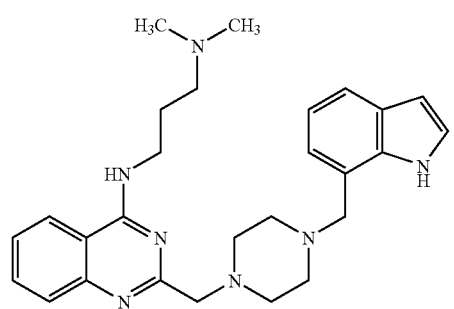
14
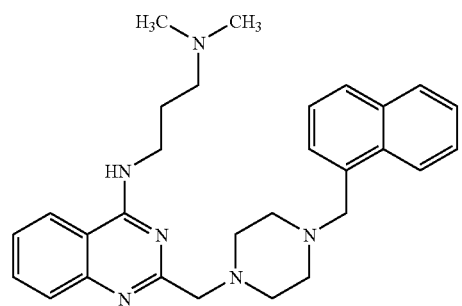
15
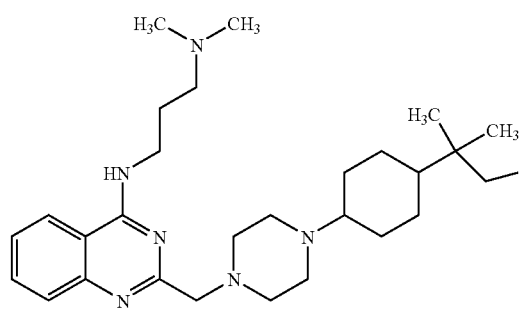
-continued
16
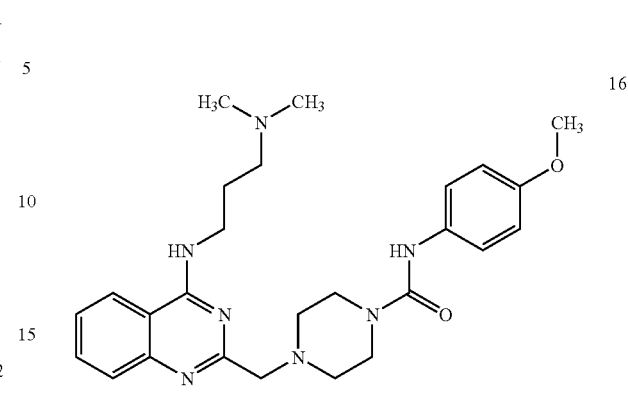
17
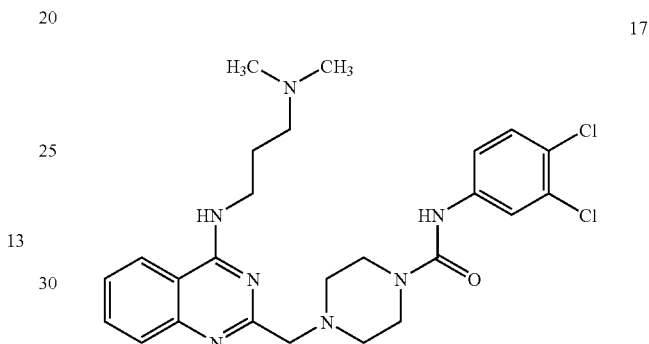
18
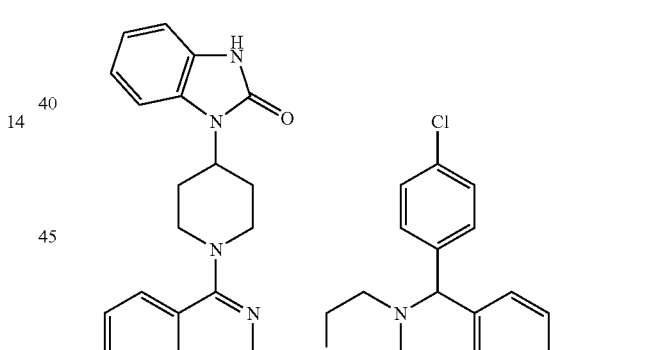
19
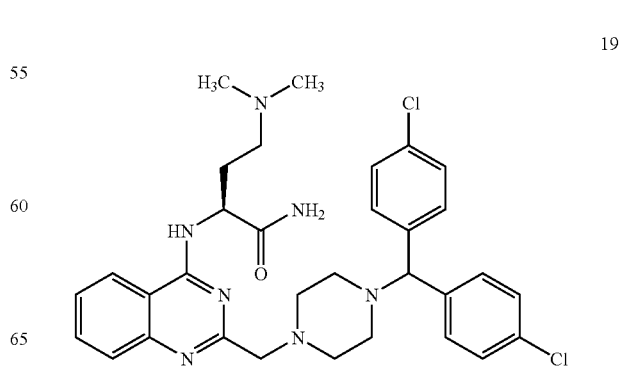

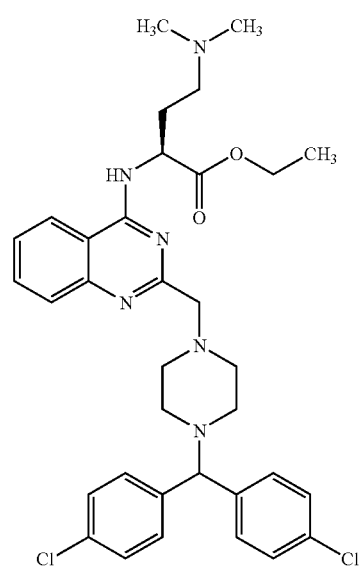
20
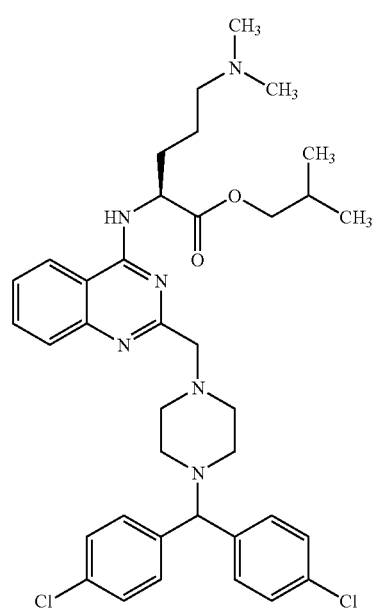
21
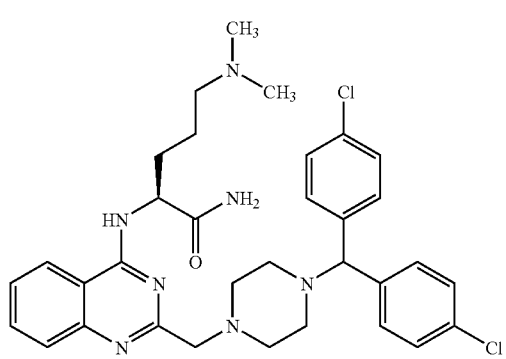
22
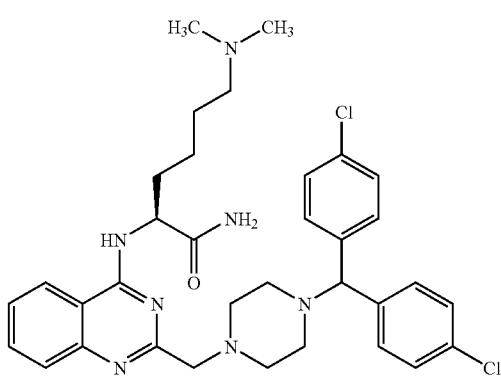
23
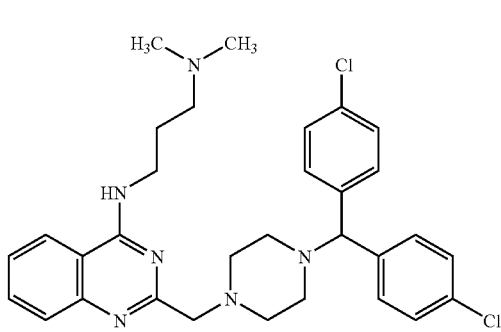
24
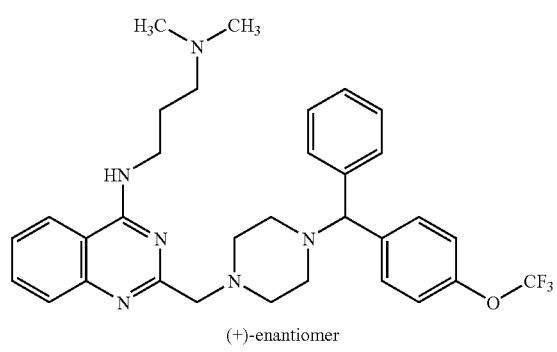
25
(+)-enantiomer
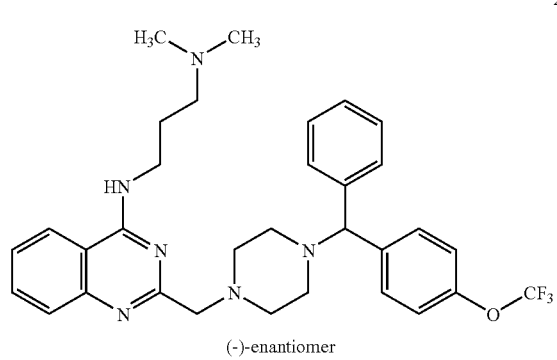
26
(−)-enantiomer

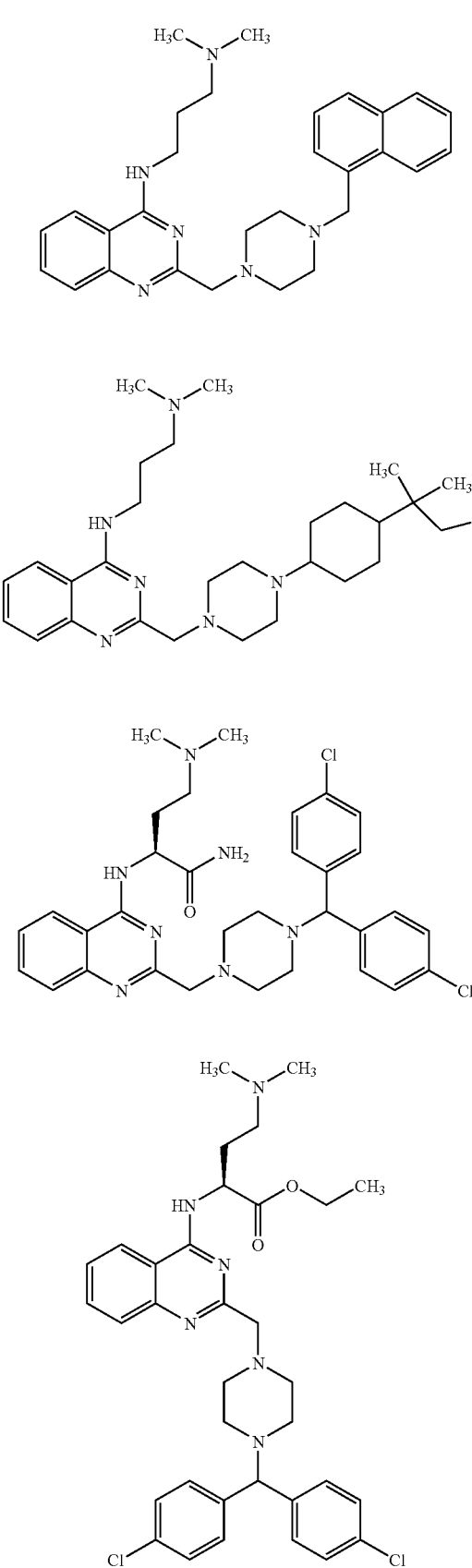

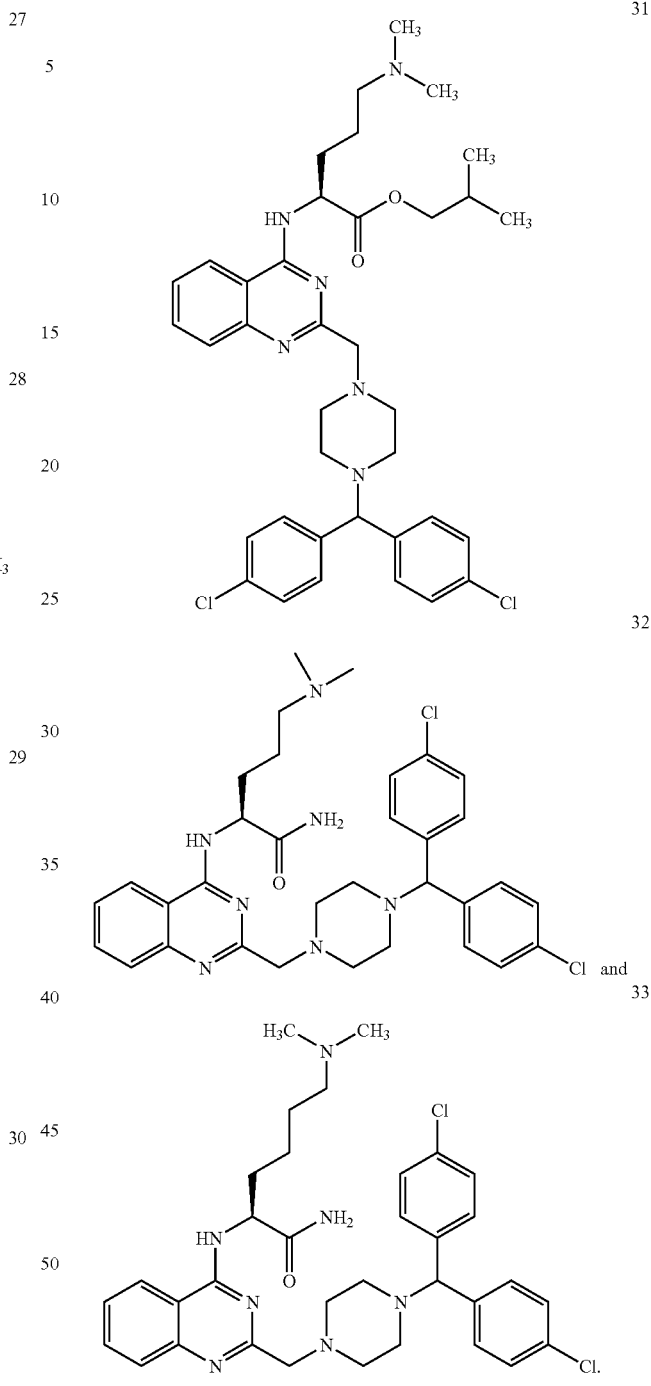

The present invention provides a method for testing a substance for the presence of an anti-cancer agent or a p53 stabilizer comprising: (a) administering the substance to a xenograft mammal comprising tumor cells comprising p53 mutant polypeptide; and (b) measuring tumor volume and/or growth rate over time; wherein the substance is determine to contain the agent or stabilizer if tumor volume or growth rate decreases over time or increases over time at a lower rate than that of a mammal which has not been contacted with the substance. In an embodiment of the invention, the mammal is a mouse. In an embodiment of the invention, the p53 mutant polypeptide comprises the amino acid sequence of SEQ ID NO: 2 comprising one or more mutations selected from the group consisting of: R273H, R249S, R175H, R175P, R175C, S389A, R181C, R181H, R181L, R213H, G245V, G245S, R248Q, R248W, R249S, R273C, R273H and R273P.

The present invention provides a method for testing a substance for the presence of an anti-cancer agent or a p53 stabilizer comprising: (a) contacting a cell comprising mutant p53 polypeptide with a substance to be tested for the presence of the agent or stabilizer; and (b) measuring cell growth over time; wherein the substance is determine to contain the agent or stabilizer if the cell growth rate decreases over time or increases over time at a lower rate than that of a cell which has not been contacted with the substance. In an embodiment of the invention, the cell is in vitro. In an embodiment of the invention, the p53 mutant polypeptide comprises the amino acid sequence of SEQ ID NO: 2 comprising one or more mutations selected from the group consisting of: R273H, R249S, R175H, R175P, R175C, S389A, R181C, R181H, R181L, R213H, G245V, G245S, R248Q, R248W, R249S, R273C, R273H and R273P.

The present invention provides a method for testing a substance for the presence of an anti-cancer agent or a p53 stabilizer comprising: (a) contacting a polynucleotide comprising a p53-binding sequence on a surface of a sensor chip with mutant p53 polypeptide and with a substance to be tested for the presence of the agent or stabilizer under conditions that permit a wild-type p53 polypeptide to bind the coating; and (b) detecting the change in surface plasmon resonance signal of the sensor chip resulting from the mutant p53 polypeptide binding to the polynucleotide coating; wherein the substance is determine to contain the agent or stabilizer if the surface plasmon resonance change is detected relative to binding of the polypeptide to the polynucleotide coating in the absence of said substance. In an embodiment of the invention, the p53 mutant polypeptide comprises the amino acid sequence of SEQ ID NO: 2 or amino acids 92-312 of SEQ ID NO: 2, comprising one or more mutations selected from the group consisting of: R273H, R249S, R175H, R175P, R175C, S389A, R181C, R181H, R181L, R213H, G245V, G245S, R248Q, R248W, R249S, R273C, R273H and R273P. In an embodiment of the invention, the polynucleotide comprise the nucleotide sequence AGCTGGACATGCCCGGGCATGTCC (SEQ ID NO: 4).

The present invention provides a viral vector comprising a polynucleotide encoding a stabilized allele of p53. In an embodiment of the invention, the allele encodes the amino acid sequence of SEQ ID NO: 1 comprising the N268R mutation. In an embodiment of the invention, the virus is an adenovirus. The present invention further provides a viral particle comprising the vector along with an isolated host cell (e.g., A549 cell) comprising the vector. In an embodiment of the invention, the host cell comprises: (1) (a) a first nucleic acid molecule comprising a nucleotide sequence encoding adenoviral E1A proteins deficient in binding to p300 protein family members and pRb protein family members; and (b) a second nucleic acid molecule comprising a nucleotide sequence encoding an adenoviral E1B-55K protein; or (2) (a) a first expression cassette comprising a promoter active in said human cell operably linked to a nucleic acid sequence encoding adenoviral E1A proteins deficient in binding to p300 protein family members and pRb protein family members, wherein said proteins are expressed in said human cell; and (b) a second expression cassette comprising a promoter active in said human cell operably linked to a nucleic acid sequence encoding an adenoviral E1B protein, wherein said E1B protein comprises an E1B-55K protein but not an E1B-19K protein, wherein said E1B-55K protein is expressed in said human cell.

The present invention provides a method for treating or preventing cancer, in a subject, comprising administering a therapeutically effective amount of the vector. In an embodiment of the invention, the cancer is selected from the group consisting of neuroblastoma, rhabdomyosarcoma, osteosarcoma, acromegaly, ovarian cancer, pancreatic cancer, benign prostatic hyperplasia, breast cancer, prostate cancer, bone cancer, lung cancer, colorectal cancer, cervical cancer, synovial sarcoma, bladder cancer, Wilm's cancer, ovarian cancer, benign prostatic hyperplasia (BPH), diarrhea associated with metastatic carcinoid and vasoactive intestinal peptide secreting tumors, VIPoma, Werner-Morrison syndrome, kidney cancer, renal cell carcinoma, transitional cell cancer, Ewing Sarcoma, leukemia, acute lymphoblastic leukemia, brain cancer, glioblastoma, non-glioblastoma brain cancer, meningioma, pituitary adenoma, vestibular schwannoma, a primitive neuroectodermal tumor, medulloblastoma, astrocytoma, oligodendroglioma, ependymoma and choroid plexus papilloma.

The present invention provides an isolated polynucleotide comprising the nucleotide sequence of SEQ ID NO: 1 or nucleotides 274-936 thereof wherein nucleotides 802-804 encode arginine; along with a recombinant vector comprising the polynucleotide (e.g., operably linked to an expression control element such as a promoter); along with an isolated host cell comprising the vector.

The present invention also provides an isolated polypeptide comprising the amino acid sequence of SEQ ID NO: 2 or amino acids 92-312 thereof wherein amino acid 268 is arginine. In an embodiment of the invention, the polypeptide is fused to a heterologous protein (e.g., GST). Also provided by the invention is a method for making the polypeptide comprising introducing a polynucleotide encoding said polypeptide into a host cell under conditions that allow expression of said polypeptide and isolating the polypeptide from the cell.

DETAILED DESCRIPTION OF THE INVENTION

Assays of the present invention can be used to identify therapeutic agents that are useful for treating or preventing cancer. The present invention includes assays for identifying substances that stabilize and restore the function of mutated p53. These substances can be administered to a subject to prevent or treat the occurrence of various types of cancer. Without being bound by a single theory or mechanism of action, the substances identified by the present invention may treat or prevent the occurrence of cancer by causing, directly or indirectly, an increase in p53 activity in the subject's body which, in turn, leads to an functions that are related to p53, including, for example, DNA repair, cell cycle arrest or apoptosis.

The term "p53" is commonly known in the art as is its amino acid sequence and nucleotide sequence. In an embodiment, a p53 polypeptide comprises the amino acid sequence:

(SEQ ID NO: 2)
MEEPQSDPSVEPPLSQETFSDLWKLLPENNVLSPLPSQAMDDLMLSPDDI

EQWFTEDPGPDEAPRMPEAAPPVAPAPAAPTPAAPAPAPSWPLSSSVPSQ

KTYQGSYGFRLGFLHSGTAKSVTCTYSPALNKMFCQLAKTCPVQLWVDST

PPPGTRVRAMAIYKQSQHMTEVVRRCPHHERCSDSDGLAPPQHLIRVEGN

-continued

```
LRVEYLDDRNTFRHSVVVPYEPPEVGSDCTTIHYNYMCNSSCMGGMNRRP

ILTIITLEDSSGNLLGRNSFEVRVCACPGRDRRTEEENLRKKGEPHHELP

PGSTKRALPNNTSSSPQPKKKPLDGEYFTLQIRGRERFEMFRELNEALEL

KDAQAGKEPGGSRAHSSHLKSKKGQSTSRHKKLMFKTEGPDSD
```

In an embodiment, a p53 polynucleotide or gene comprises the nucleotide sequence:

(SEQ ID NO: 1)
```
ATGGAGGAGCCGCAGTCAGATCCTAGCGTCGAGCCCCCTCTGAGTCAGGA

AACATTTTCAGACCTATGGAAACTACTTCCTGAAAACAACGTTCTGTCCC

CCTTGCCGTCCCAAGCAATGGATGATTTGATGCTGTCCCCGGACGATATT

GAACAATGGTTCACTGAAGACCCAGGTCCAGATGAAGCTCCCAGAATGCC

AGAGGCTGCTCCCCCCGTGGCCCCTGCACCAGCAGCTCCTACACCGGCGG

CCCCTGCACCAGCCCCCTCCTGGCCCCTGTCATCTTCTGTCCCTTCCCAG

AAAACCTACCAGGGCAGCTACGGTTTCCGTCTGGGCTTCTTGCATTCTGG

GACAGCCAAGTCTGTGACTTGCACGTACTCCCCTGCCCTCAACAAGATGT

TTTGCCAACTGGCCAAGACCTGCCCTGTGCAGCTGTGGGTTGATTCCACA

CCCCCGCCCGGCACCCGCGTCCGCGCCATGGCCATCTACAAGCAGTCACA

GCACATGACGGAGGTTGTGAGGCGCTGCCCCCACCATGAGCGCTGCTCAG

ATAGCGATGGTCTGGCCCCTCCTCAGCATCTTATCCGAGTGGAACGAAAT

TTGCGTGTGGAGTATTTGGATGACAGAAACACTTTTCGACATAGTGTGGT

GGTGCCCTATGAGCCGCCTGAGGTTGGCTCTGACTGTACCACCATCCACT

ACAACTACATGTGTAACAGTTCCTGCATGGGCGGCATGAACCGGAGGCCC

ATCCTCACCATCATCACACTGGAAGACTCCAGTGGTAATCTACTGGGACG

GAACAGCTTTGAGGTGCGTGTTTGTGCCTGTCCTGGGAGAGACCGGCGCA

CAGAGGAAGAGAATCTCCGCAAGAAAGGGGAGCCTCACCACGAGCTGCCC

CCAGGGAGCACTAAGCGAGCACTGCCCAACAACACCAGCTCCTCTCCCCA

GCCAAAGAAGAAACCACTGGATGGAGAATATTTCACCCTTCAGATCCGTG

GGCGTGAGCGCTTCGAGATGTTCCGAGAGCTGAATGAGGCCTTGGAACTC

AAGGATGCCCAGGCTGGGAAGGAGCCAGGGGGGAGCAGGGCTCACTCCAG

CCACCTGAAGTCCAAAAAGGGTCAGTCTACCTCCCGCCATAAAAAACTCA

TGTTCAAGACAGAAGGGCCTGACTCAGACTGA
```

The term "p53 mutant" or the like refers to a p53 polypeptide or polynucleotide comprising any mutation. For example, in an embodiment, the term "p53 mutant polypeptide" includes one or more of the following mutations: R273H, R249S, R175H, R175P, R175C, S389A, R181C, R181H, R181L, R213H, S241F, G245V, G245S, R248Q, R248W, R249S, R273C, R273H, R273P (wherein the first letter denotes the wild-type amino acid at the position indicated and the second letter denotes the mutant amino acid at the position indicated) or any mutation that occurs at a p53 mutational hotspot, such as 132K, 135C, 138A, 146W, 151P, 152P, 154G, 155T, 156R, 157V, 158R, 159A, 161A, 163Y, 173V, 174R, 175R, 176C, 177P, 179H, 192Q, 193H, 194L, 195I, 196R, 205Y, 213R, 216V, 220Y, 234Y, 236Y, 237M, 238C, 239N, 241S, 242C, 244G, 245G, 246M, 248R, 249R, 250P, 258E, 266G, 272V, 273R, 275C, 278P, 280R, 281D, 282R, 283R, 285E, 286E or 306R (i.e., wherein the amino acid at the indicated position is any one other than that shown)

The term "p53 polypeptide" includes wild-type full length p53, any fragment thereof, including the DNA binding domain of p53 (e.g., amino acids 92-312 of SEQ ID NO: 2) and any fusion thereof (e.g., GST-p53 or GST-p53 DNA binding domain).

There are many substances known in the art to bind to or modulate p53; a practitioner of ordinary skill in the art would know the identity of such substances. In an embodiment of the invention, such a substance is any compound represented by any of structural formulas 1-119, for example:

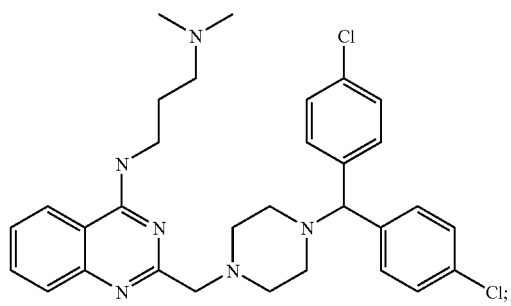

1

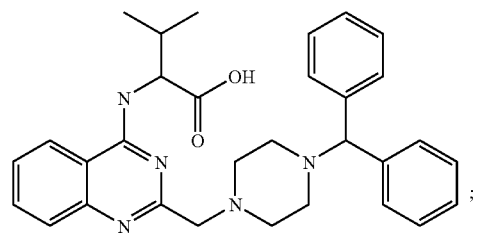

2

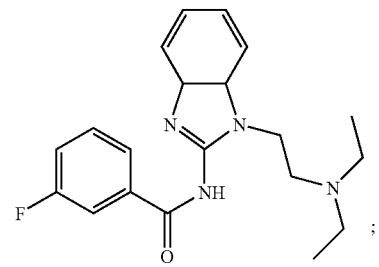

3

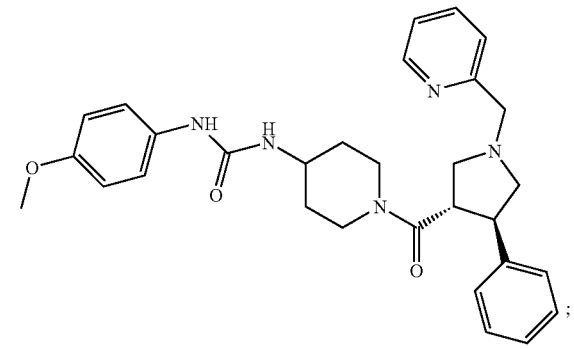

4

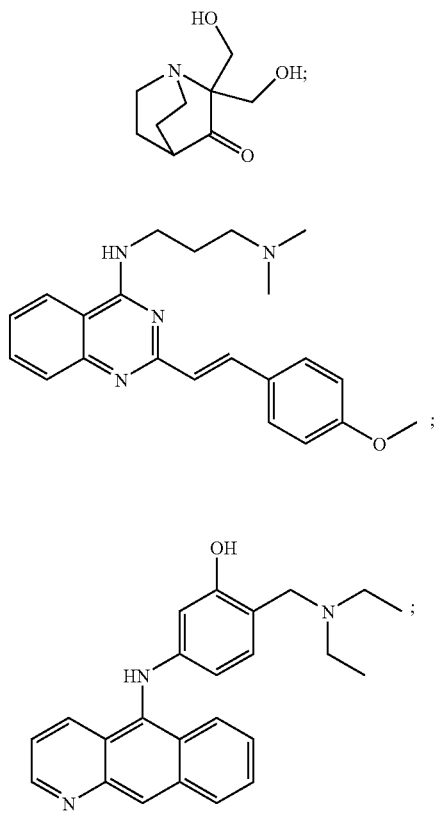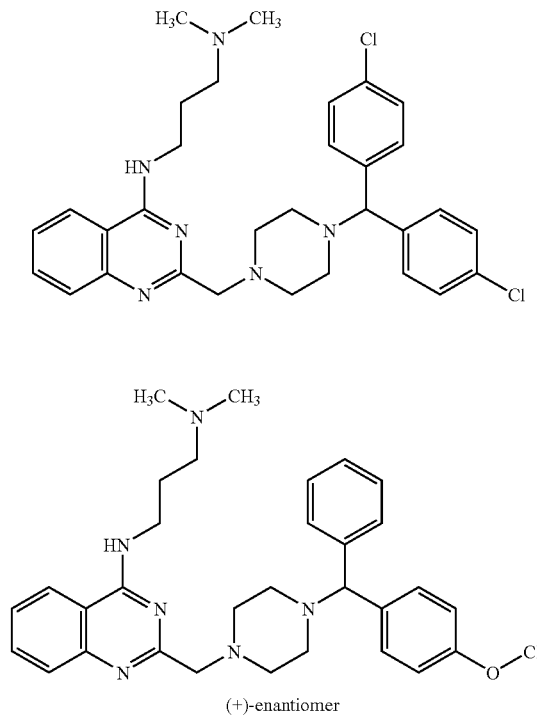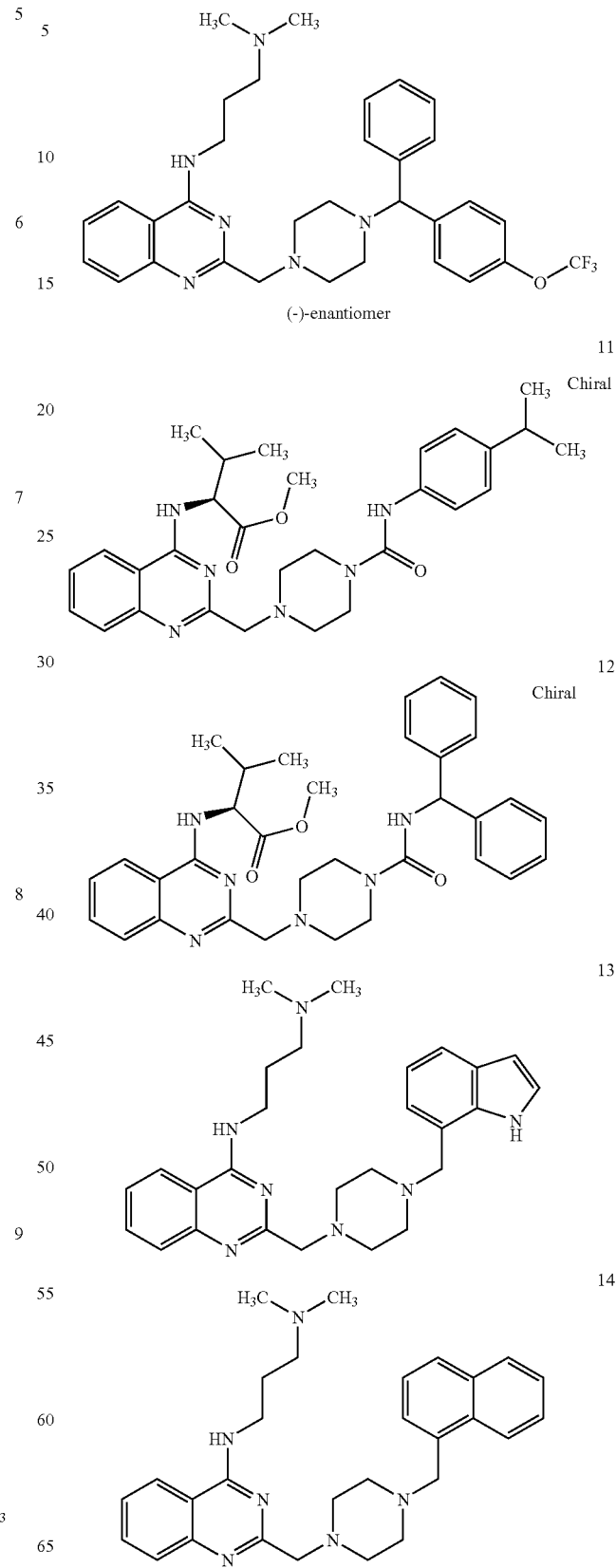
a polypeptide comprising the amino acid sequence REDEDEIEW-NH₂ (SEQ ID NO:3);
(+)-enantiomer
(-)-enantiomer 15
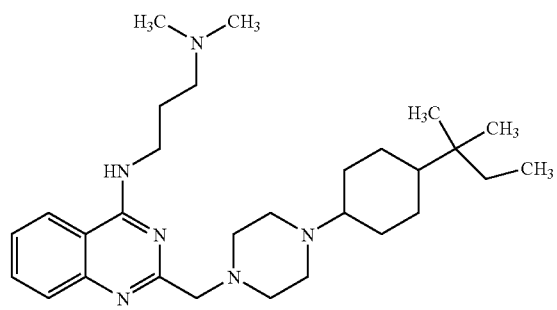
16
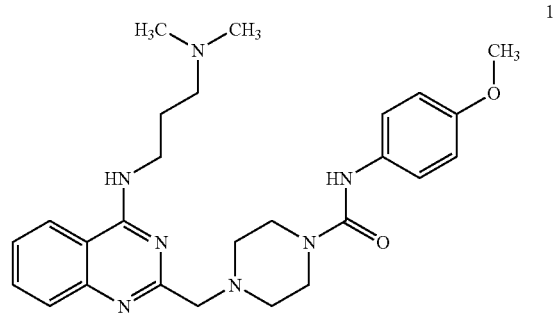
17
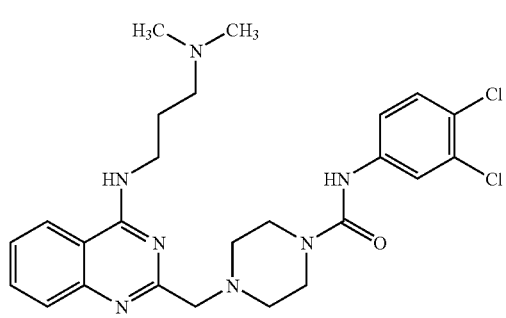
18
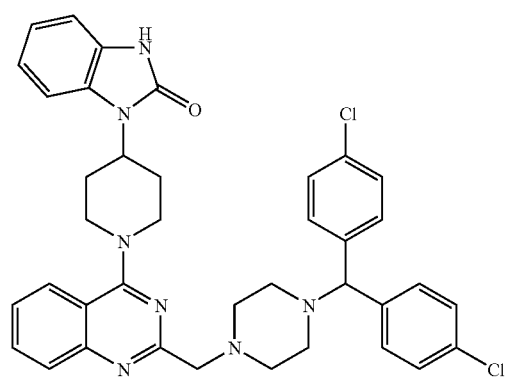
5
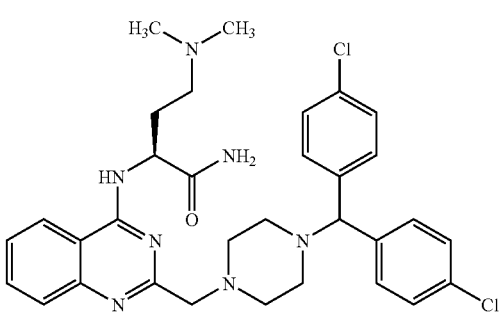
20
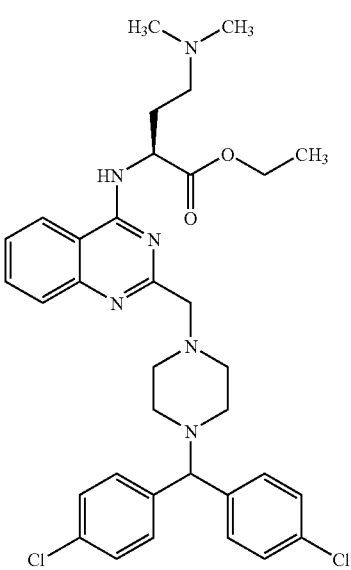
21
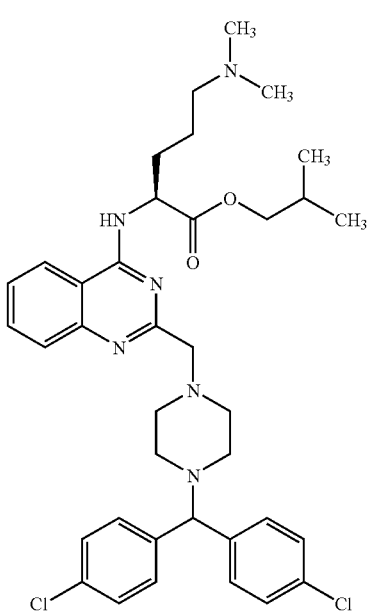

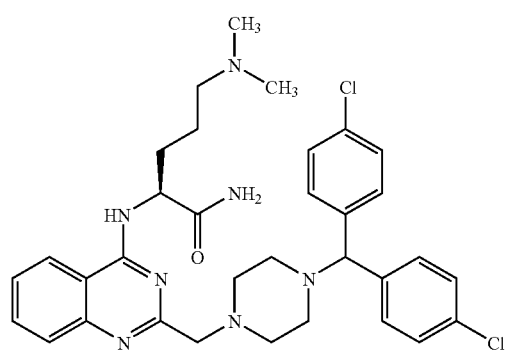
22
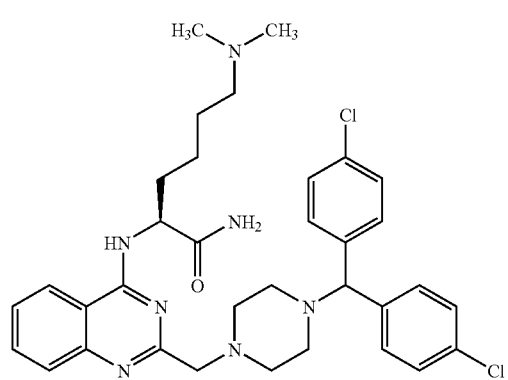
23
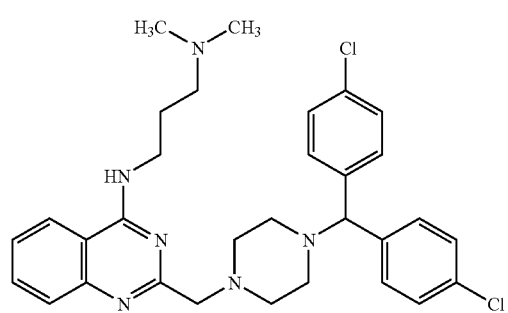
24
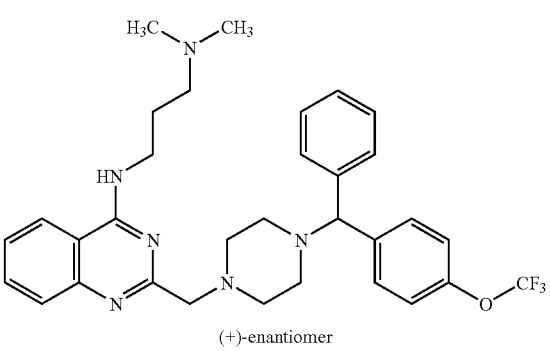
25
(+)-enantiomer
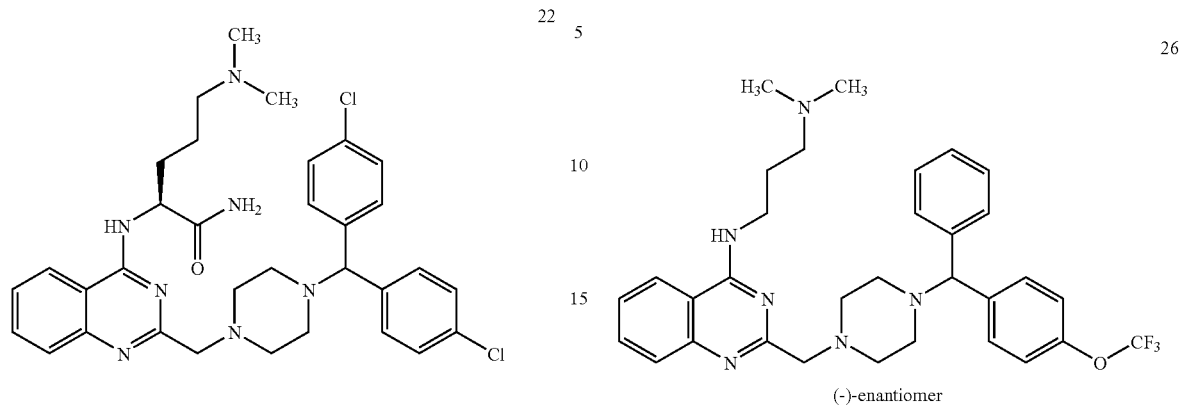
26
(−)-enantiomer
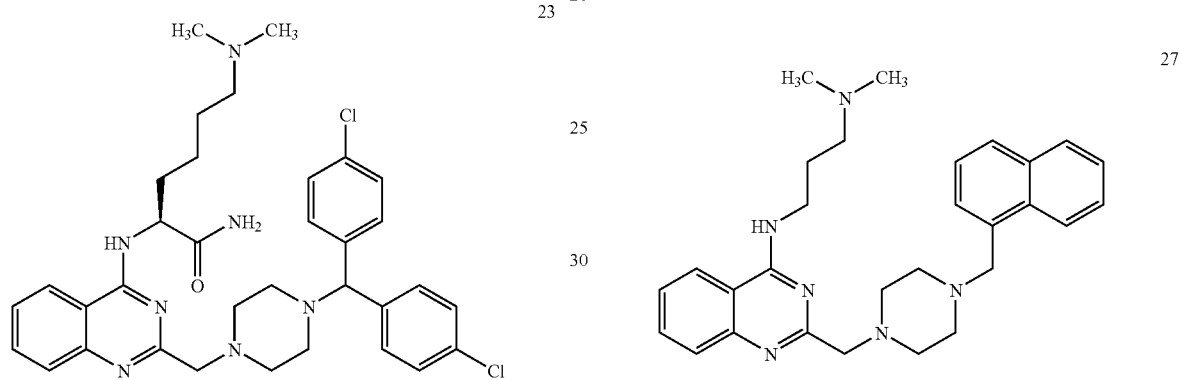
27
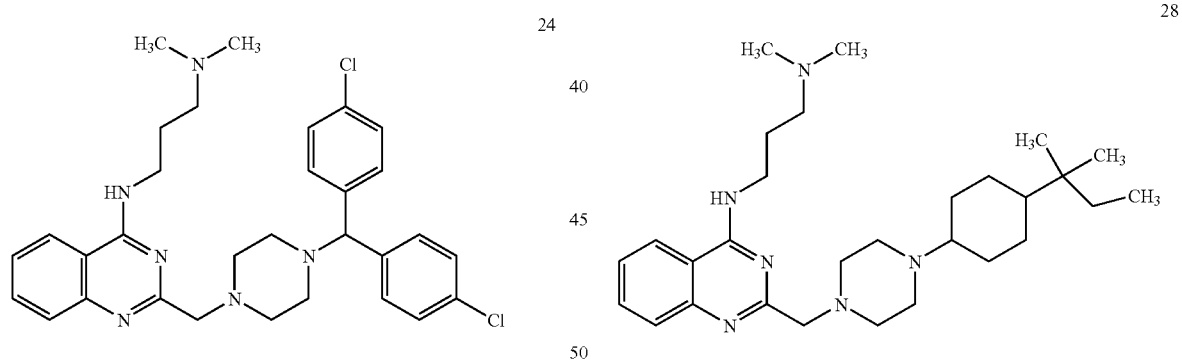
28
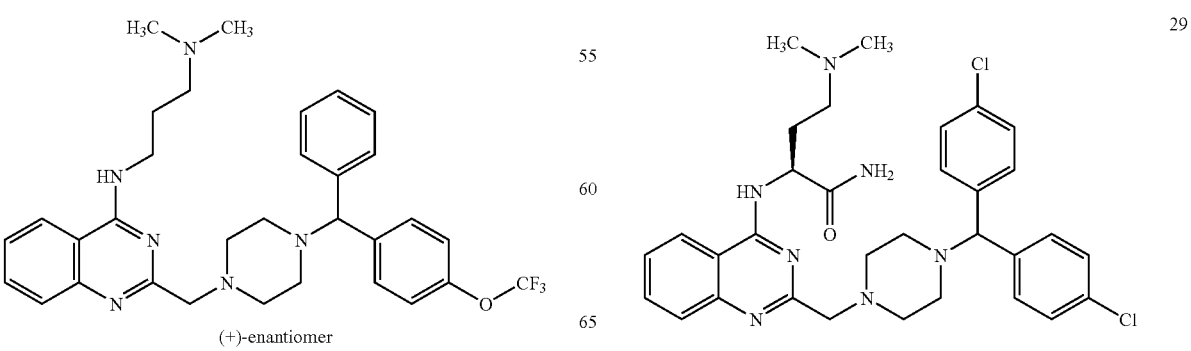
29

-continued

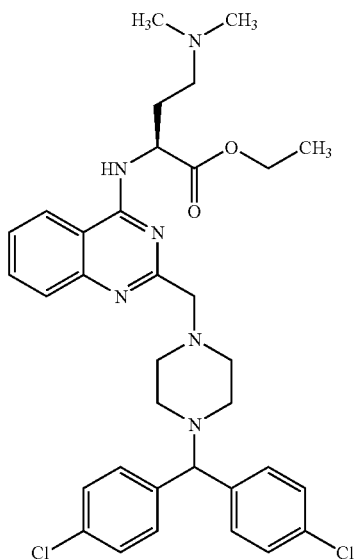
30

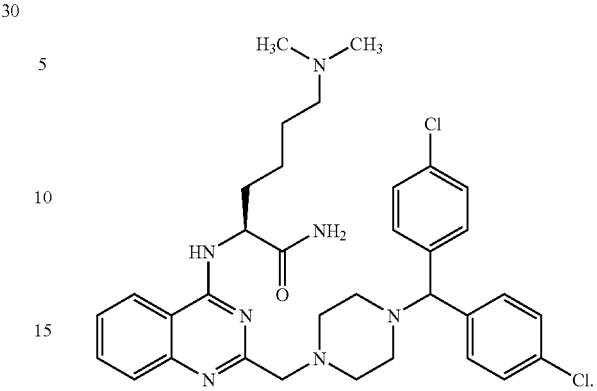
33

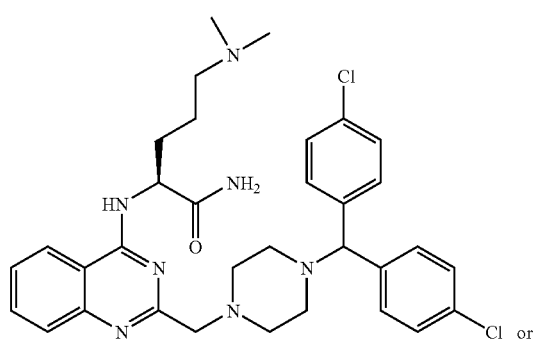
31

32

Cl or

Methods comprising use of such compounds as well as radio-labeled derivatives thereof form part of the present invention. Such methods are discussed in detail herein.

Molecular Biology

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook, et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* (B. D. Hames & S. J. Higgins eds. (1985)); *Transcription And Translation* (B. D. Hames & S. J. Higgins, eds. (1984)); *Animal Cell Culture* (R. I. Freshney, ed. (1986)); *Immobilized Cells And Enzymes* (IRL Press, (1986)); B. Perbal, *A Practical Guide To Molecular Cloning* (1984); F. M. Ausubel, et al. (eds.), *Current Protocols in Molecular Biology*, John Wiley & Sons, Inc. (1994).

A "polynucleotide", "nucleic acid" or "nucleic acid molecule" may refer to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in single stranded form, double-stranded form or otherwise.

A "polynucleotide sequence", "nucleic acid sequence" or "nucleotide sequence" is a series of nucleotide bases (also called "nucleotides") in a nucleic acid, such as DNA or RNA, and means any chain of two or more nucleotides.

A "coding sequence" or a sequence "encoding" an expression product, such as a RNA, polypeptide, protein, or enzyme, is a nucleotide sequence that, when expressed, results in production of the product.

The term "gene" means a DNA sequence that codes for or corresponds to a particular sequence of ribonucleotides or amino acids which comprise all or part of one or more RNA molecules, proteins or enzymes, and may or may not include regulatory DNA sequences, such as promoter sequences, which determine, for example, the conditions under which the gene is expressed. Genes may be transcribed from DNA to RNA which may or may not be translated into an amino acid sequence.

As used herein, the term "oligonucleotide" refers to a nucleic acid, generally of no more than about 100 nucleotides (e.g., 30, 40, 50, 60, 70, 80, or 90), that may be hybridizable to a genomic DNA molecule, a cDNA molecule, or an mRNA molecule encoding a gene, mRNA, cDNA, or other nucleic acid of interest. Oligonucleotides can be labeled, e.g., by incorporation of $^{32}$P-nucleotides, $^{3}$H-nucleotides, $^{14}$C-nucleotides, $^{35}$S-nucleotides or nucleotides to which a label, such as biotin, has been covalently conjugated. In one embodiment, a labeled oligonucleotide can be used as a probe to detect the presence of a nucleic acid. In another embodiment, oligonucleotides (one or both of which may be labeled) can be used as PCR primers, either for cloning full length or a fragment of the gene, or to detect the presence of nucleic acids. Generally, oligonucleotides are prepared synthetically, preferably on a nucleic acid synthesizer.

A "protein sequence", "peptide sequence" or "polypeptide sequence" or "amino acid sequence" includes a series of two or more amino acids in a protein, peptide or polypeptide. "Protein", "peptide" or "polypeptide" includes a contiguous string of two or more amino acids.

The terms "isolated polynucleotide" or "isolated polypeptide" include a polynucleotide (e.g., RNA or DNA molecule, or a mixed polymer) or a polypeptide, respectively, which are partially or fully separated from other components that are normally found in cells or in recombinant DNA expression systems. These components include, but are not limited to, cell membranes, cell walls, ribosomes, polymerases, serum components and extraneous genomic sequences.

An isolated polynucleotide or polypeptide will, preferably, be an essentially homogeneous composition of molecules but may contain some heterogeneity.

"Amplification" of DNA as used herein may denote the use of polymerase chain reaction (PCR) to increase the concentration of a particular DNA sequence within a mixture of DNA sequences. For a description of PCR see Saiki, et al., Science (1988) 239:487.

The term "host cell" includes any cell of any organism that is selected, modified, transfected, transformed, grown, or used or manipulated in any way, for the production of a substance by the cell, for example the expression or replication, by the cell, of a gene, a DNA or RNA sequence or a protein. Preferred host cells include chinese hamster ovary (CHO) cells, murine macrophage J774 cells or any other macrophage cell line and human intestinal epithelial Caco2 cells.

The nucleotide sequence of a nucleic acid may be determined by any method known in the art (e.g., chemical sequencing or enzymatic sequencing). "Chemical sequencing" of DNA includes methods such as that of Maxam and Gilbert (1977) (Proc. Natl. Acad. Sci. USA 74:560), in which DNA is randomly cleaved using individual base-specific reactions. "Enzymatic sequencing" of DNA includes methods such as that of Sanger (Sanger, et al., (1977) Proc. Natl. Acad. Sci. USA 74:5463).

The nucleic acids herein may be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like.

In general, a "promoter" or "promoter sequence" is a DNA regulatory region capable of binding an RNA polymerase in a cell (e.g., directly or through other promoter-bound proteins or substances) and initiating transcription of a coding sequence. A promoter sequence is, in general, bounded at its 3' terminus by the transcription initiation site and extends upstream (5' direction) to include the minimum number of bases or elements necessary to initiate transcription at any level. Within the promoter sequence may be found a transcription initiation site (conveniently defined, for example, by mapping with nuclease S1), as well as protein binding domains (consensus sequences) responsible for the binding of RNA polymerase. The promoter may be operably associated with other expression control sequences, including enhancer and repressor sequences or with a nucleic acid of the invention. Promoters which may be used to control gene expression include, but are not limited to, cytomegalovirus (CMV) promoter (U.S. Pat. Nos. 5,385,839 and 5,168,062), the SV40 early promoter region (Benoist, et al., (1981) Nature 290:304-310), the promoter contained in the 3' long terminal repeat of Rous sarcoma virus (Yamamoto, et al., (1980) Cell 22:787-797), the herpes thymidine kinase promoter (Wagner, et al., (1981) Proc. Natl. Acad. Sci. USA 78:1441-1445), the regulatory sequences of the metallothionein gene (Brinster, et al., (1982) Nature 296:39-42); prokaryotic expression vectors such as the β-lactamase promoter (VIIIa-Komaroff, et al., (1978) Proc. Natl. Acad. Sci. USA 75:3727-3731), or the tac promoter (DeBoer, et al., (1983) Proc. Natl. Acad. Sci. USA 80:21-25); see also "Useful proteins from recombinant bacteria" in Scientific American (1980) 242:74-94; and promoter elements from yeast or other fungi such as the Gal 4 promoter, the ADC (alcohol dehydrogenase) promoter, PGK (phosphoglycerol kinase) promoter or the alkaline phosphatase promoter.

A coding sequence is "under the control of", "functionally associated with" or "operably associated with" transcriptional and translational control sequences in a cell when the sequences direct RNA polymerase mediated transcription of the coding sequence into RNA, preferably mRNA, which then may be RNA spliced (if it contains introns) and, optionally, translated into a protein encoded by the coding sequence.

The terms "express" and "expression" mean allowing or causing the information in a gene, RNA or DNA sequence to become manifest; for example, producing a protein by activating the cellular functions involved in transcription and translation of a corresponding gene. A DNA sequence is expressed in or by a cell to form an "expression product" such as an RNA (e.g., mRNA) or a protein. The expression product itself may also be said to be "expressed" by the cell.

The term "transformation" means the introduction of a nucleic acid into a cell. The introduced gene or sequence may be called a "clone". A host cell that receives the introduced DNA or RNA has been "transformed" and is a "transformant" or a "clone." The DNA or RNA introduced to a host cell can come from any source, including cells of the same genus or species as the host cell, or from cells of a different genus or species.

The term "vector" includes a vehicle (e.g., a plasmid) by which a DNA or RNA sequence can be introduced into a host cell, so as to transform the host and, optionally, promote expression and/or replication of the introduced sequence.

Vectors that can be used in this invention include plasmids, viruses, bacteriophage, integratable DNA fragments, and other vehicles that may facilitate introduction of the nucleic acids into the genome of the host. Plasmids are the most commonly used form of vector but all other forms of vectors which serve a similar function and which are, or become, known in the art are suitable for use herein. See, e.g., Pouwels, et al., *Cloning Vectors: A Laboratory Manual,* 1985 and Supplements, Elsevier, N.Y., and Rodriguez et al. (eds.), *Vectors: A Survey of Molecular Cloning Vectors and Their Uses,* 1988, Buttersworth, Boston, Mass.

The term "expression system" means a host cell and compatible vector which, under suitable conditions, can express a protein or nucleic acid which is carried by the vector and introduced to the host cell. Common expression systems include *E. coli* host cells and plasmid vectors, insect host cells and Baculovirus vectors, and mammalian host cells and vectors.

Expression of nucleic acids encoding the p53 polypeptides of this invention can be carried out by conventional methods in either prokaryotic or eukaryotic cells. Although *E. coli* host cells are employed most frequently in prokaryotic systems, many other bacteria, such as various strains of *Pseudomonas* and *Bacillus*, are known in the art and can be used as well. Suitable host cells for expressing nucleic acids encoding the p53 polypeptides include prokaryotes and higher eukaryotes. Prokaryotes include both gram-negative and gram-positive organisms, e.g., *E. coli* and *B. subtilis*. Higher eukaryotes include established tissue culture cell lines from animal cells, both of non-mammalian origin, e.g., insect cells, and birds, and of mammalian origin, e.g., human, primates, and rodents.

Prokaryotic host-vector systems include a wide variety of vectors for many different species. A representative vector for amplifying DNA is pBR322 or many of its derivatives (e.g., pUC18 or 19). Vectors that can be used to express the p53 polypeptides include, but are not limited to, those containing the lac promoter (pUC-series); trp promoter (pBR322-trp); lpp promoter (the pIN-series); lambda-pP or pR promoters (pOTS); or hybrid promoters such as ptac (pDR540). See Brosius et al., "Expression Vectors Employing Lambda-, trp-, lac-, and lpp-derived Promoters", in Rodriguez and Denhardt (eds.) *Vectors: A Survey of Molecular Cloning Vectors and Their Uses*, 1988, Buttersworth, Boston, pp. 205-236. Many polypeptides can be expressed, at high levels, in an *E. coli*/T7 expression system as disclosed in U.S. Pat. Nos. 4,952,496, 5,693,489 and 5,869,320 and in Davanloo, P., et al., (1984) Proc. Natl. Acad. Sci. USA 81: 2035-2039; Studier, F. W., et al., (1986) J. Mol. Biol. 189: 113-130; Rosenberg, A. H., et al., (1987) Gene 56: 125-135; and Dunn, J. J., et al., (1988) Gene 68: 259.

Higher eukaryotic tissue culture cells may also be used for the recombinant production of the p53 polypeptides of the invention. Any higher eukaryotic tissue culture cell line can be used, including insect baculovirus expression systems and mammalian cells. Transformation or transfection and propagation of such cells have become a routine procedure. Examples of useful cell lines include HeLa cells, chinese hamster ovary (CHO) cell lines, J774 cells, Caco2 cells, baby rat kidney (BRK) cell lines, insect cell lines, bird cell lines, and monkey (COS) cell lines. Expression vectors for such cell lines usually include an origin of replication, a promoter, a translation initiation site, RNA splice sites (if genomic DNA is used), a polyadenylation site, and a transcription termination site. These vectors also, usually, contain a selection gene or amplification gene. Suitable expression vectors may be plasmids, viruses, or retroviruses carrying promoters derived, e.g., from such sources as adenovirus, SV40, parvoviruses, vaccinia virus, or cytomegalovirus. Examples of expression vectors include pCR®3.1, pcDNA1, pCD (Okayama, et al., (1985) Mol. Cell Biol. 5:1136), pMC1neo Poly-A (Thomas, et al., (1987) Cell 51:503), pREP8, pSVSPORT and derivatives thereof, and baculovirus vectors such as pAC373 or pAC610.

The present invention also includes fusions which include the p53 polypeptides and p53 polynucleotides of the present invention and a second polypeptide or polynucleotide moiety, which may be referred to as a "tag". The fused polypeptides of the invention may be conveniently constructed, for example, by insertion of a polynucleotide of the invention or fragment thereof into an expression vector. The fusions of the invention may include tags which facilitate purification or detection. Such tags include glutathione-S-transferase (GST), hexahistidine (His6) tags, maltose binding protein (MBP) tags, haemagglutinin (HA) tags, cellulose binding protein (CBP) tags and myc tags. Detectable tags such as $^{32}P$, $^{35}S$, $^{3}H$, $^{99m}Tc$, $^{123}I$, $^{111}In$, $^{68}Ga$, $^{18}F$, $^{125}I$, $^{131}I$, $^{113m}In$, $^{76}Br$, $^{67}Ga$, $^{99m}TC$, $^{123}I$, $^{111}In$ and $^{68}Ga$ may also be used to label the polypeptides and polynucleotides of the invention. Methods for constructing and using such fusions are very conventional and well known in the art.

Modifications (e.g., post-translational modifications) that occur in a polypeptide often will be a function of how it is made. For polypeptides made by expressing a cloned gene in a host, for instance, the nature and extent of the modifications, in large part, will be determined by the host cell's post-translational modification capacity and the modification signals present in the polypeptide amino acid sequence. For instance, as is well known, glycosylation often does not occur in bacterial hosts such as *E. coli*. Accordingly, when glycosylation is desired, a polypeptide can be expressed in a glycosylating host, generally a eukaryotic cell. Insect cells often carry out post-translational glycosylations which are similar to those of mammalian cells. For this reason, insect cell expression systems have been developed to express, efficiently, mammalian proteins having native patterns of glycosylation. An insect cell which may be used in this invention is any cell derived from an organism of the class Insecta. In an embodiment of the invention, the insect is *Spodoptera fruigiperda* (Sf9 or Sf21) or *Trichoplusia ni* (High 5). Examples of insect expression systems that can be used with the present invention, for example to produce p53 polypeptide, include Bac-To-Bac (Invitrogen Corporation, Carlsbad, Calif.) or Gateway (Invitrogen Corporation, Carlsbad, Calif.). If desired, deglycosylation enzymes can be used to remove carbohydrates attached during production in eukaryotic expression systems.

Other modifications may also include addition of aliphatic esters or amides to the polypeptide carboxyl terminus. The present invention also includes analogs of the p53 polypeptides which contain modifications, such as incorporation of unnatural amino acid residues, or phosphorylated amino acid residues such as phosphotyrosine, phosphoserine or phosphothreonine residues. Other potential modifications include sulfonation, biotinylation, or the addition of other moieties.

The present invention contemplates any superficial or slight modification to the amino acid or nucleotide sequences which correspond to the polypeptides of the invention. In particular, the present invention contemplates sequence conservative variants of the nucleic acids which encode the polypeptides of the invention. "Sequence-conservative variants" of a polynucleotide sequence are those in which a change of one or more nucleotides in a given codon results in no alteration in the amino acid encoded at that position. Function-conservative variants of the polypeptides of the invention are also contemplated by the present invention. "Function-conservative variants" are those in which one or more amino acid residues in a protein or enzyme have been changed without altering the overall conformation and function of the polypeptide, including, but, by no means, limited to, replacement of an amino acid with one having similar properties. Amino acids with similar properties are well known in the art. For example, polar/hydrophilic amino acids which may be interchangeable include asparagine, glutamine, serine, cysteine, threonine, lysine, arginine, histidine, aspartic acid and glutamic acid; nonpolar/hydrophobic amino acids which may be interchangeable include glycine, alanine, valine, leucine, isoleucine, proline, tyrosine, phenylalanine, tryptophan and methionine; acidic amino acids which may be interchangeable include aspartic acid and glutamic acid and basic amino acids which may be interchangeable include histidine, lysine and arginine.

The present invention includes p53 polynucleotides and fragments thereof as well as nucleic acids which hybridize to the polynucleotides. Preferably, the nucleic acids hybridize under low stringency conditions, more preferably under moderate stringency conditions and most preferably under high stringency conditions. A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook, et al., supra). The conditions of temperature and ionic strength determine the "stringency" of the hybridization. Typical low stringency hybridization conditions are 55° C., 5×SSC, 0.1% SDS, 0.25% milk, and no formamide at 42° C.; or 30% formamide, 5×SSC, 0.5% SDS at 42° C. Typical, moderate stringency hybridization conditions are similar to the low stringency conditions except the hybridization is carried out in 40% formamide, with 5× or 6×SSC at 42° C. High stringency hybridization conditions are similar to low stringency conditions except the hybridization conditions are carried out in 50% formamide, 5× or 6×SSC and, optionally, at a higher temperature (e.g., higher than 42° C.: 57° C., 59° C., 60° C., 62° C., 63° C., 65° C. or 68° C.). In general, SSC is 0.15M NaCl and 0.015M Na-citrate. Hybridization requires that the two nucleic acids contain complementary sequences, although, depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the higher the stringency under which the nucleic acids may hybridize. For hybrids of greater than 100 nucleotides in length, equations for calculating the melting temperature have been derived (see Sambrook, et al., supra, 9.50-9.51). For hybridization with shorter nucleic acids, i.e., oligonucleotides, the position of mismatches becomes more important, and the length of the oligonucleotide determines its specificity (see Sambrook, et al., supra).

Also included in the present invention are wild-type and mutant p53 polynucleotides and wild-type and mutant p53 polypeptides and sequence homologues or variants thereof (e.g., stabilized p53 mutant) along with methods of using the polynucleotides and polypeptides. In an embodiment of the invention, a homologue comprises an amino acid sequence which is at least about 70% identical, preferably at least about 80% identical, more preferably at least about 90% identical and most preferably at least about 95% identical (e.g., 95%, 96%, 97%, 98%, 99%, 100%) to the reference p53 nucleotide (e.g., SEQ ID NO: 1 or any mutant thereof, as discussed above) and amino acid sequence (e.g., SEQ ID NO: 2 or any mutant thereof, as discussed above), when the comparison is performed by a BLAST algorithm wherein the parameters of the algorithm are selected to give the largest match between the respective sequences over the entire length of the respective reference sequences. Polypeptides comprising amino acid sequences which are at least about 70% similar, preferably at least about 80% similar, more preferably at least about 90% similar and most preferably at least about 95% similar (e.g., 95%, 96%, 97%, 98%, 99%, 100%) to the reference p53 amino acid sequence of SEQ ID NO: 2 (or any mutant thereof, as discussed above), when the comparison is performed with a BLAST algorithm wherein the parameters of the algorithm are selected to give the largest match between the respective sequences over the entire length of the respective reference sequences, are also included in the present invention along with uses thereof.

Sequence identity refers to exact matches between the nucleotides or amino acids of two sequences which are being compared. Sequence similarity refers to both exact matches between the amino acids of two polypeptides which are being compared in addition to matches between nonidentical, biochemically related amino acids. Biochemically related amino acids which share similar properties and may be interchangeable are discussed above.

The following references regarding the BLAST algorithm are herein incorporated by reference: BLAST ALGORITHMS: Altschul, S. F., et al., (1990) J. Mol. Biol. 215:403-410; Gish, W., et al., (1993) Nature Genet. 3:266-272; Madden, T. L., et al., (1996) Meth. Enzymol. 266:131-141; Altschul, S. F., et al., (1997) Nucleic Acids Res. 25:3389-3402; Zhang, J., et al., (1997) Genome Res. 7:649-656; Wootton, J. C., et al., (1993) Comput. Chem. 17:149-163; Hancock, J. M., et al., (1994) Comput. Appl. Biosci. 10:67-70; ALIGNMENT SCORING SYSTEMS: Dayhoff, M. O., et al., "A model of evolutionary change in proteins." in *Atlas of Protein Sequence and Structure*, (1978) vol. 5, suppl. 3. M. O. Dayhoff (ed.), pp. 345-352, Natl. Biomed. Res. Found., Washington, D.C.; Schwartz, R. M., et al., "Matrices for detecting distant relationships." in *Atlas of Protein Sequence and Structure*, (1978) vol. 5, suppl. 3." M. O. Dayhoff (ed.), pp. 353-358, Natl. Biomed. Res. Found., Washington, D.C.; Altschul, S. F., (1991) J. Mol. Biol. 219:555-565; States, D. J., et al., (1991) Methods 3:66-70; Henikoff, S., et al., (1992) Proc. Natl. Acad. Sci. USA 89:10915-10919; Altschul, S. F., et al., (1993) J. Mol. Evol. 36:290-300; ALIGNMENT STATISTICS: Karlin, S., et al., (1990) Proc. Natl. Acad. Sci. USA 87:2264-2268; Karlin, S., et al., (1993) Proc. Natl. Acad. Sci. USA 90:5873-5877; Dembo, A., et al., (1994) Ann. Prob. 22:2022-2039; and Altschul, S. F. "Evaluating the statistical significance of multiple distinct local alignments." in *Theoretical and Computational Methods in Genome Research* (S. Suhai, ed.), (1997) pp. 1-14, Plenum, New York.

Assays

Anti-cancer agents and p53 stabilizers can be identified using scintillation proximity assays (SPA). SPA assays are conventional and very well known in the art; see, for example, U.S. Pat. No. 4,568,649. In SPA, the target of interest is immobilised to a small microsphere typically approximately 5 microns in diameter. The microsphere, typically, includes a solid scintillant core which has been coated with a polyhydroxy film, which in turn contains coupling molecules, which allow generic links for assay design. When a radioisotopically labeled molecule binds to the microsphere, the radioisotope is brought into close proximity to the scintillant and effective energy transfer from electrons emitted by the isotope will take place resulting in the emission of light. While the radioisotope remains in free solution, it is too distant from the scintillant and the electron will dissipate the energy into the aqueous medium and therefore remain undetected. Scintillation may be detected with a scintillation counter. In general, $^3H$ and $^{125}I$ labels are well suited to SPA.

For example, lectin wheat germ agglutinin (WGA) may be used as the SPA bead coupling molecule (Amersham Biosciences; Piscataway, N.J.). The WGA coupled bead captures glycosylated, cellular membranes and glycoproteins and has been used for a wide variety of receptor sources and cultured cell membranes. The target/bait is immobilized onto the WGA-SPA bead and a signal is generated on binding of an isotopically labeled ligand. Other coupling molecules which may be useful for SPA assays include poly-L-lysine and WGA/polyethyleneimine (Amersham Biosciences; Piscataway, N.J.). See, for example, Berry, J. A., et al., (1991) Cardiovascular Pharmacol. 17 (Suppl.7): S143-S145; Hoffman, R., et al., (1992) Anal. Biochem. 203: 70-75; Kienhus, et al., (1992) J. Receptor Research 12: 389-399; Jing, S., et al., (1992) Neuron 9: 1067-1079.

In an embodiment of the invention, GST-labeled mutant p53 or a fragment thereof (e.g., DNA binding domain such as amino acids 92-312 of SEQ ID NO: 2) is bound to glutathione labeled SPA beads.

The scintillant contained in SPA beads may include, for example, yttrium silicate (YSi), yttrium oxide (YOx), diphenyloxazole or polyvinyltoluene (PVT) which acts as a solid solvent for diphenylanthracine (DPA).

An embodiment of the invention provides a method for testing a substance for the presence of an anti-cancer agent or a p53 stabilizer comprising: (a) placing, in an aqueous suspension, a plurality of support particles, impregnated with a fluorescer (e.g., glutathione labeled beads), to which a p53 polypeptide or fragment thereof (e.g., DNA binding domain) or a fusion thereof (e.g., GST fusion) is attached; (b) adding, to the suspension, a known, radiolabeled p53-binding substance and a sample to be tested for the presence of the agent or stabilizer, wherein the radiolabel emits radiation energy capable of activating the fluorescer upon the binding of the binding substance to the p53 mutant polypeptide or a fusion thereof to produce light energy, whereas radiolabeled p53-binding substance that does not bind to the polypeptide is, generally, too far removed from the support particles to enable the radioactive energy to activate the fluorescer; and (c) measuring the light energy emitted by the fluorescer in the suspension; wherein an anti-cancer agent or a p53 stabilizer in the sample is identified by measuring substantially reduced light energy emission, compared to what would be measured in the absence of such a substance.

In an embodiment of the invention, a sample identified by the SPA assay discussed above, using an unmutated p53 polypeptide of fusion or fragment thereof is tested further for the ability to stabilize p53 in vitro or in vivo (e.g., using any assay set forth below).

In an embodiment of the invention, an optional negative-control assay is performed. In an embodiment, such an assay comprises: (a) placing, in an aqueous suspension, a plurality of support particles, impregnated with a fluorescer, to which a p53 mutant polypeptide or a fusion thereof is attached; (b) adding, to the suspension, a known, radiolabeled p53-binding substance wherein the radiolabel emits radiation energy capable of activating the fluorescer upon the binding of the binding substance to the p53 mutant polypeptide or a fusion thereof to produce light energy, whereas radiolabeled p53-binding substance that does not bind to the polypeptide is, generally, too far removed from the support particles to enable the radioactive energy to activate the fluorescer; and (c) measuring the light energy emitted by the fluorescer in the suspension; wherein the assay is determined to be operating properly if light energy emission is observed from the suspension; particularly if the level of light emission is substantially greater than that observed in the positive-control assay set forth below.

In an embodiment of the invention, an optional positive-control assay is performed. In an embodiment, such an assay comprises: (a) placing, in an aqueous suspension, a plurality of support particles, impregnated with a fluorescer, to which a p53 mutant polypeptide or a fusion thereof is attached; (b) adding, to the suspension, a known, radiolabeled p53-binding substance and a known, non-radiolabeled p53-binding substance, wherein the radiolabel emits radiation energy capable of activating the fluorescer upon the binding of the binding substance to the p53 mutant polypeptide or a fusion thereof to produce light energy, whereas radiolabeled p53-binding substance that does not bind to the polypeptide is, generally, too far removed from the support particles to enable the radioactive energy to activate the fluorescer; and (c) measuring the light energy emitted by the fluorescer in the suspension; wherein the assay is determined to be operating properly if no significant light energy emission is observed or if substantially less light energy emission is observed from the suspension than is observed in the above-mentioned negative-control assay or if substantially less light energy emission is observed in the present of the unradiolabeled binding substance than is observed in the absence of said unradiolabeled binding substance.

Alternatively, a sample may be identified as an anti-cancer agent or p53 stabilizer by directly detecting binding in a SPA assay. In this assay, a radiolabeled (e.g., $^3$H) candidate compound to be tested is put in contact with the mutant p53 polypeptide which is bound to the SPA bead. Fluorescence may then be assayed to detect the presence of a complex between the labeled candidate compound and the mutant p53 polypeptide. For example, an embodiment of the invention provides a method for testing a substance for the presence of an anti-cancer agent or a p53 stabilizer comprising: (a) placing, in an aqueous suspension, a plurality of support particles, impregnated with a fluorescer, to which a p53 mutant polypeptide or fragment thereof (e.g., DNA binding domain) or a fusion (e.g., GST fusion) thereof is attached; (b) adding, to the suspension radiolabeled sample or substance to be tested for the ability to treat or prevent cancer or to stabilize p53, wherein the radiolabel emits radiation energy capable of activating the fluorescer upon the binding of the radiolabeled substance to the p53 mutant polypeptide or a fusion thereof to produce light energy, whereas radiolabeled substance that does not bind to the polypeptide is, generally, too far removed from the support particles to enable the radioactive energy to activate the fluorescer; and (c) measuring the light energy emitted by the fluorescer in the suspension; wherein the sample or substance being tested is identified as an anti-cancer agent or a p53 stabilizer by measuring substantially more light energy emission, compared to what would be measured in the absence of the sample or substance being tested.

In an embodiment, the direct binding SPA assay is performed in association with an optional positive-control assay. For example, in an embodiment of the invention, the assay comprises (a) placing, in an aqueous suspension, a plurality of support particles, impregnated with a fluorescer, to which a p53 mutant polypeptide or a fragment or a fusion thereof is attached; (b) adding, to the suspension a radiolabeled substance known to bind to the mutant p53 polypeptide, wherein the radiolabel emits radiation energy capable of activating the fluorescer upon the binding of the radiolabeled substance to the p53 mutant polypeptide or a fusion thereof to produce light energy, whereas radiolabeled substance that does not bind to the polypeptide is, generally, too far removed from the support particles to enable the radioactive energy to activate the fluorescer; and (c) measuring the light energy emitted by the fluorescer in the suspension; wherein the assay is determined to be operating properly if light energy emission is observed from the suspension.

In an embodiment, the direct binding SPA assay is performed in association with an optional negative-control assay. For example, in an embodiment of the invention, the assay comprises (a) placing, in an aqueous suspension, a plurality of support particles, impregnated with a fluorescer, to which a p53 mutant polypeptide or a fusion thereof is attached; (b) adding, to the suspension a radiolabeled substance known to not bind to the mutant p53 polypeptide or, alternatively, no radiolabeled substance, wherein the radiolabel emits radiation energy capable of activating the fluorescer upon the binding of the radiolabeled substance to the p53 mutant polypeptide or a fusion thereof to produce light energy, whereas radiolabeled substance that does not bind to the polypeptide is, generally, too far removed from the support particles to enable the radioactive energy to activate the fluorescer; and (c) measuring the light energy emitted by the fluorescer in the suspension; wherein the assay is determined to be operating properly if substantially less light energy emission is observed from the suspension than is observed in the positive-control assay set forth above or if no significant light energy emission is observed.

Anti-cancer agents and p53 stabilizers can be identified using surface plasmon resonance (SPR) assays. SPR is a surface sensitive optical technique for monitoring the adsorption of solution species into patterned molecular microarrays that have been made on chemically modified metal surfaces (e.g., gold). SPR can be used to study the specific adsorption of biopolymers (such as proteins or antibodies) onto DNA. Surface plasmon resonance (SPR) allows sensitive detection of the molecular interactions in real-time, without the use of labels. Generally, the method uses a quantum phenomenon that arises when light is reflected under certain conditions from a conducting film at the interface between two media of different refractive index. In the Biacore® system, for example, one interaction partner is immobilized on the surface of a chip ("sensor chip"), while the other interactant is injected in the flow over the surface. Thus, the two media are the sample and the glass of the sensor chip, separated by a thin gold layer. The SPR phenomenon causes a reduction in the intensity of reflected light at a specific angle of reflection. This angle depends on the refractive index close to the surface on the side opposite from the reflected light (the sample side in Biacore®). When molecules in the sample bind to the sensor surface, the refractive index at the surface increases and the SPR response changes (i.e., the angle of minimum reflected light intensity is changed). This response is displayed in arbitrary, relative "response units" (RU). Plotting RU against time ("sensorgram") gives the time course of association and dissociation for any given interaction.

An embodiment of the invention comprises a method for testing a substance for the presence of an anti-cancer agent or a p53 stabilizer comprising: (a) contacting a polynucleotide comprising a p53-binding sequence (e.g., SEQ ID NO: 4) on a surface of a sensor chip with mutant p53 polypeptide or a fragment or fusion thereof and with a substance to be tested for the presence of the agent or stabilizer under conditions that permit a wild-type p53 polypeptide to bind the coating; (b) measuring any change in surface plasmon resonance signal of the sensor chip resulting from the mutant p53 polypeptide binding to the polynucleotide coating; wherein the substance is determine to contain the agent or stabilizer if the surface plasmon resonance change is detected relative to binding of the polypeptide to the polynucleotide coating in the absence of said substance.

In an embodiment of the invention, the SPR assay is performed in association with an optional positive-control assay. For example, in an embodiment of the invention, the positive-control assay comprises: (a) contacting a polynucleotide comprising a p53-binding sequence on a surface of a sensor chip with mutant p53 polypeptide or a fragment or fusion thereof and with a substance, known to bind to and stabilize mutant p53 polypeptide, under conditions that permit a wild-type p53 polypeptide to bind the coating; (b) detecting a change in surface plasmon resonance signal of the sensor chip resulting from the mutant p53 polypeptide binding to the polynucleotide coating; wherein the assay is determined to be operating correctly if an SPR signal is observed.

In an embodiment of the invention, the SPR assay is performed in association with an optional negative-control assay. For example, in an embodiment of the invention, the negative-control assay comprises: (a) contacting a polynucleotide comprising a p53-binding sequence on a surface of a sensor chip with mutant p53 polypeptide or a fragment or fusion thereof either with a substance known not to bind to or stabilize mutant p53 polypeptide or in the absence of any substance under conditions that permit a wild-type p53 polypeptide to bind the coating; (b) measuring any change in surface plasmon resonance signal of the sensor chip resulting from the mutant p53 polypeptide binding to the polynucleotide coating; wherein the assay is determined to be operating correctly if no SPR signal is observed.

Anti-cancer agents and p53 stabilizers can be identified by means of measuring DNA binding. For example, an embodiment of the invention comprises a method for testing a substance for the presence of an anti-cancer agent or a p53 stabilizer comprising: (a) contacting p53 mutant polypeptide with a substance to be tested for the agent or stabilizer and with a polynucleotide comprising a p53 consensus sequence (e.g., AGCTGGACATGCCCGG GCATGTCC (SEQ ID NO: 4)) under conditions such that a wild-type p53 would bind to the polynucleotide; and (b) determining if the p53 mutant polypeptide binds to the polynucleotide; wherein the substance is determined to contain the agent or stabilizer if the p53 mutant polypeptide binds to the polynucleotide.

DNA bound p53 mutant polypeptide can be detected in any of several ways that are commonly known in the art. For example, the polypeptide/DNA complex can be subjected to gel electrophoresis analysis. For example, polyacrylamide or agarose electrophoresis. Binding is identified if the polynucleotide migrates, under an electric gradient, through a gel matrix slower than a polynucleotide that has not been contacted with the p53 mutant polypeptide. Alternatively, the complex can be detected by gel chromatographic analysis. Since DNA/protein complexes are larger, they would migrate through the gel column at a faster rate that unbound DNA or protein. The DNA, protein and DNA/protein complexes that emerge from a gel column can be identified by measuring absorption of 260 nm and/or 280 nm light.

In an embodiment of the invention, the direct binding assay is performed in association with an optional positive-control assay. For example, in an embodiment of the invention, the positive-control assay comprises (a) contacting p53 mutant polypeptide with a substance known to bind to and stabilize the polypeptide and with a polynucleotide comprising a p53 consensus sequence (e.g., AGCTGGACATGCCCGGGCATGTCC (SEQ ID NO: 4)) under conditions such that a wild-type p53 would bind to the polynucleotide; and (b) determining if the p53 mutant polypeptide binds to the polynucleotide; wherein the assay is determined to be operating properly if binding of the p53 polypeptide is detected.

In an embodiment of the invention, the direct binding assay is performed in association with an optional negative-control assay. For example, in an embodiment of the invention, the negative-control assay comprises (a) contacting p53 mutant polypeptide either with a substance known not to bind to the polypeptide or with no substance at all and with a polynucleotide comprising a p53 consensus sequence (e.g., AGCTGGACATGCCCGGGCATGTCC (SEQ ID NO: 4)) under conditions such that a wild-type p53 would bind to the polynucleotide; and (b) determining if the p53 mutant polypeptide binds to the polynucleotide; wherein the assay is determined to be operating properly if no binding of the p53 polypeptide is detected.

Anti-cancer agents and p53 stabilizers can be identified by means of competition assays. Generally, competition assays measure the ability of a sample substance being tested to compete for binding of the polypeptide against a known p53 mutant polypeptide binding substance. Preferably, a competition assay will identify a substance that competitively inhibits binding of the known p53-binding substance. An embodiment of the invention comprises a method for testing a substance for the presence of an anti-cancer agent or a p53 stabilizer comprising: (a) contacting p53 mutant polypeptide, in the presence of a known amount of substance known to bind the p53 mutant polypeptide, with a sample to be tested for the presence of said agent or stabilizer; and (b) measuring the amount of the known p53-binding substance specifically bound to the p53 mutant polypeptide; whereby the sample is identified as containing the agent or stabilizer by measuring substantially reduced binding of the known p53-binding substance to the p53 mutant polypeptide, compared to what would be measured in the absence of the sample.

In an embodiment of the invention, the direct binding assay is performed in association with an optional positive-control assay. For example, in an embodiment of the invention, the positive-control assay comprises: (a) contacting p53 mutant polypeptide with a first and a second substance known to bind to the p53 mutant polypeptide; and (b) measuring the amount of binding of the first substance to the p53 mutant polypeptide; wherein the assay is determined to be operating properly if substantially less binding of the first substance to the polypeptide is observed in the presence of the second substance than is observed in the absence of the second substance.

In an embodiment of the invention, the direct binding assay is performed in association with an optional negative-control assay. For example, in an embodiment of the invention, the negative-control assay comprises: (a) contacting p53 mutant polypeptide with a substance known to bind to the p53 mutant polypeptide and with a negative-control substance known not to bind to the polypeptide; and (b) measuring the amount of binding of the substance that is known to bind to the p53 mutant polypeptide; wherein the assay is determined to be operating properly if the binding of the substance to the polypeptide, in the presence of the negative-control substance, is substantially the same as binding observed in the absence of the negative-control substance.

Anti-cancer agents and p53 stabilizers can be identified by means of in vivo assays. In an in vivo assay, the ability of a substance to prevent, reduce or eliminate tumor growth in an animal having a mutated p53 is measured. An embodiment of the invention comprises a method for testing a substance for the presence of an anti-cancer agent or a p53 stabilizer comprising: (a) administering the substance to a xenograft mammal comprising tumor cells (e.g., in a tumor) comprising p53 mutant polypeptide; (b) measuring tumor volume and/or growth rate over time; wherein the substance is determine to contain the agent or stabilizer if tumor volume and/or growth rate decreases over time as compared to the tumor volume and/or growth rate in a mammal which has not been contacted with the substance.

In an embodiment of the invention, the in vivo assay is performed in association with an optional positive-control assay. For example, in an embodiment of the invention, the positive-control assay comprises: (a) administering a substance known to stabilize p53 mutant polypeptide to a xenograft mammal comprising tumor cells comprising p53 mutant polypeptide; (b) measuring tumor volume and growth rate over time; wherein the assay is determined to be functioning correctly if tumor growth and/or volume is observed to decrease or cease over time.

In an embodiment of the invention, the in vivo assay is performed in association with an optional negative-control assay. For example, in an embodiment of the invention, the negative-control assay comprises: (a) administering a substance known not to stabilize p53 mutant polypeptide to a xenograft mammal comprising tumor cells comprising p53 mutant polypeptide; (b) measuring tumor volume and growth rate over time; wherein the assay is determined to be functioning correctly if tumor growth and/or volume is not observed to decrease or cease over time.

Anti-cancer agents and p53 stabilizers can be identified by means of in vitro assays. In an in vitro assay, the ability of a substance to prevent, reduce or eliminate growth of a tumor cell is determined. An embodiment of the invention comprises a method for testing a substance for the presence of an anti-cancer agent or a p53 stabilizer comprising: (a) contacting a cell comprising mutant p53 polypeptide and exhibiting a malignant phenotype (e.g., immortalization) with a substance to be tested for the presence of the agent or stabilizer; and (b) monitoring the malignant phenotype over time (e.g., measuring cell growth); wherein the substance is determine to contain the agent or stabilizer if the cell growth rate decreases over time as compared to growth rate of a cell which has not been contacted with the substance.

In an embodiment of the invention, the in vitro assay is performed in association with an optional positive-control assay. For example, in an embodiment of the invention, the positive-control assay comprises: (a) contacting a cell comprising mutant p53 polypeptide and exhibiting a malignant phenotype (e.g., immortalization) with a substance known to stabilize a mutant p53; and (b) monitoring the malignant phenotype over time (e.g., measuring cell growth); wherein the assay is determined to be operating properly if the malignant phenotype is decreased (e.g., if the rate of growth is decreased).

In an embodiment of the invention, the in vitro assay is performed in association with an optional negative-control assay. For example, in an embodiment of the invention, the negative-control assay comprises: (a) contacting a cell comprising mutant p53 polypeptide and exhibiting a malignant phenotype (e.g., immortalization) with a substance known not to stabilize a mutant p53; and (b) monitoring the malignant phenotype over time (e.g., measuring cell growth); wherein the assay is determined to be operating properly if the malignant phenotype is not decreased (e.g., if the rate of growth is not decreased).

Protein Purification

The polypeptides (e.g., p53 mutant polypeptide) of this invention can be purified by standard methods, including, but not limited to, salt or alcohol precipitation, affinity chromatography (e.g., used in conjunction with a purification tagged p53 mutant polypeptide as discussed above), preparative disc-gel electrophoresis, isoelectric focusing, high pressure liquid chromatography (HPLC), reversed-phase HPLC, gel filtration, cation and anion exchange and partition chromatography, and countercurrent distribution. Such purification methods are well known in the art and are disclosed, e.g., in *"Guide to Protein Purification", Methods in Enzymology*, Vol. 182, M. Deutscher, Ed., 1990, Academic Press, New York, N.Y.

Purification steps can be followed by performance of assays for receptor binding activity as described below. Particularly, where a polypeptide is being isolated from a cellular or tissue source, it is preferable to include one or more inhibitors of proteolytic enzymes in the assay system, such as phenylmethanesulfonyl fluoride (PMSF), Pefabloc SC, pepstatin, leupeptin, chymostatin and EDTA.

Gene Therapy

The present invention comprise methods and compositions for introducing a stabilized allele of p53, for example, a p53 allele (e.g., SEQ ID NO: 2) comprising the N268R mutation, into the cells of a patient.

Without being bound by a single theory or mechanism of action, the p53 polypeptide, comprising the N268R mutation, exhibits stable binding to DNA (e.g., comprising SEQ ID NO: 4) by interfering with MDM2-mediated p53 ubiquitination.

In an embodiment of the invention, the viral vector comprising the stabilized allele of p53 is recombinant adenovirus. In another embodiment of the invention, the viral vector comprising the stabilized allele of p53 is a retrovirus such as moloney murine leukaemia virus (Mo-MLV) or lentivirus. In an embodiment of the invention, the viral vector comprising the stabilized allele of p53 is adeno-associated virus (AAV) such as non-pathogenic human parvovirus. In an embodiment of the invention, the viral vector comprising the stabilized allele of p53 is herpes simplex virus type 1 (HSV-1).

In an embodiment of the invention, the term "adenovirus" refers to viruses of the genus *adenoviridiae*. In an embodiment of the invention, the term "recombinant adenovirus" refer to viruses of the genus *adenoviridiae* capable of infecting a cell whose viral genomes have been modified through conventional recombinant DNA techniques. In an embodiment of the invention, the term recombinant adenovirus also includes chimeric (or even multimeric) vectors, i.e. vectors constructed using complementary coding sequences from more than one viral subtype.

In an embodiment of the invention, the term "adenoviridae" refers collectively to animal adenoviruses of the genus *mastadenovirus* including but not limited to human, bovine, ovine, equine, canine, porcine, murine and simian adenovirus subgenera. In particular, human adenoviruses includes the A-F subgenera as well as the individual serotypes thereof. A-F subgenera including but not limited to human adenovirus types 1, 2, 3, 4, 4a, 5, 6, 7, 7a, 7d, 8, 9, 10, 11 (Ad11A and Ad11P), 12, 13, 14, 15, 16, 17, 18, 19, 20, 21, 22, 23, 24, 25, 26, 27, 28, 29, 30, 31, 32, 33, 34, 34a, 35, 35p, 36, 37, 38, 39, 40, 41, 42, 43, 44, 45, 46, 47, 48, and 91.

The term "stabilized allele of p53" and the like includes any allele of p53 whose activity is not modulated by MDM2. In an embodiment of the invention, a stable allele of p53 includes an amino acid sequence of SEQ ID NO:2 comprising an N268X mutation (wherein X is any amino acid other than N) such as N268R.

The term "cancer" includes all forms of the disease including, but not limited to, neuroblastoma, rhabdomyosarcoma, osteosarcoma, acromegaly, ovarian cancer, pancreatic cancer, benign prostatic hyperplasia, breast cancer, prostate cancer, bone cancer, lung cancer, colorectal cancer, cervical cancer, synovial sarcoma, bladder cancer, Wilm's cancer, ovarian cancer, benign prostatic hyperplasia (BPH), diarrhea associated with metastatic carcinoid and vasoactive intestinal peptide secreting tumors, VIPoma, Werner-Morrison syndrome, kidney cancer, renal cell carcinoma, transitional cell cancer, Ewing Sarcoma, leukemia, acute lymphoblastic leukemia, brain cancer, glioblastoma, non-glioblastoma brain cancer, meningioma, pituitary adenoma, vestibular schwannoma, a primitive neuroectodermal tumor, medulloblastoma, astrocytoma, oligodendroglioma, ependymoma and choroid plexus papilloma.

A viral vector of the invention can be used in gene therapy. For general reviews of the methods of gene therapy, see Goldspiel et al., 1993, Clinical Pharmacy 12:488-505; Wu and Wu, 1991, Biotherapy 3:87-95; Tolstoshev, 1993, Ann. Rev. Pharmacol. Toxicol. 32:573-596; Mulligan, Science 260:926-932 (1993); and Morgan and Anderson, 1993, Ann. Rev. Biochem. 62:191-217; May, 1993, TIBTECH 11(5): 155-215.

A viral vector of the invention comprises adenoviral nucleotide sequences and a stabilized p53 allele (e.g., encoding SEQ ID NO:2 comprising an N268R mutation). In an embodiment of the invention, the vector is recombinant adenovirus vector and comprises adenoviral nucleotide sequences that lack of homology to the helper adenovirus nucleic acid sequences. The lack of homology between the adenoviral helper nucleic acid sequences and recombinant adenovirus vectors reduces the possibility of the viral genome recombining to produce replication competent adenovirus. In an embodiment of the invention, the recombinant adenovirus vector encodes a replication-defective adenovirus. In accordance with this embodiment, the recombinant adenovirus vector may be engineered to comprise a mutated adenovirus genome by, e.g., introducing one or more mutations in an adenovirus genome (e.g., introducing deletions in one or more coding regions for adenoviral proteins). In an embodiment of the invention, the mutations in the adenovirus genome result in lower levels of expression of adenoviral proteins than wild-type adenovirus. The reduction in adenoviral protein expression reduces the immune response to the adenoviral proteins in a subject.

The viral vectors of the invention comprising a stabilized allele of p53 can be used for in vivo or ex vivo gene therapy. For in vivo gene therapy, recombinant adenovirus is directly administered to a subject. For ex vivo gene therapy, cells are infected with the recombinant adenovirus in vitro and then the infected cells are transplanted into the subject. In an embodiment of the invention, the recombinant adenovirus is directly administered in vivo, where the stabilized p53 allele is expressed.

In an embodiment of the invention, a cell is infected with a recombinant adenovirus comprising a stabilized p53 allele and the resulting recombinant cell is administered to a subject. The resulting recombinant cells can be delivered to a subject by various methods known in the art. The amount of cells envisioned for use depends on the desired effect, patient state, etc., and can be determined by one skilled in the art. In accordance with the invention, any cells which can be infected with a recombinant adenovirus can be for purposes of gene therapy. Non-limiting examples include epithelial cells (e.g., respiratory epithelial cells), endothelial cells, keratinocytes, fibroblasts, muscle cells, hepatocytes, blood cells (such as T lymphocytes, B lymphocytes, monocytes, macrophages, neutrophils, eosinophils, megakaryocytes, granulocytes), and various stem or progenitor cells (in particular, hematopoietic stem or progenitor cells, e.g., as obtained from bone marrow, umbilical cord blood, peripheral blood, fetal liver, etc.). In an embodiment of the invention, the cell used for gene therapy is autologous to the subject. In an embodiment in which recombinant cells are used in gene therapy, the proteins encoded by the genome of the recombinant adenovirus are expressible by the cells or their progeny, and the recombinant cells are then administered in vivo for therapeutic effect.

A vector of the present invention, for example, a replication deficient adenoviral vector, can be propagated in a SL0003 or SL0006 cell line. For example, in an embodiment, a replication deficient adenoviral vector is propagated in a cell line comprising (a) a first nucleic acid molecule comprising a nucleotide sequence encoding adenoviral E1A proteins deficient in binding to p300 protein family members and pRb protein family members; and (b) a second nucleic acid molecule comprising a nucleotide sequence encoding an adenoviral E1B-55K protein; or comprising (a) a first expression cassette comprising a promoter active in said human cell operably linked to a nucleic acid sequence encoding adenoviral E1A proteins deficient in binding to p300 protein family members and pRb protein family members, wherein said proteins are expressed in said human cell; and (b) a second expression cassette comprising a promoter active in said human cell operably linked to a nucleic acid sequence encoding an adenoviral E1B protein, wherein said E1B protein comprises an E1B-55K protein but not an E1B-19K protein, wherein said E1B-55K protein is expressed in said human cell.

In an embodiment of the invention, a recombinant adenovirus vector encodes a replication-defective adenovirus comprising a stabilized p53 allele and comprising a mutated genome with a partial or complete deletion of the E1A coding region and E1B coding region. In an embodiment of the invention, the recombinant adenovirus vector encodes a replication-defective adenovirus and comprises a mutated genome with a partial or complete deletion of the E1A coding region, E1B coding region, and E2B polymerase coding region, and includes a stabilized p53 allele.

The present invention comprise methods for treating or preventing cancer comprising administering a therapeutically effective amount of a viral vector comprising a stabilized allele of p53 to a subject or patient. A "therapeutically effective" amount of a viral vector comprising a stabilized allele of p53 comprises any amount that will elicit a biological or medical response of a tissue, system, subject or host that is being sought by the administrator (such as a researcher, doctor or veterinarian) which includes any measurable alleviation of the signs, symptoms and/or clinical indicia of a medical disorder, such as cancer (e.g., tumor growth and/or metastasis) including the prevention, slowing or halting of progression of the medical disorder to any degree. For example, in an embodiment of the invention, a therapeutically effective amount of a viral vector comprising a stable allele of p53 is from about $10^3$ to about $10^9$ PFU/dose.

In an embodiment of the invention, a stabilized p53 gene is delivered to the cells of a subject using polymer-based biomaterials including, for example, polyethylene vinyl co-acetate (EVAc); polyanhydride copolymers of fumaric & sebacic acid (poly(FA:SA)20:80); poly(lactide-co-glycolide) (PLCG); gene activated matrix (GAM); poly[alpha-(4-aminobutyl)-L-glycolic acid] (PAGA); imidazole-containing polymer; an alginate microsphere; chitosan; gelatin; or atelocollagen.

Walsh et al. showed that DNA was released from the EVAc (polyethylene vinyl co-acetate) without degradation and retained the ability to transfect cells in vitro (Biomaterials 16(17):1319-25 (1995)). Luo et al., showed that both small and large DNA molecules were encapsulated and successfully released from EVAc matrices (Pharm. Res. 16: 1300-1308 (1999)). The self-assembly of polymer "microspheres" that can carry a variety of medical materials including DNA has also been described (Mathiowitz et al., Nature, 386: 410-414 (1997)). Orally administered biodegradable poly(FA:SA) 20:80, which are polyanhydride copolymers of fumaric and sebacic acid with highly adhesive properties, allowed gene delivery to transfer biologically active molecules to the body. Alginate, a naturally occurring biopolymer extracted from brown algae (kelp), has several unique properties that have enabled it to be used as a matrix for the entrapment and/or delivery of a variety of biological agents including nucleic acid (Alexakis et al., Appl. Biochem. Biotechnol 50: 93-106 (1995); Aggarwal et al., Can. J. Vet. Res., 63: 148-152 (1999)). Biodegradable alginate microspheres were used as a delivery vesicle for DNA (Mittal et al., Vaccine 19: 253-263 (2000)).

Shea et al. and Murphy et al. demonstrated successful in vivo delivery of DNA encoding a platelet-derived growth factor gene using a polymer matrix, poly(lactide-co-glycolide) (Shea et al., Nat. Biotechnol., 17: 551-554 (1999); Murphy et al., J. Periodontal Res. 34: 413-419 (1999)). Plasmid DNA carrying a fragment of the human parathyroid hormone gene was carried into target tissue for its regeneration by a polymer matrix sponge called a gene-activated matrix (GAM) (Bonadio et al., J Mol Med., 78: 303-311 (2000); Bonadio et al., Nat Med., 5: 753-759 (1999)). DNA was also delivered to cells using poly[alpha-(4-aminobutyl)-L-glycolic acid] (PAGA), which is a biodegradable analogue of poly(L-lysine) (Lim et al., Pharm. Res., 17: 811-816 (2000); Maheshwari et al., Mol Ther. 2: 121-130 (2000)). Imidazole-containing polymers are also excellent for gene delivery to cells (Pack et al., Biotechnol. Bioeng., 67: 217-223 (2000)).

Delivery of stabilized p53 polynucleotides using chitosan, a natural cationic polysaccharide derived from naturally occurring chitin in crab and shrimp shells by deacetylation is also within the scope of the invention (see Quong et al., Biotechnol Bioeng. 60: 124-134 (1998); Quong et al., J. Microencapsul. 16: 73-82 (1999); Roy et al., Nat Med., 5: 387-391 (1999)). The self-aggregates of deoxycholic acid-modified chitosan allowed efficient DNA transfer to COS-1 cells (Lee et al., J. Control. Release, 51: 213-220 (1998)).

Delivery of a stabilized p53 gene to a host cell can also be accomplished using a gelatin based DNA delivery system. Controlled gene delivery by DNA-gelatin nanospheres has been reported (Truong-Le et al., Hum. Gene Ther. 9: 1709-1717 (1998); Truong-Le et al., Arch. Biochem. Biophys. 361: 47-56 (1999); Leong et al., J. Control Release 53: 183-193 (1998)).

Delivery of a stabilized p53 gene to the cells of a subject may also be accomplished using a atelocollagen-based system. Atelocollagen is a decomposition product of type I collagen derived from the dermis of cattle. Atelocollagen is obtained by pepsin digestion (DeLustro et al., J. Biomed. Mater. Res. 20: 109-120 (1986)) and is free from telopeptides, indicating that it has low immunogenicity (Stenzel et al., Annu Rev Biophys Bioeng. 3: 231-253 (1974)). Atelocollagen is used, for example, as a fluid or gel, either of which can be injected locally, but also as solid matter such as beads, sponges, membranes, and cylinders. Atelocollagen can be processed to profile all spaces in the body as well as organs and blood vessels when it is used as an internal implant. Thus, a gene delivery method using atelocollagen would solve issues of site specificity and target gene transfer.

EXAMPLES

The following examples are intended to exemplify and further clarify what is the present invention and should not be construed to limit the present invention. The present invention should not be limited by any mechanism or theory presented herein. Any composition disclosed in any of the following examples along with any disclosed method is part of the present invention.

Example 1

Proliferation Assay

This assay measured the growth suppression effects of small molecules in MB468 cells with mutant p53 (R273H) vs. cells with a p53 null background. The assay used Calcein AM to measure cellular viability. Cells (p53 null and mutant) were harvested and plated at 5000 cells per well in a 96-well tissue culture plate. The volume of cells in growth media was 100 µl. Serial dilutions (2× concentration) of compounds were then made and transferred to the plate of cells. The volume of compounds being tested in the growth media was 100 ul. This dilution of compound with cells gave a 1× final dilution of compound (200 µL total volume). Plates were then incubated at 37° C. for 72 hours. Media was then poured off and Calcein AM was added at the appropriate concentration and the plates are incubated in the dark for 15 minutes and read for fluorescence. The results of this assay are set forth below in Table 1.

TABLE 1

| EC50 of compounds observed in proliferation assays. | |
|---|---|
| STRUCTURE | PROLIFERATION ASSAY $EC_{50}$ MB468 (uM) |
| [structure 1] | 1.1 |
| [structure 2] | 1.4 |
| [structure 3] | 1.6 |

TABLE 1-continued

EC50 of compounds observed in proliferation assays.

| STRUCTURE | PROLIFERATION ASSAY EC$_{50}$ MB468 (uM) |
|---|---|
| 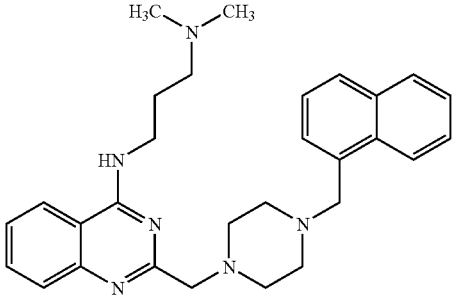 | 2.0 |
| 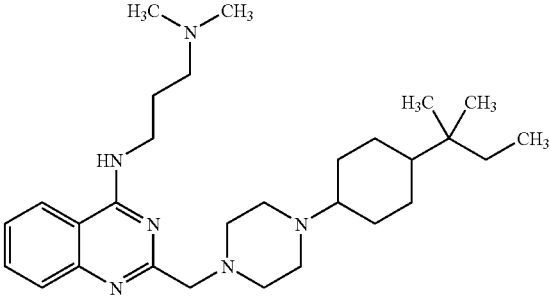 | 2.0 |
| 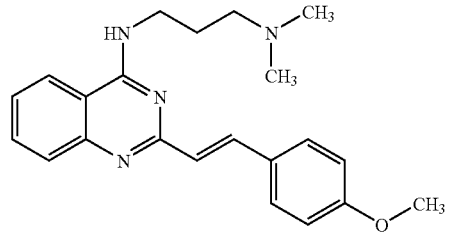 | 4.1 |

Example 2

Soft Agar Assay

This example assessed the ability of cells to grow in the absence of adhesion, which is a characteristic of tumorigenic cell lines. A small molecule

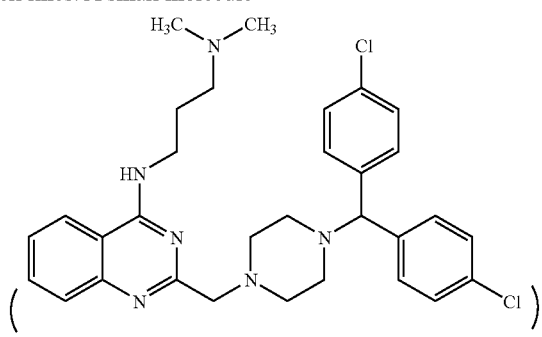

was evaluated in this assay for its anti-tumor activity and the results are given in Table 2.

Human tumor DLD1 cells containing mutant p53 (S241F) were suspended in growth medium containing 0.3% agarose and an indicated concentration of small molecule. The solution was overlayed onto growth medium solidified with 0.6% agarose containing the same concentration of the small molecule as the top layer. After the top layer was solidified, the plates were incubated for 10-16 days at 37° C. under 5% $CO_2$ to allow colony outgrowth. After incubation, colonies were stained by overlaying the agar with a solution of MTT (3-[4, 5-dimethyl-thiazol-2-yl]-2,5-diphenyltetrazolium bromide; Thiazolyl blue; 91 mg/mL in PBS). Colonies were counted to measure growth and efficacy of the small molecule. The results of this assay are set forth below in table 2.

TABLE 2

Results of Soft Agar Assay.

| Structural formula | SOFT AGAR IC$_{50}$ (μM) |
|---|---|
| (structure shown below) | 0.39 |

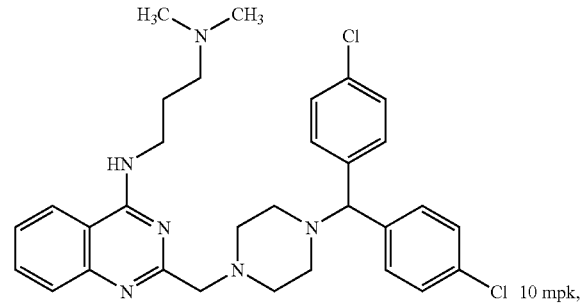

Example 3

In Vivo Anti-Tumor Studies

Unstaged Model. In this model, the therapy was started immediately after the tumor cells had been inoculated. Nude mice (5-6 week old females) were inoculated with 5×10$^6$ DLD-1 human colon adenocarcinoma cells on day 1, and randomized on day 3. The dosing of these mice was started on day 4. Groups 1 to 4, having 10 mice in each group, were dosed orally every 12 hours with vehicle,

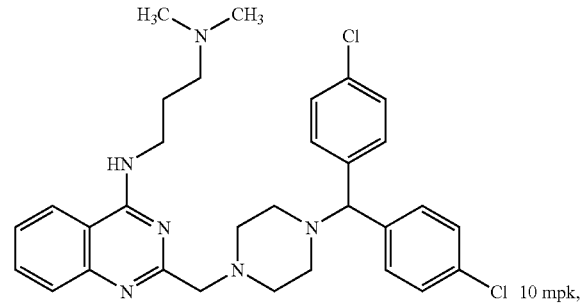 10 mpk,

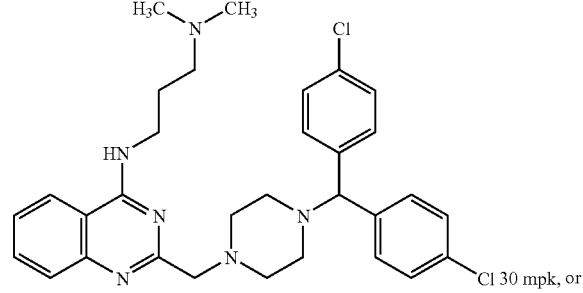 30 mpk, or

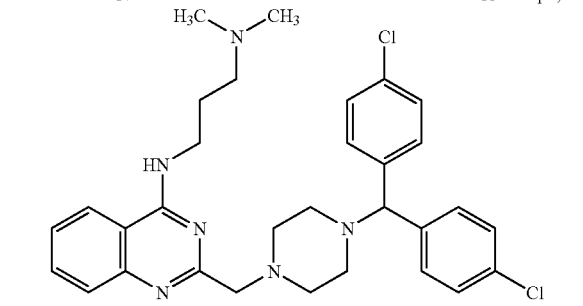

50 mpk, respectively, for 31 days. All animals were carefully monitored at least daily and each tumor was measured twice a week. The tumor growth inhibition level observed is set forth below in Table 3.

TABLE 3

Growth inhibition observed with

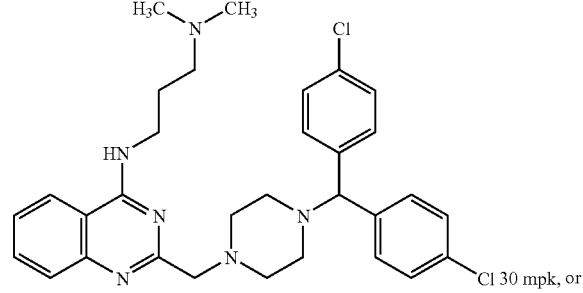

in the unstaged model.

| | 10 mpk | 30 mpk | 50 mpk |
|---|---|---|---|
| % inhibition | 48.30 | 43.23 | 78.96 |

Staged Model. In this model the initiation of therapy was delayed until the tumors had reached a certain volume. Nude mice (5-6 week old females) were inoculated with 5×10$^6$ DLD-1 human colon adenocarcinoma cells on day 1, and then randomized on day 10. The dosing of these mice was started on day 10. Groups 1 to 5, having 10 mice in each group, were dosed orally every 12 hours with no treatment, vehicle,

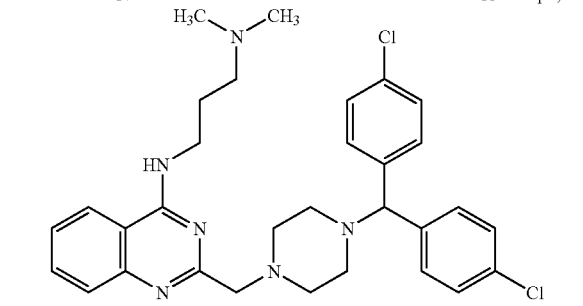 10 mpk,

-continued

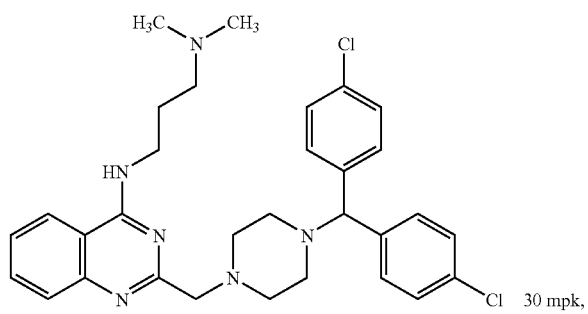

30 mpk, and

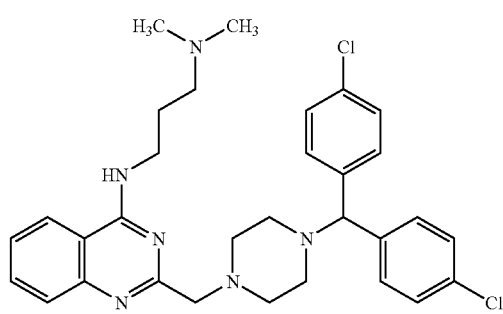

50 mpk, respectively, for 26 days. All animals were carefully monitored at least daily and each tumor was measured twice a week. The tumor growth inhibition level observed is set forth below in Table 4.

TABLE 4

Growth inhibition observed with

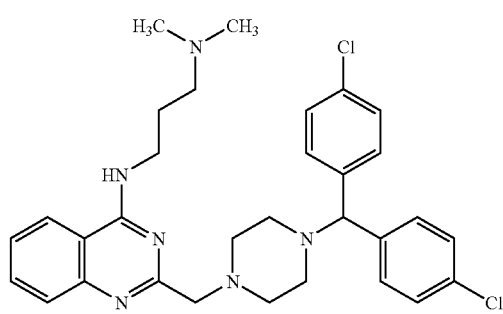

in the staged model.

| | 10 mpk | 30 mpk | 50 mpk |
|---|---|---|---|
| % inhibition | 10.15 | 14.73 | 44.31 |

Example 4

Scintillation Proximity Assay

Using

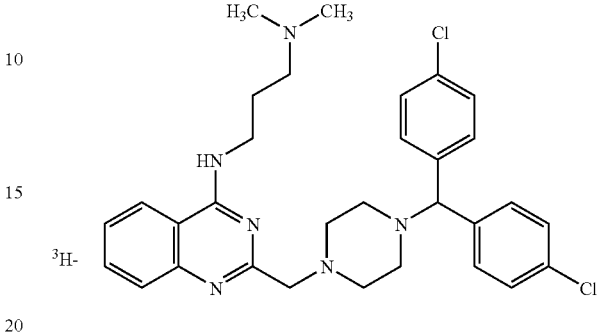

($^3$H at C bearing the chlorophenyl groups and the piperazinyl group), a radiolabeled small molecule which binds to p53, and the GST-p53 DNA binding domain (aa 92-aa 312), a quantitative screening assay was used to determine if various molecules comprise p53 binding activity. The assay is based on Scintillation Proximity Assay (SPA) technology. The complex of GST-p53,

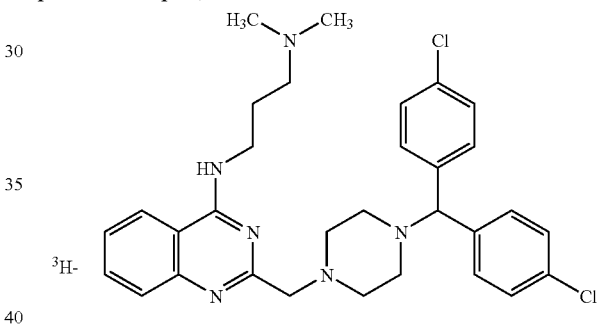

and Glutathione-SPA beads (Amersham Biosciences) were incubated with mixing for 1 hour at room temperature in the presence of the compounds to be screened. The signal was read on a Microbeta. The molecules that exhibited p53 binding activity stabilized the conformation and restored DNA binding activity to the mutant p53 protein.

The results of the SPA assay are set forth below in table 5. The numerical values expressed refer to the percentage of labeled

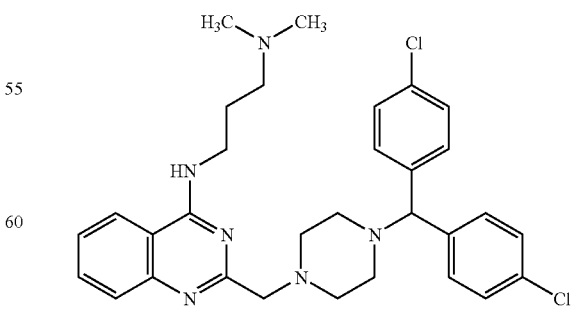

remaining bound to the mutant p53 protein after exposure to the indicated compound.

TABLE 5

Results from Scintillation Proximity Assays.

| Formula No. | Structural Formula | SPA ASSAY % Residual T @ 2 ug/mL of drug (Average of) |
|---|---|---|
| 34 | (2-((benzyl(methyl)amino)methyl)quinazolin-4(3H)-one) | 36.8 |
| 35 | (N-(3-(dimethylamino)propyl)-2-((benzyl(methyl)amino)methyl)quinazolin-4-amine) | 22.2 |
| 36 | (N-(3-(dimethylamino)propyl)-2-((methylamino)methyl)quinazolin-4-amine) | 42.6 |
| 8 | (N-(3-(dimethylamino)propyl)-2-((4-(bis(4-chlorophenyl)methyl)piperazin-1-yl)methyl)quinazolin-4-amine) | 16.1 |

TABLE 5-continued

Results from Scintillation Proximity Assays.

| Formula No. | Structural Formula | SPA ASSAY % Residual T @ 2 ug/mL of drug (Average of) |
|---|---|---|
| 9 | | 27.9 |
| 10 | | 46.1 |
| 37 | | 77.0 |
| 11 | Chiral | 39.5 |

TABLE 5-continued

Results from Scintillation Proximity Assays.

| Formula No. | Structural Formula | SPA ASSAY % Residual T @ 2 ug/mL of drug (Average of) |
|---|---|---|
| 12 | *(chiral structure: quinazoline with valine methyl ester at 4-position via HN, and 2-methylpiperazine bearing a carbamoyl-N-H-CH(phenyl)₂ group)* | 45.6 |
| 13 | *(quinazoline with 4-HN-(CH₂)₃-N(CH₃)₂ and 2-CH₂-piperazine-CH₂-(7-indolyl))* | 37.9 |
| 14 | *(quinazoline with 4-HN-(CH₂)₃-N(CH₃)₂ and 2-CH₂-piperazine-CH₂-(1-naphthyl))* | 27.9 |
| 38 | *(quinazoline with 4-HN-(CH₂)₃-N(CH₃)₂ and 2-CH₂-piperazine-N-cyclopentyl bearing a C(CH₃)₂CH₂CH₃ group)* | 55.7 |

TABLE 5-continued
Results from Scintillation Proximity Assays.
| Formula No. | Structural Formula | SPA ASSAY % Residual T @ 2 ug/mL of drug (Average of) |
|---|---|---|
| 15 | 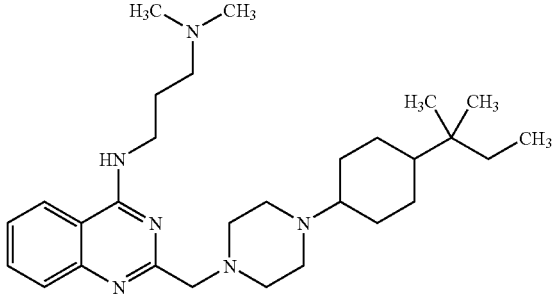 | 38.1 |
| 39 | 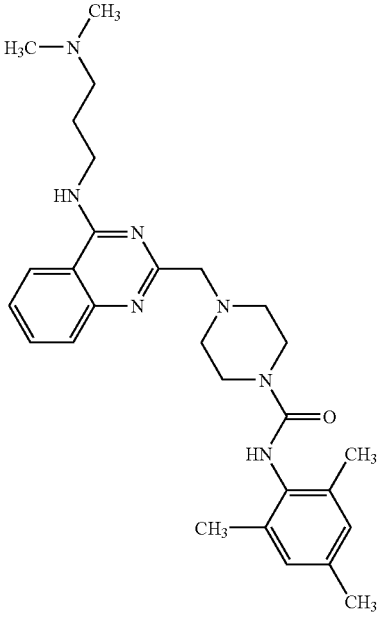 | 53.0 |
| 40 | 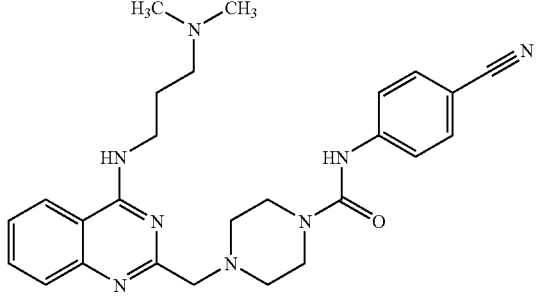 | 52.5 |

TABLE 5-continued

Results from Scintillation Proximity Assays.

| Formula No. | Structural Formula | SPA ASSAY % Residual T @ 2 ug/mL of drug (Average of) |
|---|---|---|
| 16 | | 38.0 |
| 17 | | 29.9 |
| 41 | | 63.1 |
| 42 | | 70.0 |

TABLE 5-continued

Results from Scintillation Proximity Assays.

| Formula No. | Structural Formula | SPA ASSAY % Residual T @ 2 ug/mL of drug (Average of) |
|---|---|---|
| 43 | | 80.7 |
| 44 | | 83.9 |
| 45 | | 61.6 |
| 46 | | 87.5 |

TABLE 5-continued

Results from Scintillation Proximity Assays.

| Formula No. | Structural Formula | SPA ASSAY % Residual T @ 2 ug/mL of drug (Average of) |
|---|---|---|
| 47 | | 85.0 |
| 48 | | 66.0 |
| 49 | | 65.7 |
| 50 | | 53.0 |

TABLE 5-continued

Results from Scintillation Proximity Assays.

| Formula No. | Structural Formula | SPA ASSAY % Residual T @ 2 ug/mL of drug (Average of) |
|---|---|---|
| 51 | | 61.6 |
| 52 | | 79.9 |
| 53 | | 62.7 |
| 18 | | 47.9 |

TABLE 5-continued
Results from Scintillation Proximity Assays.
| Formula No. | Structural Formula | SPA ASSAY % Residual T @ 2 ug/mL of drug (Average of) |
|---|---|---|
| 54 | 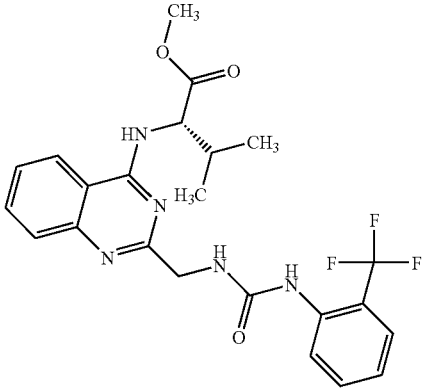 | 48.1 |
| 55 | 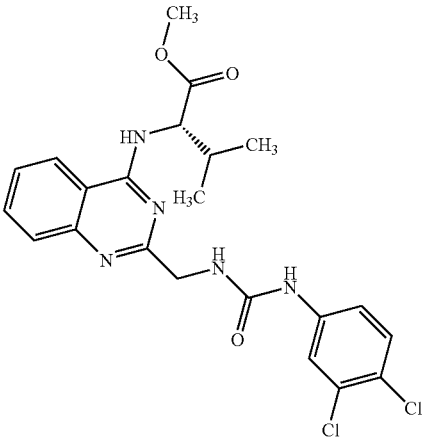 | 57.0 |
| 56 | 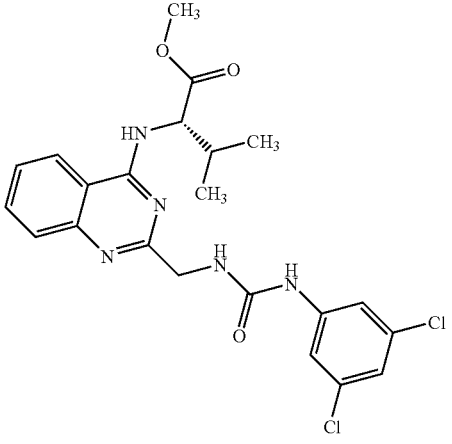 | 52.3 |

TABLE 5-continued
Results from Scintillation Proximity Assays.
| Formula No. | Structural Formula | SPA ASSAY % Residual T @ 2 ug/mL of drug (Average of) |
|---|---|---|
| 57 | 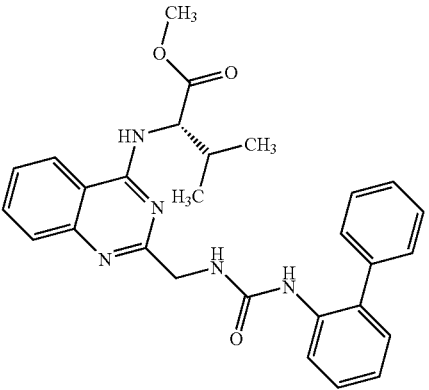 | 52.7 |
| 58 | 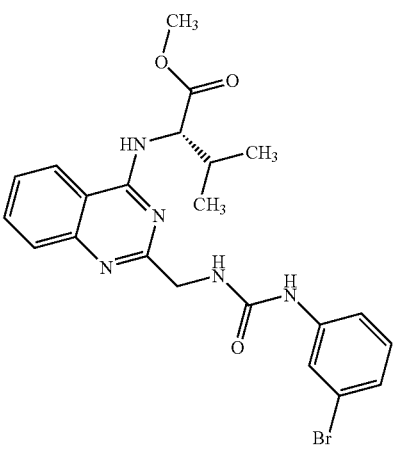 | 44.9 |
| 59 | 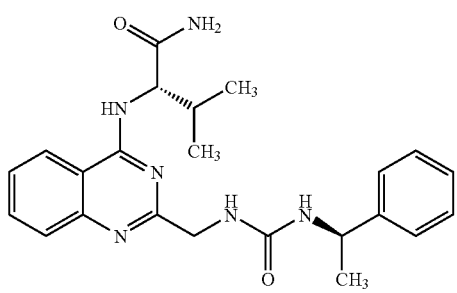 | 56.8 |

TABLE 5-continued

Results from Scintillation Proximity Assays.

| Formula No. | Structural Formula | SPA ASSAY % Residual T @ 2 ug/mL of drug (Average of) |
|---|---|---|
| 60 | (structure) | 60.0 |
| 61 | (structure) | 31.6 (3) |
| 62 | (structure) | 50.0 (3) |
| 63 | (structure) | 52.7 |

TABLE 5-continued

Results from Scintillation Proximity Assays.

| Formula No. | Structural Formula | SPA ASSAY % Residual T @ 2 ug/mL of drug (Average of) |
|---|---|---|
| 64 | | 50.7 (3) |
| 65 | | 65.5 |
| 66 | | 37.0 (3) |
| 67 | | 64.1 |

TABLE 5-continued

Results from Scintillation Proximity Assays.

| Formula No. | Structural Formula | SPA ASSAY % Residual T @ 2 ug/mL of drug (Average of) |
|---|---|---|
| 68 | | 52.7 |
| 69 | | 50.9 |
| 70 | | 54.1 |
| 71 | | 68.4 |

TABLE 5-continued

Results from Scintillation Proximity Assays.

| Formula No. | Structural Formula | SPA ASSAY % Residual T @ 2 ug/mL of drug (Average of) |
|---|---|---|
| 72 | quinazoline with 4-NH-(CH₂)₃-N(CH₃)₂ and 2-CH₂-N(CH₃)-(2,6-dimethylphenyl) | 69.7 |
| 73 | quinazoline with 4-NH-(CH₂)₃-N(CH₃)₂ and 2-CH₂-N(CH₃)-(4-methoxyphenyl) | 44.4 |
| 74 | quinazoline with 4-NH-(CH₂)₃-N(CH₃)₂ and 2-CH₂-N(CH₃)-(4-chlorophenyl) | 55.1 |
| 75 | quinazoline with 4-NH-(CH₂)₃-N(CH₃)₂ and 2-CH₂-N(CH₃)-(2,6-difluorophenyl) | 58.9 |

TABLE 5-continued
Results from Scintillation Proximity Assays.
| Formula No. | Structural Formula | SPA ASSAY % Residual T @ 2 ug/mL of drug (Average of) |
|---|---|---|
| 76 | 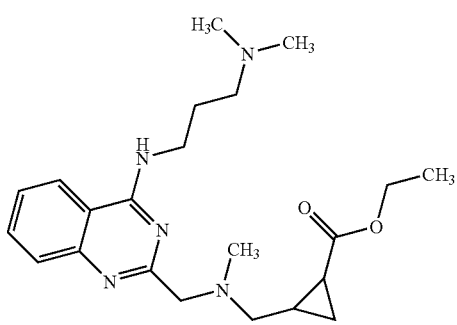 | 57.8 |
| 77 | 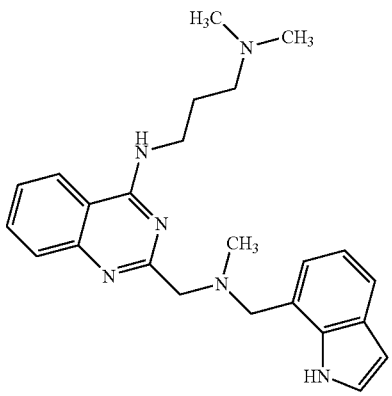 | 25.7 |
| 78 | 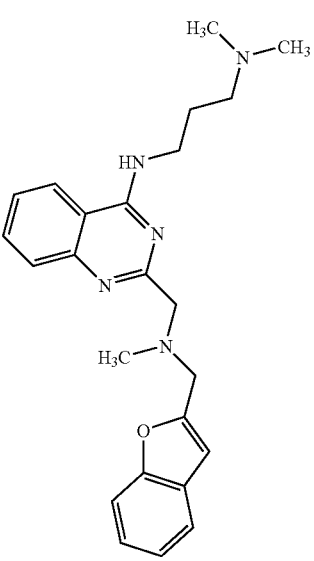 | 45.9 (3) |

TABLE 5-continued

Results from Scintillation Proximity Assays.

| Formula No. | Structural Formula | SPA ASSAY % Residual T @ 2 ug/mL of drug (Average of) |
|---|---|---|
| 79 | (structure) | 67.6 |
| 80 | (structure) | 65.6 |
| 81 | (structure) | 46.8 |

TABLE 5-continued

Results from Scintillation Proximity Assays.

| Formula No. | Structural Formula | SPA ASSAY % Residual T @ 2 ug/mL of drug (Average of) |
|---|---|---|
| 82 | | 52.9 |
| 83 | | 45.9 (3) |
| 84 | | 44.1 |

TABLE 5-continued
Results from Scintillation Proximity Assays.
| Formula No. | Structural Formula | SPA ASSAY % Residual T @ 2 ug/mL of drug (Average of) |
|---|---|---|
| 85 | 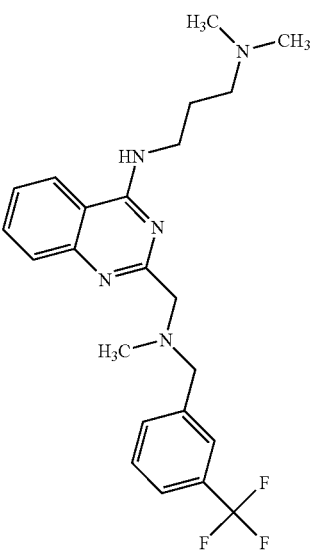 | 48.4 (3) |
| 86 | 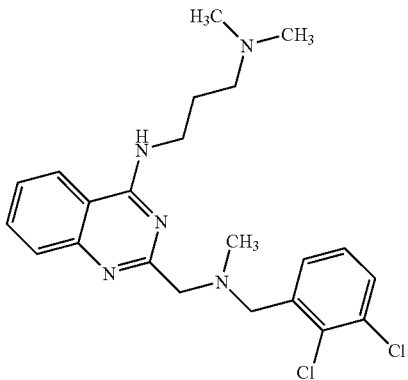 | 61.1 |
| 87 | 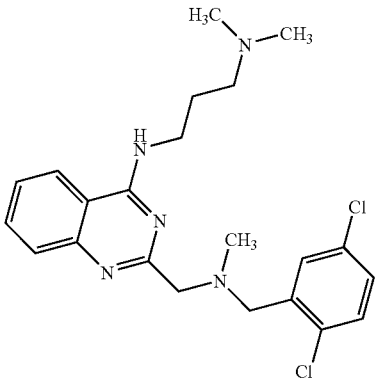 | 49.5 (3) |

TABLE 5-continued
Results from Scintillation Proximity Assays.
| Formula No. | Structural Formula | SPA ASSAY % Residual T @ 2 ug/mL of drug (Average of) |
|---|---|---|
| 88 | 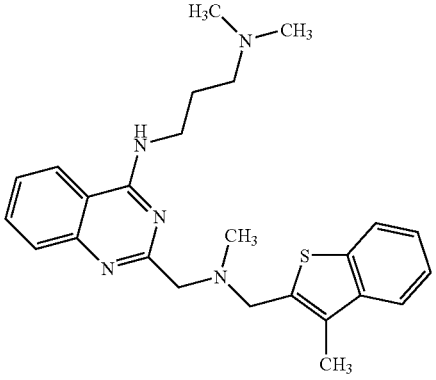 | 23.6 (3) |
| 89 | 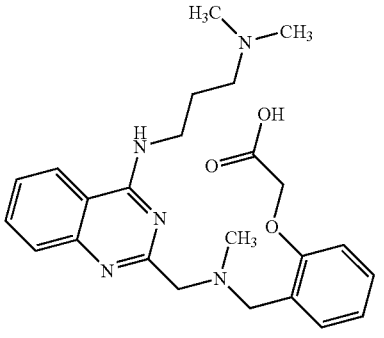 | 60.1 (3) |
| 90 | 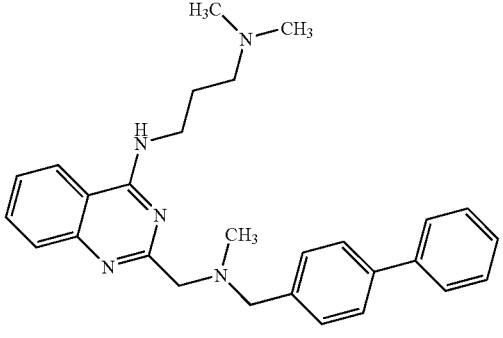 | 68.1 |
| 91 | 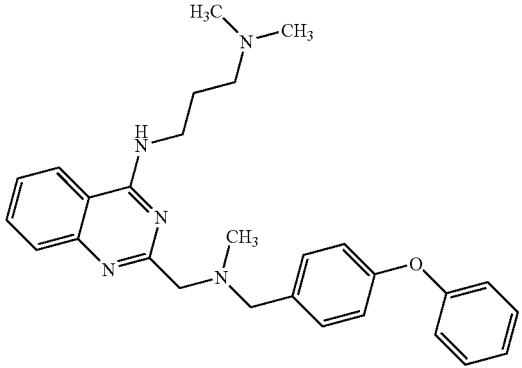 | 54.0 |

TABLE 5-continued
Results from Scintillation Proximity Assays.
| Formula No. | Structural Formula | SPA ASSAY % Residual T @ 2 ug/mL of drug (Average of) |
|---|---|---|
| 92 | 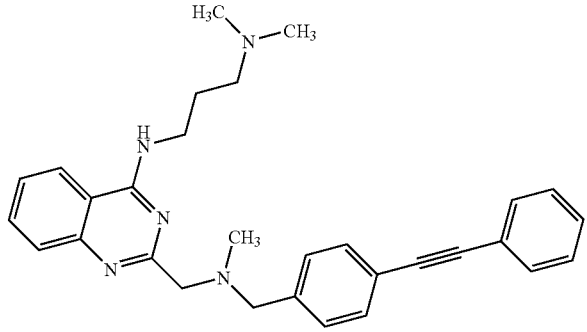 | 61.1 |
| 93 | 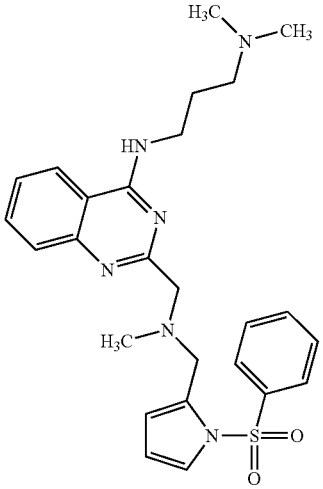 | 45.1 (3) |
| 94 | 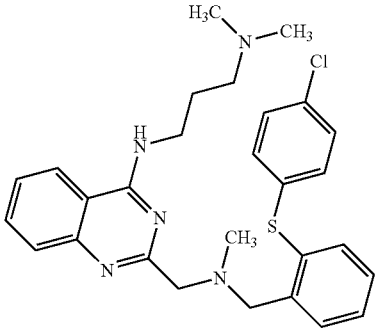 | 53.7 |

TABLE 5-continued

Results from Scintillation Proximity Assays.

| Formula No. | Structural Formula | SPA ASSAY % Residual T @ 2 ug/mL of drug (Average of) |
|---|---|---|
| 95 | | 66.5 |
| 96 | | 45.5 (3) |
| 97 | | 45.0 (3) |

TABLE 5-continued
Results from Scintillation Proximity Assays.
| Formula No. | Structural Formula | SPA ASSAY % Residual T @ 2 ug/mL of drug (Average of) |
|---|---|---|
| 98 | 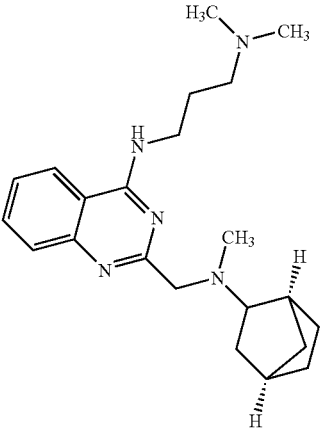 | 64.4 |
| 99 | 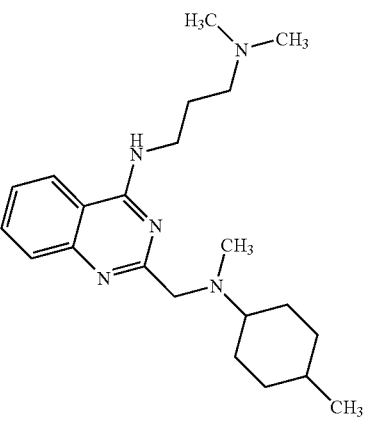 | 56.5 |
| 100 | 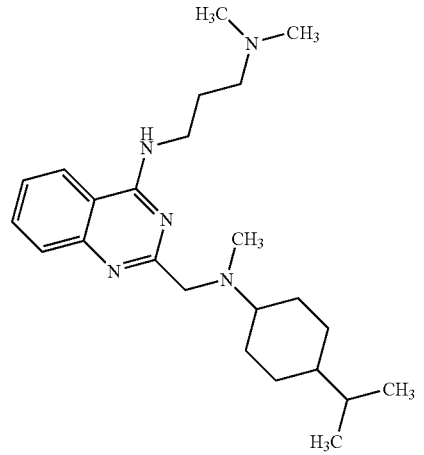 | 13.5 (3) |

TABLE 5-continued
Results from Scintillation Proximity Assays.
| Formula No. | Structural Formula | SPA ASSAY % Residual T @ 2 ug/mL of drug (Average of) |
|---|---|---|
| 101 | 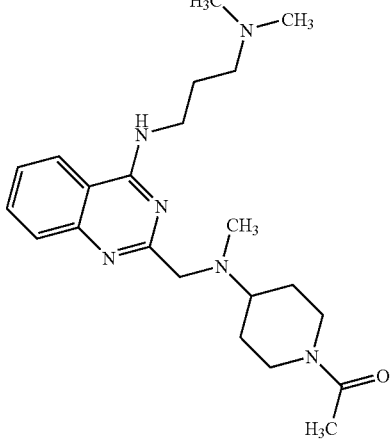 | 47.7 (3) |
| 102 | 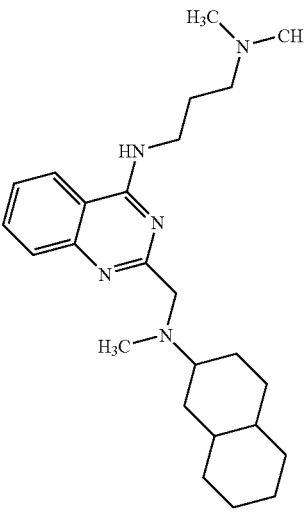 | 28.7 (3) |
| 103 | 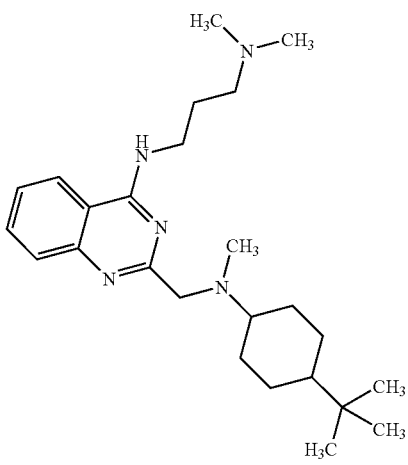 | 7.8 (2) |

TABLE 5-continued

Results from Scintillation Proximity Assays.

| Formula No. | Structural Formula | SPA ASSAY % Residual T @ 2 ug/mL of drug (Average of) |
|---|---|---|
| 104 | | 23.0 (2) |
| 105 | | 57.7 |
| 106 | | 52.8 |

TABLE 5-continued
Results from Scintillation Proximity Assays.
| Formula No. | Structural Formula | SPA ASSAY % Residual T @ 2 ug/mL of drug (Average of) |
|---|---|---|
| 107 | 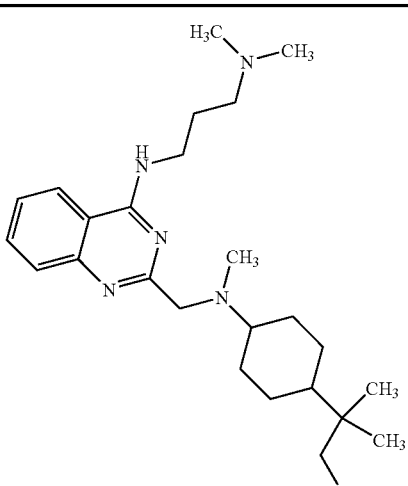 | 6.3 (2) |
| 108 | 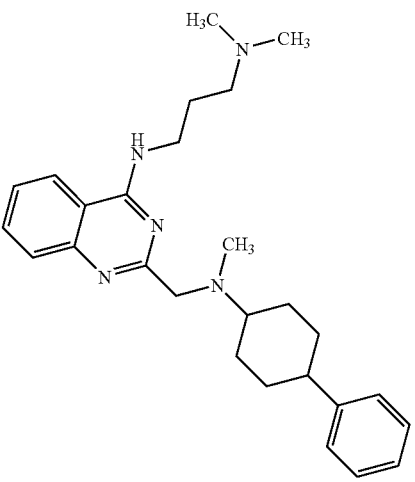 | 21.0 (2) |
| 109 | 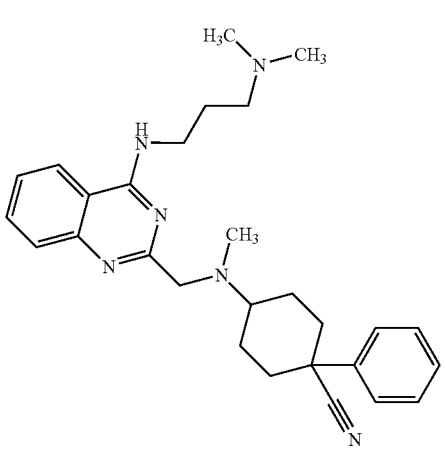 | 5.5 (2) |

TABLE 5-continued

Results from Scintillation Proximity Assays.

| Formula No. | Structural Formula | SPA ASSAY % Residual T @ 2 ug/mL of drug (Average of) |
|---|---|---|
| 110 | | 20.7 (2) |
| 111 | | 57.0 |
| 112 | | 48.4 |

TABLE 5-continued
Results from Scintillation Proximity Assays.
| Formula No. | Structural Formula | SPA ASSAY % Residual T @ 2 ug/mL of drug (Average of) |
|---|---|---|
| 113 | 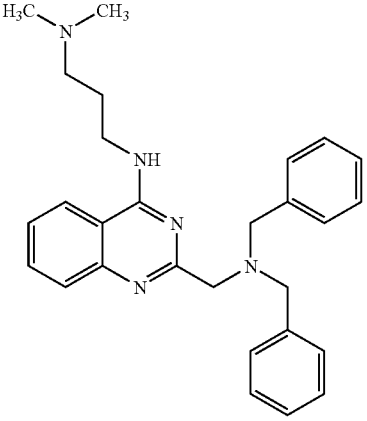 | 61.7 |
| 114 | 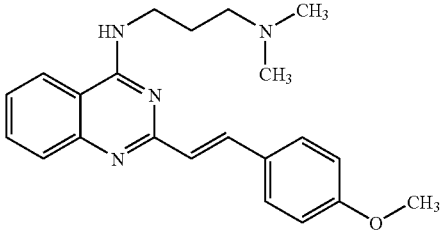 | 61.3 |
| 115 | 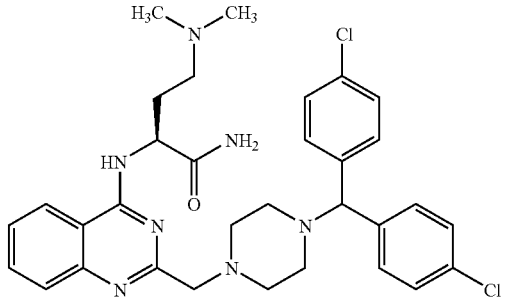 | 44.8 |

TABLE 5-continued
Results from Scintillation Proximity Assays.
| Formula No. | Structural Formula | SPA ASSAY % Residual T @ 2 ug/mL of drug (Average of) |
|---|---|---|
| 116 | 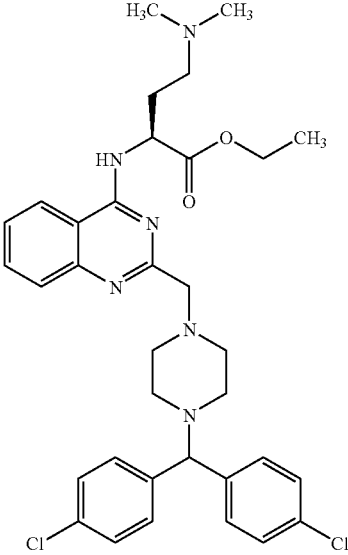 | 47.7 |
| 117 | 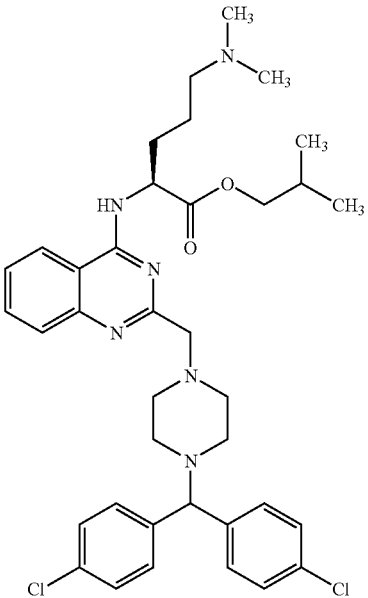 | 72.5 |

TABLE 5-continued

Results from Scintillation Proximity Assays.

| Formula No. | Structural Formula | SPA ASSAY % Residual T @ 2 ug/mL of drug (Average of) |
|---|---|---|
| 118 | 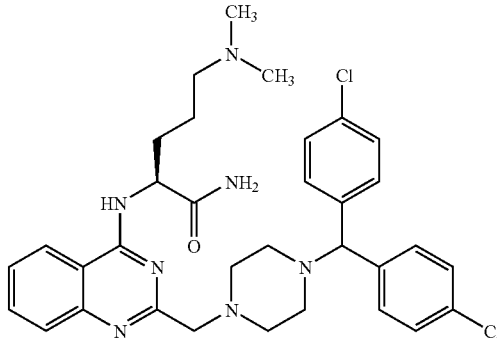 | 58.6 |
| 119 | 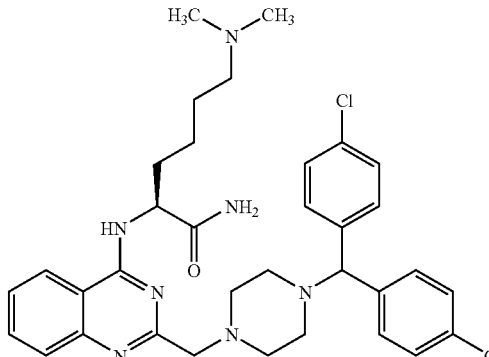 | 58.5 |

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

Patents, patent applications, publications, product descriptions, and protocols are cited throughout this application, the disclosures of which are incorporated herein by reference in their entireties for all purposes.

We claim:

1. A method for testing a substance for the presence of an anti-cancer agent or a p53 stabilizer comprising:

(a) contacting p53 polypeptide, in the presence of a known p53-binding substance, with a sample to be tested for the presence of said agent or stabilizer; wherein the known p53-binding substance is represented by a structural formula selected from the group consisting of:

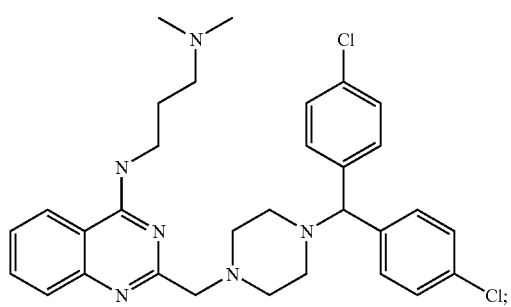

1

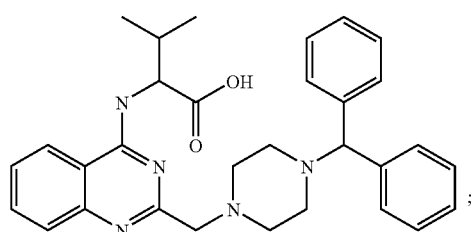

2

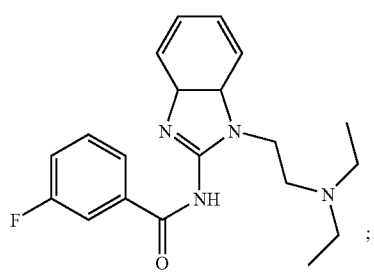

3

4
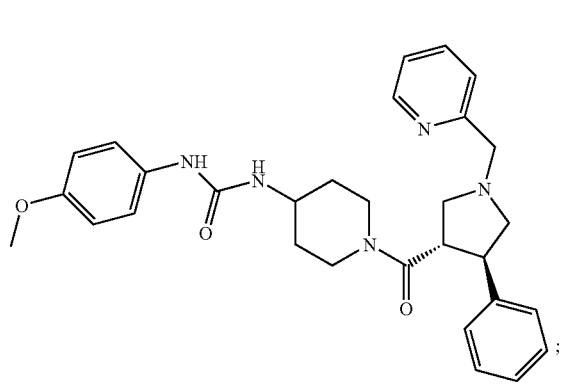
5
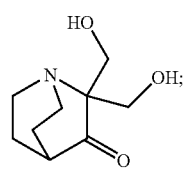
6
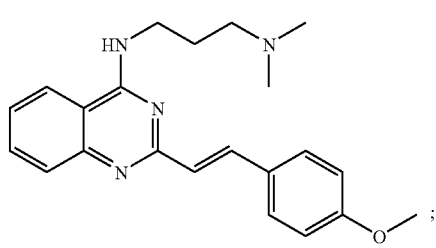
7
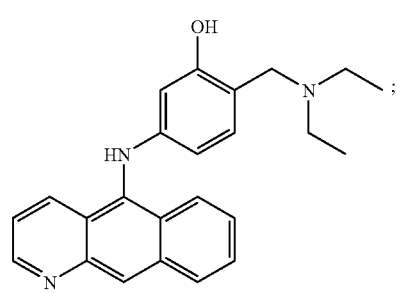
8
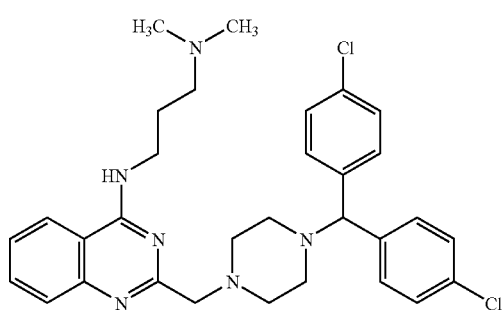
5
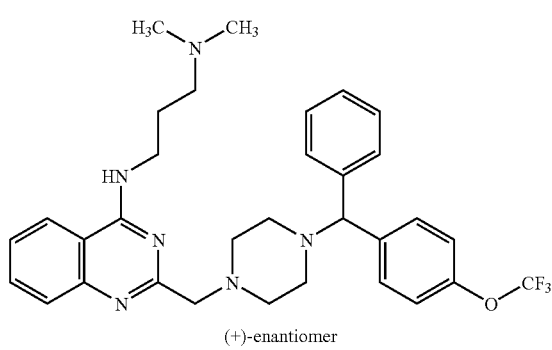
(+)-enantiomer
10
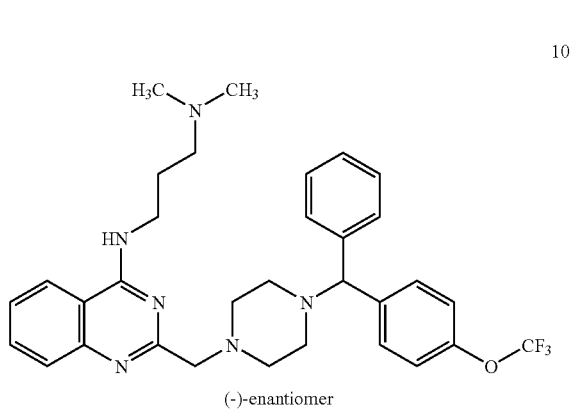
(−)-enantiomer
11
Chiral
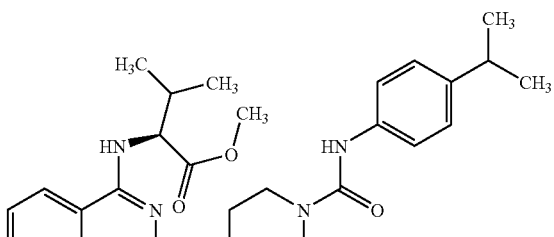
12
Chiral
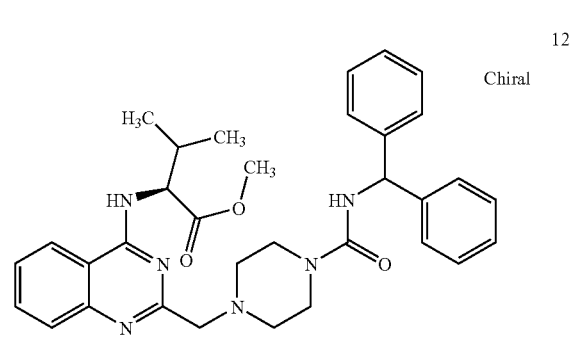

13
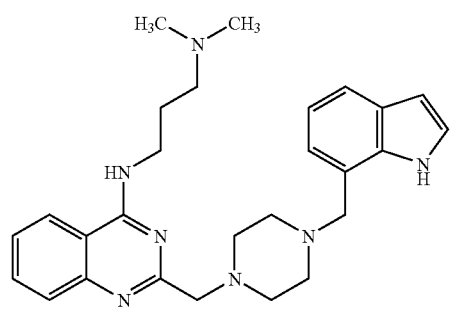
14
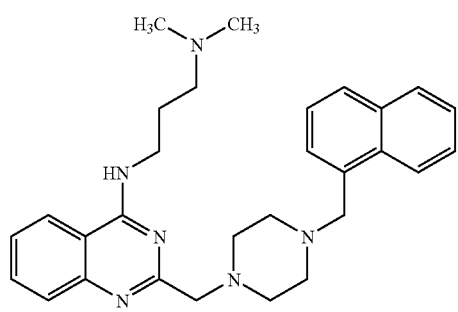
15
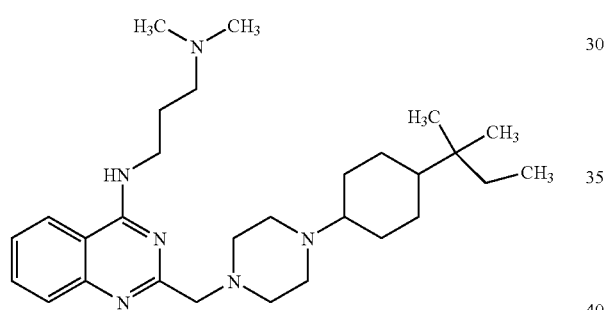
16
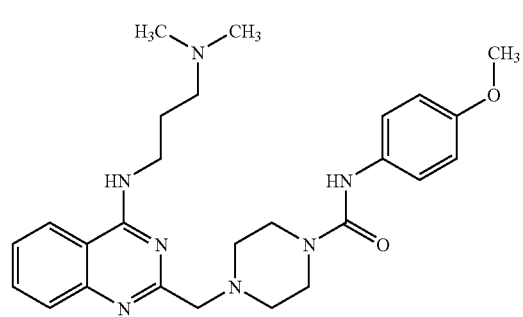
17
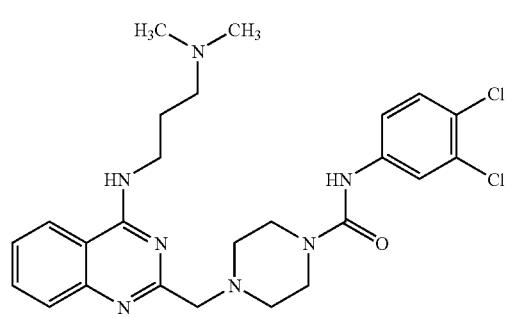
18
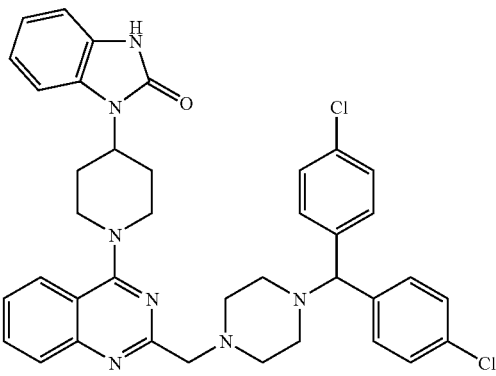
19
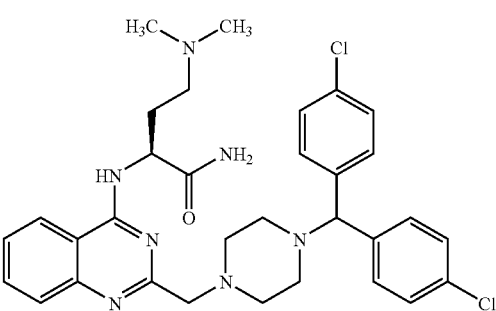
20
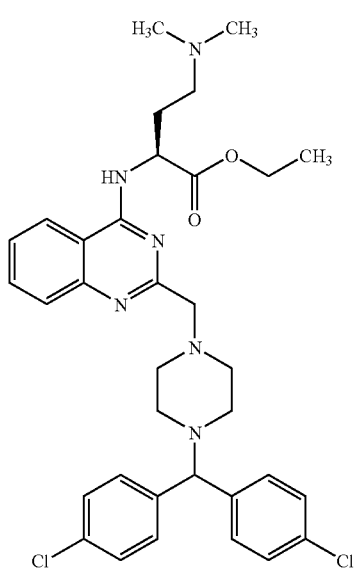

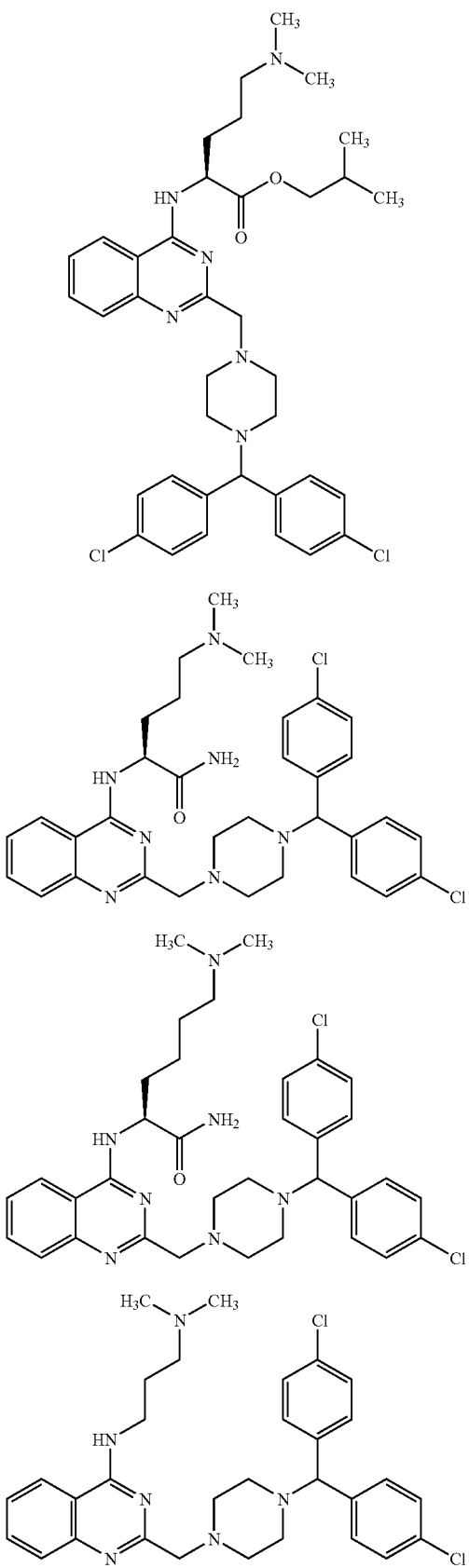
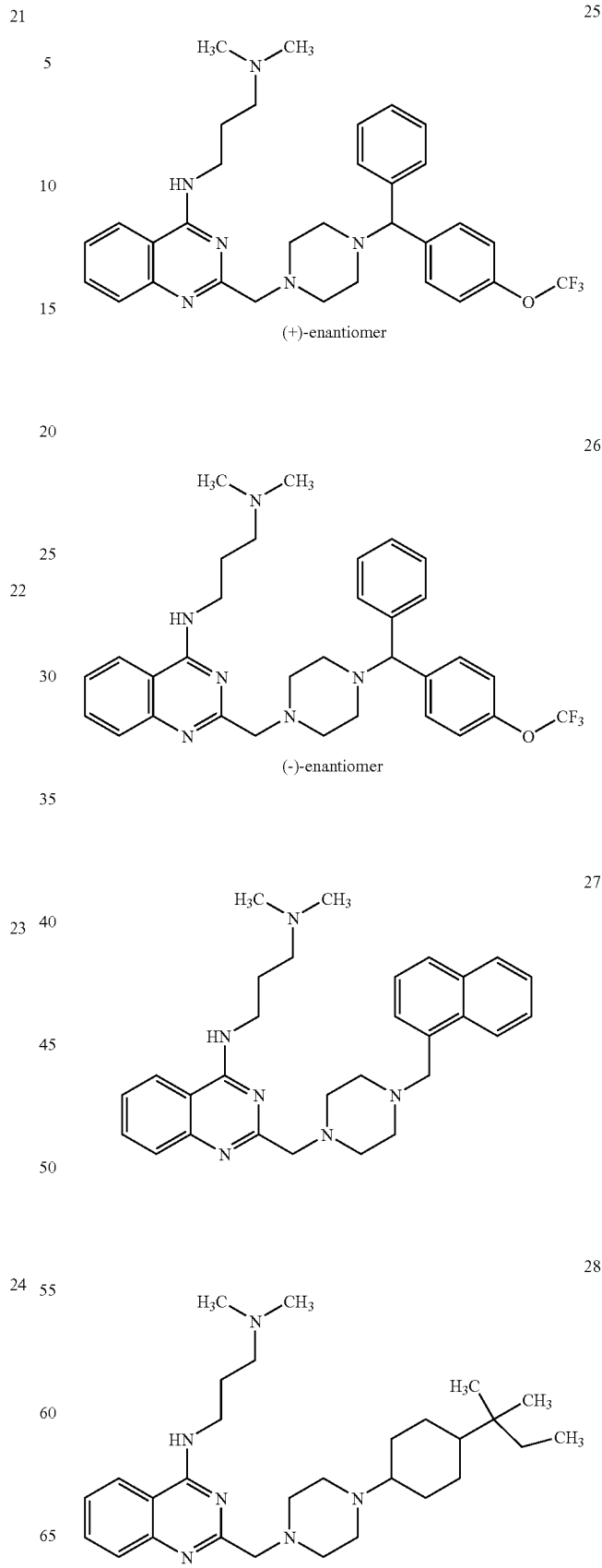

; and (b) measuring the amount of the known p53-binding substance specifically bound to the p53 polypeptide;

whereby the sample is identified as containing the agent or stabilizer by measuring substantially reduced binding of the known p53-binding substance to the p53 polypeptide, compared to that measured in the absence of the sample.

2. The method of claim 1 wherein the p53 polypeptide comprises the amino acid sequence of SEQ ID NO: 2 or amino acids 92-312 of SEQ ID NO: 2, optionally comprising one or more mutations selected from the group consisting of: R273H, R249S, R175H, R175P, R175C, S389A, R181C, R181H, R181L, R213H, G245V, G245S, R248Q, R248W, R249S, R273C, R273H and R273P.

3. The method of claim 1 wherein the known p53-binding substance is detectably labeled.

4. The method of claim 3 wherein the detectable label is selected from the group consisting of $^3H$, $^{131}I$, $^{35}S$, $^{32}P$ and $^{14}C$.

5. The method of claim 1 wherein the p53-binding substance is a represented by a structural formula selected from the group consisting of:

-continued

11

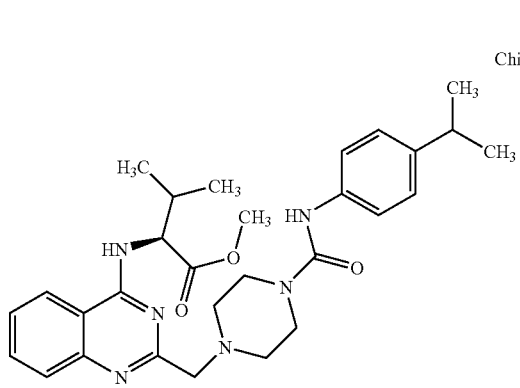

14

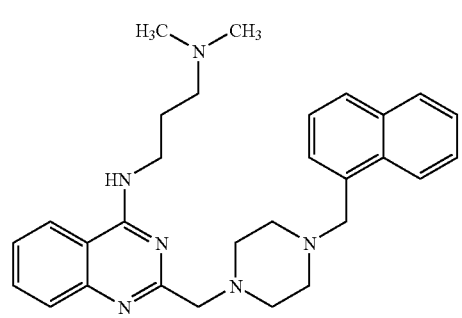

28

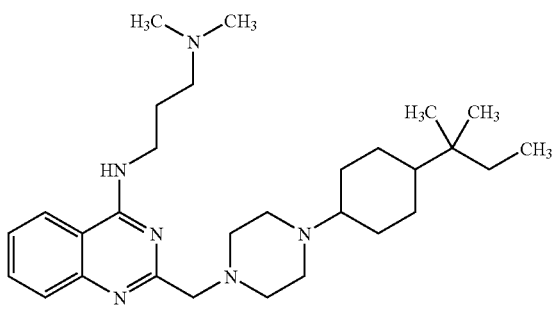

31

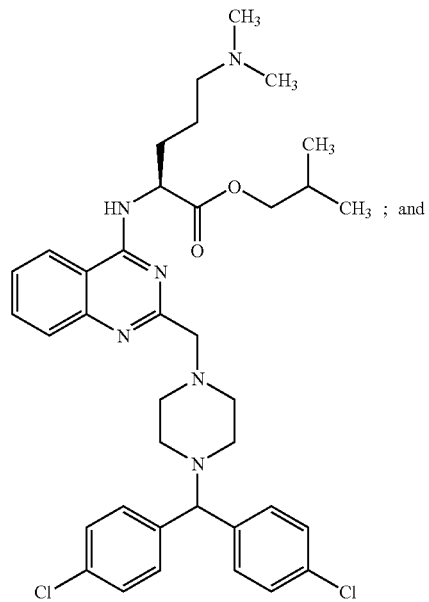

-continued

32

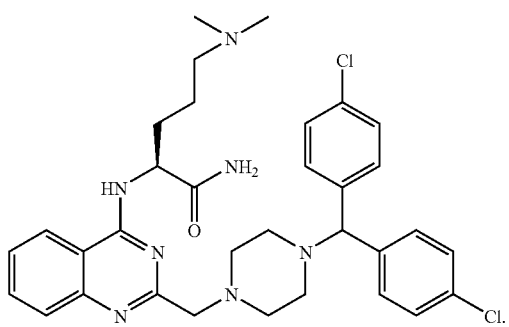

6. The method of claim 5 wherein the p53-binding substance is represented by the structural formula:

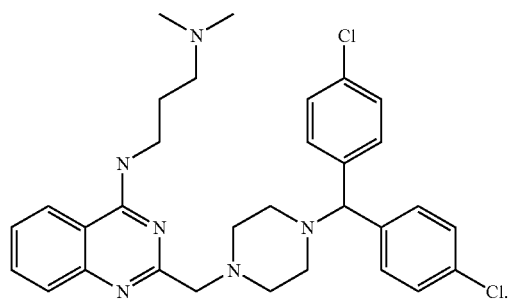

7. The method of claim 5 wherein the p53-binding substance is represented by the structural formula:

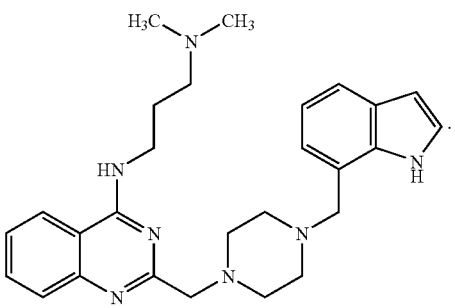

8. The method of claim 5 wherein the p53-binding substance is represented by the structural formula:

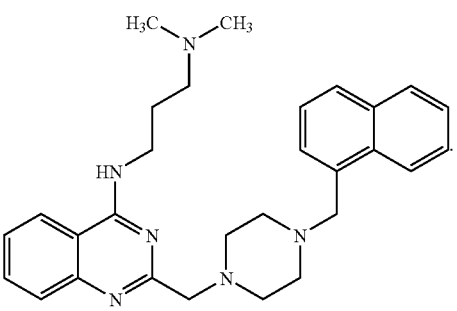

9. The method of claim 5 wherein the p53-binding substance is represented by the structural formula:

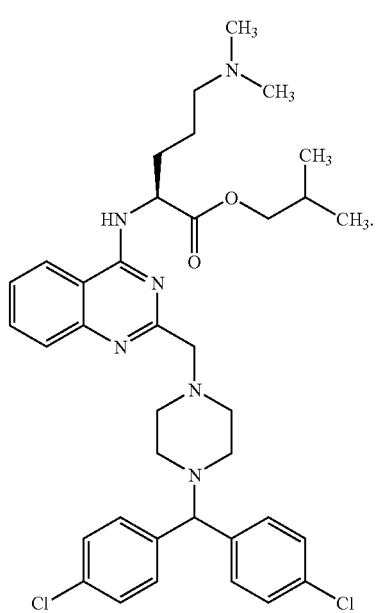
10. The method of claim 5 wherein the p53-binding substance is represented by the structural formula:
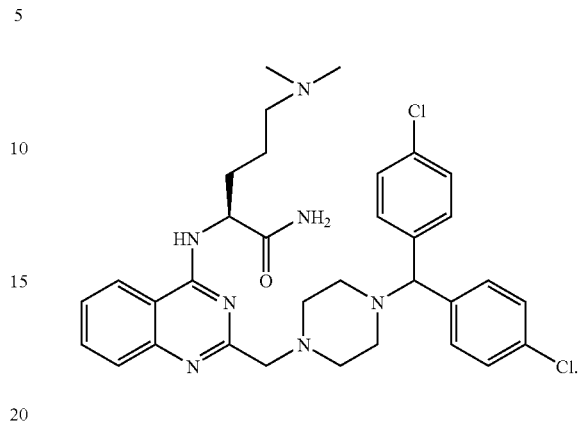
* * * * *

SEQUENCE LISTING

```
<160> NUMBER OF SEQ ID NOS: 4

<210> SEQ ID NO 1
<211> LENGTH: 1182
<212> TYPE: DNA
<213> ORGANISM: Homo sapiens
<220> FEATURE:
<221> NAME/KEY: CDS
<222> LOCATION: (1)..(1182)

<400> SEQUENCE: 1 atg gag gag ccg cag tca gat cct agc gtc gag ccc cct ctg agt cag      48
Met Glu Glu Pro Gln Ser Asp Pro Ser Val Glu Pro Pro Leu Ser Gln
1               5                   10                  15 gaa aca ttt tca gac cta tgg aaa cta ctt cct gaa aac aac gtt ctg      96
Glu Thr Phe Ser Asp Leu Trp Lys Leu Leu Pro Glu Asn Asn Val Leu
            20                  25                  30
```

```
tcc ccc ttg ccg tcc caa gca atg gat gat ttg atg ctg tcc ccg gac      144
Ser Pro Leu Pro Ser Gln Ala Met Asp Asp Leu Met Leu Ser Pro Asp
        35                  40                  45 gat att gaa caa tgg ttc act gaa gac cca ggt cca gat gaa gct ccc      192
Asp Ile Glu Gln Trp Phe Thr Glu Asp Pro Gly Pro Asp Glu Ala Pro
50                  55                  60 aga atg cca gag gct gct ccc ccc gtg gcc cct gca cca gca gct cct      240
Arg Met Pro Glu Ala Ala Pro Pro Val Ala Pro Ala Pro Ala Ala Pro
65                  70                  75                  80 aca ccg gcg gcc cct gca cca gcc ccc tcc tgg ccc ctg tca tct tct      288
Thr Pro Ala Ala Pro Ala Pro Ala Pro Ser Trp Pro Leu Ser Ser Ser
                85                  90                  95 gtc cct tcc cag aaa acc tac cag ggc agc tac ggt ttc cgt ctg ggc      336
Val Pro Ser Gln Lys Thr Tyr Gln Gly Ser Tyr Gly Phe Arg Leu Gly
            100                 105                 110 ttc ttg cat tct ggg aca gcc aag tct gtg act tgc acg tac tcc cct      384
Phe Leu His Ser Gly Thr Ala Lys Ser Val Thr Cys Thr Tyr Ser Pro
        115                 120                 125 gcc ctc aac aag atg ttt tgc caa ctg gcc aag acc tgc cct gtg cag      432
Ala Leu Asn Lys Met Phe Cys Gln Leu Ala Lys Thr Cys Pro Val Gln
130                 135                 140 ctg tgg gtt gat tcc aca ccc ccg ccc ggc acc cgc gtc cgc gcc atg      480
Leu Trp Val Asp Ser Thr Pro Pro Pro Gly Thr Arg Val Arg Ala Met
145                 150                 155                 160 gcc atc tac aag cag tca cag cac atg acg gag gtt gtg agg cgc tgc      528
Ala Ile Tyr Lys Gln Ser Gln His Met Thr Glu Val Val Arg Arg Cys
                165                 170                 175 ccc cac cat gag cgc tgc tca gat agc gat ggt ctg gcc cct cct cag      576
Pro His His Glu Arg Cys Ser Asp Ser Asp Gly Leu Ala Pro Pro Gln
            180                 185                 190 cat ctt atc cga gtg gaa gga aat ttg cgt gtg gag tat ttg gat gac      624
His Leu Ile Arg Val Glu Gly Asn Leu Arg Val Glu Tyr Leu Asp Asp
        195                 200                 205 aga aac act ttt cga cat agt gtg gtg gtg ccc tat gag ccg cct gag      672
Arg Asn Thr Phe Arg His Ser Val Val Val Pro Tyr Glu Pro Pro Glu
210                 215                 220 gtt ggc tct gac tgt acc acc atc cac tac aac tac atg tgt aac agt      720
Val Gly Ser Asp Cys Thr Thr Ile His Tyr Asn Tyr Met Cys Asn Ser
225                 230                 235                 240 tcc tgc atg ggc ggc atg aac cgg agg ccc atc ctc acc atc atc aca      768
Ser Cys Met Gly Gly Met Asn Arg Arg Pro Ile Leu Thr Ile Ile Thr
                245                 250                 255 ctg gaa gac tcc agt ggt aat cta ctg gga cgg aac agc ttt gag gtg      816
Leu Glu Asp Ser Ser Gly Asn Leu Leu Gly Arg Asn Ser Phe Glu Val
            260                 265                 270 cgt gtt tgt gcc tgt cct ggg aga gac cgg cgc aca gag gaa gag aat      864
Arg Val Cys Ala Cys Pro Gly Arg Asp Arg Arg Thr Glu Glu Glu Asn
        275                 280                 285 ctc cgc aag aaa ggg gag cct cac cac gag ctg ccc cca ggg agc act      912
Leu Arg Lys Lys Gly Glu Pro His His Glu Leu Pro Pro Gly Ser Thr
290                 295                 300 aag cga gca ctg ccc aac aac acc agc tcc tct ccc cag cca aag aag      960
Lys Arg Ala Leu Pro Asn Asn Thr Ser Ser Ser Pro Gln Pro Lys Lys
305                 310                 315                 320 aaa cca ctg gat gga gaa tat ttc acc ctt cag atc cgt ggg cgt gag     1008
Lys Pro Leu Asp Gly Glu Tyr Phe Thr Leu Gln Ile Arg Gly Arg Glu
                325                 330                 335 cgc ttc gag atg ttc cga gag ctg aat gag gcc ttg gaa ctc aag gat     1056
Arg Phe Glu Met Phe Arg Glu Leu Asn Glu Ala Leu Glu Leu Lys Asp
```

-continued

```
                340                 345                 350
gcc cag gct ggg aag gag cca ggg ggg agc agg gct cac tcc agc cac    1104
Ala Gln Ala Gly Lys Glu Pro Gly Gly Ser Arg Ala His Ser Ser His
        355                 360                 365 ctg aag tcc aaa aag ggt cag tct acc tcc cgc cat aaa aaa ctc atg    1152
Leu Lys Ser Lys Lys Gly Gln Ser Thr Ser Arg His Lys Lys Leu Met
370                 375                 380 ttc aag aca gaa ggg cct gac tca gac tga                            1182
Phe Lys Thr Glu Gly Pro Asp Ser Asp
385                 390

<210> SEQ ID NO 2
<211> LENGTH: 393
<212> TYPE: PRT
<213> ORGANISM: Homo sapiens

<400> SEQUENCE: 2

Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
    130                 135                 140

Leu Trp Val Asp Ser Thr Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Val Pro Tyr Glu Pro Pro Glu
    210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
        275                 280                 285

Leu Arg Lys Lys Gly Glu Pro His His Glu Leu Pro Pro Gly Ser Thr
    290                 295                 300
```

-continued

```
Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp
                340                 345                 350

Ala Gln Ala Gly Lys Glu Pro Gly Gly Ser Arg Ala His Ser Ser His
                355                 360                 365

Leu Lys Ser Lys Lys Gly Gln Ser Thr Ser Arg His Lys Lys Leu Met
        370                 375                 380

Phe Lys Thr Glu Gly Pro Asp Ser Asp
385                 390

<210> SEQ ID NO 3
<211> LENGTH: 9
<212> TYPE: PRT
<213> ORGANISM: Artificial Sequence
<220> FEATURE:
<223> OTHER INFORMATION: peptide

<400> SEQUENCE: 3

Arg Glu Asp Glu Asp Glu Ile Glu Trp
1               5

<210> SEQ ID NO 4
<211> LENGTH: 24
<212> TYPE: DNA
<213> ORGANISM: Artificial Sequence
<220> FEATURE:
<223> OTHER INFORMATION: consensus

<400> SEQUENCE: 4
agctggacat gcccgggcat gtcc                                              24
```